(12) United States Patent
Han et al.

(10) Patent No.: US 11,518,788 B2
(45) Date of Patent: Dec. 6, 2022

(54) METHODS AND COMPOSITIONS FOR TREATING AND PREVENTING VIRAL INFECTION

(71) Applicant: AVIRUS, INC., Lafayette, CA (US)

(72) Inventors: Jang Hyun Han, Lafayette, CA (US); William J. Rutter, San Francisco, CA (US); Mi-Young Seo, Seoul (KR)

(73) Assignee: AVIRUS, INC., Lafayette, CA (US)

( * ) Notice: Subject to any disclaimer, the term of this patent is extended or adjusted under 35 U.S.C. 154(b) by 0 days.

(21) Appl. No.: 17/246,307

(22) Filed: Apr. 30, 2021

(65) Prior Publication Data

US 2022/0009972 A1    Jan. 13, 2022

Related U.S. Application Data

(63) Continuation of application No. PCT/US2021/014818, filed on Jan. 23, 2021.
(Continued)

(51) Int. Cl.
| | |
|---|---|
| *C07K 14/47* | (2006.01) |
| *C07K 14/36* | (2006.01) |
| *A61K 31/727* | (2006.01) |
| *A61K 38/00* | (2006.01) |
| *C07K 14/165* | (2006.01) |

(52) U.S. Cl.
CPC ......... *C07K 14/165* (2013.01); *A61K 31/727* (2013.01); *C07K 14/36* (2013.01); *C07K 14/4725* (2013.01); *A61K 38/00* (2013.01); *C07K 2319/30* (2013.01)

(58) Field of Classification Search
CPC ............ C07K 2319/30; C07K 2319/31; C07K 14/005; A61K 47/68; A61K 39/12; A61K 39/215; A61P 11/00; A61P 9/00; A61P 31/14; C12N 2770/20034; C12Y 304/17023
See application file for complete search history.

(56) References Cited

U.S. PATENT DOCUMENTS

| | | |
|---|---|---|
| 6,511,832 B1 | 1/2003 | Guarino |
| 2002/0141974 A1 | 10/2002 | Jolly |

(Continued)

FOREIGN PATENT DOCUMENTS

WO    2021151043    7/2021

OTHER PUBLICATIONS

Liu et al., Novel ACE2-Fc chimeric fusion provides long-lasting hypertension control and organ protection in mouse models of systemic renin angiotensin system activation, Kidney International, vol. 94:114-125 (Apr. 22, 2018) (Year: 2018).*

(Continued)

*Primary Examiner* — Randall L Beane
(74) *Attorney, Agent, or Firm* — Dennis A. Bennett; Cynthia Hathaway; Stephanie Greer

(57) ABSTRACT

The disclosure provides recombinant polypeptides for treating or preventing viral infection comprising an immunoglobulin Fc fragment and at least one viral receptor or fragment thereof. Also provided are RNA molecules, therapeutic compositions, and expression systems comprising such recombinant polypeptides, along with methods of preventing or treating a viral infection in a subject in need thereof, comprising administering such recombinant polypeptides to a subject or patient.

8 Claims, 44 Drawing Sheets

Figure 1:
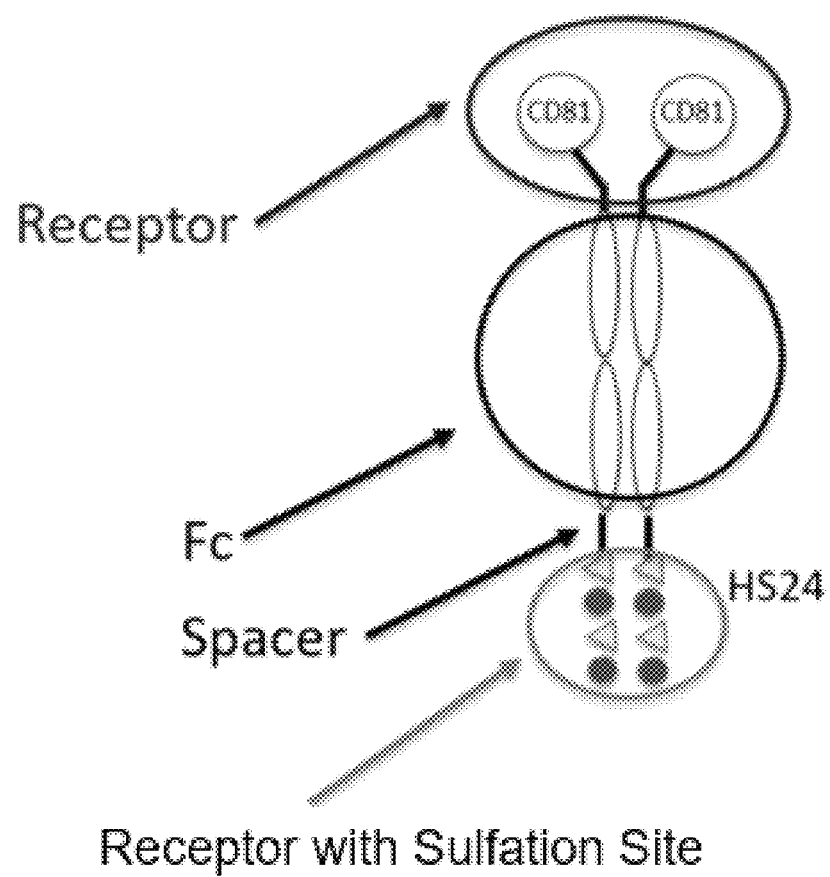

Specification includes a Sequence Listing.

Related U.S. Application Data

(60) Provisional application No. 63/050,473, filed on Jul. 10, 2020.

(56) References Cited

U.S. PATENT DOCUMENTS

| | | | |
|---|---|---|---|
| 2004/0063619 | A1 | 4/2004 | Carson |
| 2018/0230447 | A1* | 8/2018 | Batlle .................... A61K 47/60 |
| 2018/0289779 | A1* | 10/2018 | Schuster ................. C12N 9/48 |

OTHER PUBLICATIONS

Li et al., Potential host range of multiple SARS-like coronaviruses and an improved ACE2-Fc variant that is potent against both SARS-CoV-2 and SARS-CoV-1, Journal of Virology, 1-22, doi: https://doi.org/10.1101/2020.04.10.032342 (published online Apr. 11, 2020) (Year: 2020).*

Azadi et al., Comprehensive characterization of N- and O- glycosylation of SARSCoV-2 human receptor angiotensin converting enzyme 2, BioRxiv.org, doi: https://doi.org/10.1101/2020.05.01.071688 (May 2, 2020), pp. 1-32 (Year: 2020).*

"Infection", Merriam-webster.com, 5 pages, Jan. 2022, also available at https://www.merriam-webster.com/dictionary/infection (last visited Jan. 24, 2022) (Year: 2022).*

Dreux Marlène et al., Receptor Complementation and Mutagenesis Reveal SR-BI as an Essential HCV Entry Factor and Functionally Imply Its Intra- and Extra-Cellular Domains, PLoS Pathog. Feb. 2009; 5(2): e1000310., pp. 1-17.

International Application No. PCT/US2021/014818; International Search Report and Written Opinion of the International Searching Authority, dated Jul. 9, 2021, 17 pages.

Lang Jianshe et al., Inhibition of SARS pseudovirus cell entry by lactoferrin binding to heparan sulfate proteoglycans, PLoS One 2011;6(8):e23710, pp. 1-10.

Liu Pan et al., Novel ACE2-Fc chimeric fusion provides long-lasting hypertension control and organ protection in mouse models of systemic renin angiotensin system activation, Kidney International, Jul. 2018;94(1), pp. 114-125.

Annaval, T. et al., "Heparan Sulfate Proteoglycans Biosynthesis and Post Synthesis Mechanisms Combine Few Enzymes and Few Core Proteins to Generate Extensive Structural and Functional Diversity", Molecules, 25(18):4215, (Sep. 2020).

Marques, C. et al., "Heparan Sulfate Biosynthesis and Sulfation Profiles as Modulators of Cancer Signalling and Progression", Front Oncol., 11:778752, (Nov. 2021).

Annaval, T. et al., "Heparan Sulfate Proteoglycans Biosynthesis and Post Synthesis Mechanisms Combine Few Enzymes and Few Core Proteins to Generate Extensive Structural and Functional Diversity", Molecules, 25(18):4215, (2020), Sep. 2020.

Marques, C. et al., "Heparan Sulfate Biosynthesis and Sulfation Profiles as Modulators of Cancer Signalling and Progression", Front Oncol., 11:778752, (2021).

* cited by examiner

FIG. 3

FIG. 5

Receptor-Fc variants for Sars-CoV2

FIG. 6

Human SRB1
AltName: CD36

Human SRB1 extracellular domain seq: aa 33-443, 411 aa (SEQ ID NO:10)

```
                                PSLIKQQV LKNVRIDPSS LSFNMWKEIP
IPFYLSVYFP DVMNPSEILK GEKPQVRERG PYYYREFRHK SNITFNNHDT VSFLEYRTFQ
FQPSKSHGSE SDYIVMPNIL VLGAAVMMEN KPMTLKLIMT LAFTTLGERA FMNRTVGEIM
WGYKDPLVNL INKYFPGMFP FKDKFGLFAE LNNSDSGLFT VFTGVQNISR IHLVDKWNGL
SKVDFWHSDQ CNMINGTSGQ MWPPMTFES SLEFYSPEAC RSMKLMYKES GVFEGIPTYR
FVAPKTLFAN GSIYPPNEGF CPCLESGIQN VSTCRFSAPL FLSHPHFLNA DPVLAEAVTG
LHPNQEAHSL FLDIHPVTGI PMNCSVKLQL SLYMKSVAGI GQTGKIEFVV LPLLNFAESG
AMEGETLHTF YTQLVLMPKV MHY
```

Full-length seq: 552 aa, 6078 MW (SEQ ID NO:11)

```
MGCSAKARWA AGALGVAGLL CAVLGAVMIV MVPSLIKQQV LKNVRIDPSS LSFNMWKEIP
IPFYLSVYFP DVMNPSEILK GEKPQVRERG PYYYREFRHK SNITFNNHDT VSFLEYRTFQ
FQPSKSHGSE SDYIVMPNIL VLGAAVMMEN KPMTLKLIMT LAFTTLGERA FMNRTVGEIM
WGYKDPLVNL INKYFPGMFP FKDKFGLFAE LNNSDSGLFT VFTGVQNISR IHLVDKWNGL
SKVDFWHSDQ CNMINGTSGQ MWPPMTFES SLEFYSPEAC RSMKLMYKES GVFEGIPTYR
FVAPKTLFAN GSIYPPNEGF CPCLESGIQN VSTCRFSAPL FLSHPHFLNA DPVLAEAVTG
LHPNQEAHSL FLDIHPVTGI PMNCSVKLQL SLYMKSVAGI GQTGKIEFVV LPLLNFAESG
AMEGETLHTF YTQLVLMPKV MHYAQYVLLA LGCVLLLVPV ICQIRSQVGA GQRAARADSH
SLACWGKGAS DRTLNFTAAN SPPPAAVLRL CRSGSSHCWG LRSTLASFAC RVAFTLPVLE
GLGPSLGGGT GS
```

FIG. 7

Webarchive; uniprot
CD81 Human, full length, 236 aa (SEQ ID NO:14)

```
        10         20         30         40         50
MGVEGCTKCI KYLLFVFNFV FWLAGGVILG VALWLRHDPQ TTNLLYLELG
        60         70         80         90        100
DKPAPNTFYV GIYILIAVGA VMMFVGFLGC YGAIQESQCL LGTFFTCLVI
       110        120        130        140        150
LFACEVAAGI WGFVNKDQIA KDVKQFYDQA LQQAVVDDDA NNAKAVVKTF
       160        170        180        190        200
HETLDCCGSS TLTALTTSVL KNNLCPSGSN IISNLFKEDC HQKIDDLFSG
       210        220        230
KLYLIGIAAI VVAVIMIFEM ILSMVLCCGI RNSSVY
```

CD81 extracellular domain (EC-2), 89 aa; (aa#: 113-201)

(SEQ ID NO:15)

```
       110        120        130        140        150
           FVNKDQIA KDVKQFYDQA LQQAVVDDDA NNAKAVVKTF
       160        170        180        190        200
HETLDCCGSS TLTALTTSVL KNNLCPSGSN IISNLFKEDC HQKIDDLFSG
       210        220        230
K
```

ACE2-Fc-SA, nt sequence (2369 bp), IL2 leader (CAPITALIZED UNDERLINED), Linker (lowercase, underlined, bold), ACE2 (CAPITALIZED REGULAR TEXT), Fc (*CAPITALIZED, ITALICS*), Streptavidin (SA, lowercase, italics).

ATGTACAGGATGCAACTCCTGTCTGCAATGGCGAGACCTGTTCACTGTCTTGCACTAGTCTTGCACTGACTAGTAGTCgctctgaggGCTGCTCAGTCCACCATTGAGGAACAGGCCAAGACATTTTT
GGACAAGTTTAACCACGAAGCCGAAGACCTGTTTTATCAGTCTTCACTGTCTTATCAAAGTTCACTGCTTCTTGTCACCAATTACACCAAGAATTACTCACCAAGCTCCAAACATGAATAATGCT
GGGACCAAATGGTCTGCCTTTTAAGGAACAGTCACAGAGCCAAGACCAAGACAAGAACCAAACGGTTGAACACAGTCTAATACAATGAGCACCATTCAGAATTCAGTAATTGGAATAAATCAGA
CAAAATGGGTCTTCAGTGCTCTCAGAAGACAAGAACAAGAACCAAACGGTTGAACACAGTCTAATACAATGAGCACCATTCAGAATTCAGTAATTGGAATAAATCAGA
CCACAAGAATGCTTATTACTTGAACCAGTTTGAATGAAATATGCAAGACTTTAGACTCAAGAGCAAATCATTATGAGGACTATTGGAACAGAGACTATGAAGTA
AAGCAGCTGAGGCCATTATATGACTATAGTGGTCTTGAAAAATGAGATGGCAAGACATGAGGTGAAATCATTATGAGGACTATTGGAACAGAGACTATGAAGTA
AAAGTTGATGAATGCTATAGACTACACGCGGCGGCCAGTCAATGCAATGGTGCCTCCTGCCATTGTCCGATCCAAATACTCAAGCCTAGTGAGGGC
TCCCTTTGGACACAGAAACCAAACATAGAGTTACTGATGCAATGGTGCAATGGTCACAGAAGTTCAGAAGAGCCTGGGATGCAAGAATATTCAAGGAGGCCGAGAAGTTCTTTTAGCTGTGG
TCTCCTAAAATGACTCAAGGATTCTGGGAAATTCCATGCTAAAGGACCCCAGACAGTCAAGAAGTTCCATCCCACAGTCTGGACCTGGGAAGGCGA
CTTCAGGATCCTTAGTGCACAAAGGATTCCATGAAGCTGTTTGGGGAACAGCTCACGTTCTGTCAAACAGCCACTCACGATTGTGGGAAGCCAGTCAAGCAGTTACTTACGAACCATTGTCCGAT
TAAGAGACACATGAACAGAAACCAGGTCATGGGATGGAACGGGAAACCAGGATCCAAGGTGGGGTCTGGGAACCCTGATGAACTAGTGACC
CAAGAGAAACGAAATTCCAGAAGCTGTCTGCTTGATGGATAGCATTCATGAAGAGGAAATCAAGAATCACAGAAGCACTTCGTCAAGACCTAAACATGAA
CCGACATCTGTTTCCACAAATGTGACATCTCTAATGATTACGAACATCATGGAAGAAGACGTTCAATATGCTAGGCGTTGGAGAATCTGACCAAGCCCTAGCATTGGAAAAT
GGCCTCTGCAGCAACGGCTATGGAACATGAGATCAGACGAATCTAACTAGTAAGGCCACTACTTGACCCTAATCAAAGTGAGGATAAGCTCAAGTGAGGATAAGCTCCGACTCAACTACTAGAGGAGG
GTTGTAGGAGCAAAGAACATGACAGACGAGCAGTACTCTCAGCTCCAAAATGAATGACTCAAACTACATTTTTAAAGTACTAAAATCAGAGAAGATTCTTTTAAAGTAATAAAATCAGAGAATGATGAGTACC
GACTGGAGTCCATATGCTACTGACTCACCTAAAATGTGTGTATCAGCAGTATCCTAGAACTGAAGTGATATCATTCCGGAGACCTATCATGATTGGGATGTGCTAATTGAAACCAAGAATCTCCTT
TAATTTCTTTGTCACTCACCTAGGAGTTGTCTGGGAGATACAGGAGCAACAGGTAGGCCCACTGAAGGAGGAGGCCATGAGGCCGAGCCCGGAGCCCATCAATAGATGCTTTCCGTCTGA
ATGACAACAGCCTAGAGTTCTGGGAGATACAGCAGCAACACTCTTTGACCTCCTAACAGCCCGTGCCgctctcgaggtcgagctgcggccgccaccaaaggagcag
atgccacaggagccaggagccctgacctccggaactccggggacaccctccagcgacccagcgatctcccctgctacgaccaccatgcaggagcagcatgctcgcagcacgccgtcatggcggccgtggctgccgccctgacctccaatgc
TGGACCGGTGAGCCCCACCAGCGTCCAGCGAACACCAGGGTCAAGTTCATCGGCTAAGTGGTCAAGTTCCAAGGCACAACCTGTGAGTCAGGCCAGGACCAGCTGATCTCCCGGACCCATGATCTTCCCGGCACACCCCTGAATTCTCCCAAAACCCAAGACACCCATGATCTCCGGACCCCAGTGGGACCTGTTGACGGCGTGGCCCACCCCTGATCTCCGGGAACCTTCCTGGTGCACAACCGCGCACTGGTGGGAGCCTGAGGCTGCAGACCCCTCCTCGCAGCCCAGCCTGGGGCCACTCCTCTGGCACCCCCATGCAAACCTCCTCCAGCCCCCTACCCCTAAAACCTGTGCCAAGTGCACAAGCCTAGCCACTGCCGACCCCTGCCCCCATGATCGGCCATCGGGATGGTGCCAAGACTGTCCAGTTCAAGTGCTGCAGGCCAGGCCCCATCGGCCGCAAGCCGGCCGCAGACAGTGAGCGGGCGGCCAGGGCACCACCATGGGCACAGTGTCAGCTGGAGCGGACACCAAATGGTGAACAGTCCAGGCAAGAAGCAAGGGGCGCTCAGGACGGCGCTCCAAATGAAGCGTGGAACTTCCCGGCGAGCCCCGTCGACACCTCTAGCAACCCCAACAGCGAAGCTGCAAAGCCCCTCGGCCGGGCAGGCCGTGTCCAGCAGCGCCGGCTCAGCTGGCACCGGCAGGCAGCCGAATCCAGGATCCCGACCCCTGGCTTCGGCCAGACACTGCTCTCCGCGATCTCCGCGATGCTCAGCCCAGCCCCACCACCATGCAGAGCGAAAGCGATTCGTCCACCCGCAGAGCTACACATCAGCAGCGGCCGTCCAACCCATCCCAGCCCCGCAACTCGCCTCAGCAGCCGGCGGCGCAGCGCCGGACCCCGACTGCCCCGCAGCGGCTGGGCCGGTCAGCCTCGAGCTGCAGGAAGCTGGGGGAGGTCCCCTAAAGGCGAAGGCCAGACCAGCCCTCCCAGCCCGACGGCCACCTGGCTGCGCTCAGCAGGGCCGGATACCCCCAGCCCGCCCCGGTCTTCCAGAGCCCGGAGCCAGGGGTCAGAAAGCAGCCCCTAGGCGCGTTGGAGGCGAGCCGAGCCCGACGGCACACACCTCATCGCCGCTACTCCAGCCCCGGCCGGCCGGCTGCAGTCGATCCGCATGCGGAGCCTGCCAAGGCCTGGGAAGGATCCAGGGGGGCAGGATCTGCCAGACTGGAGTCCCAGAAGACCTCAACACATCATCTATCCAGCAGCCAGCGCCCGCTCAGGAGAGCGCATCCAGCCGATCCATTTCCGAGCGTGGAAGGCCTTGGGGCATCCGCCCCCGAGCGTGGTCCGCAGCCCGCTCCCGCTCCGGTGCCCCAGGCCCAACAAGCCCATCAGCCCGAGGGGAGGCAGGTCCGAGCCCAGCCTAGTGCCCCATACCTGGAGCTGCCCGTCTAGCTCGCACCGCGGTCTAGAAGCCCGGTTTCCCCTATTTCTCCGGCAGGCAGCCCGTGGTTCTTCCAGTCCCTTCCCAGGACTGACCTCCCCGCCTCGACCGCCCCGCCTGAACATCAGGGAGCGTCTCCAGCAAACCGGCCCTTTCCGCGCGCCGTCTCCACCCTGCTCCTCTGCCTCCGCTCCTGGTCTCGCCTCCGCCTGCCAGCAGCGCCGGGGGACGGGCCCGGGCAGCCAGGAAGACGTCCGTCTTCATGGGCAGCAGGAAGACCGTCGCTCGTTCGTCTCCGTATCCTCCGTATGCTCGCAGCATCTCGGTAGGGGTACCCTGATCCTGGACACCTCCGGGTTTTACCAAAATCAGACTTGCAGCGGCGACGGTCAGGGGAAATGCAGCCCGTCCGTGAAGCTCCGAGGAGCTCCCCATCCCCCCGACGCCGCGAGCCGGAGACCCATCCAAGCGGGGCCCTCCCAGGACCCACCTCCAGCCAGGACCAGCCCGCTCCATGTAAG

FIG. 31B

ACE2-Fc-SA aa sequence, IL2 leader (CAPITALIZED UNDERLINED), Linker (lowercase, underlined, bold), ACE2 (CAPITALIZED REGULAR TEXT), Fc (*CAPITALIZED, ITALICS*), Streptavidin (SA, *lowercase, italics*).

MYRMQLLSCIALSLALVTNSgsrAAQSTIEEQAKTFLDKFNHEAEDLFYQSSLASWNYNTNITEENVQNMNNAGDKWSAFLKEQSTLAQMYPLQEIQNLTVKLQLQALQQNGSSVLSEDKSKRLNTILNTMSTIYSTGKVCNPDNPQECLLLEPGLNEIMANSLDYNERLWAWESWRSEVGKQLRPLYEEYVVLKNEMARANHYEDYGDYWRGDYEVNGVDGYDYSRGQLIEDVEHTFEEIKPLYEHLHAYVRAKLMNAYPSYISPIGCLPAHLLGDMWGRFWTNLYSLTVPFGQKPNIDVTDAMVDQAWDAQRIFKEAEKFFVSVGLPNMTQGFWENSMLTDPGNVQKAVCHPTAWDLGKGDFRILMCTKVTMDDFLTAHHEMGHIQYDMAYAAQPFLLRNGANEGFHEAVGEIMSLSAATPKHLKSIGLLSPDFQEDNETEINFLLKQALTIVGTLPFTYMLEKWRWMVFKGEIPKDQWMKKWWEMKREIVGVVEPVPHDETYCDPASLFHVSNDYSFIRYYTRTLYQFQFQEALCQAAKHEGPLHKCDISNSTEAGQKLFNMLRLGKSEPWTLALENVVGAKNMNVRPLLNYFEPLFTWLKDQNKNSFVGWSTDWSPYADQSIKVRISLKSALGDKAYEWNDNEMYLFRSSVAYAMRQYFLKVKNQMILFGEEDVRVANLKPRISFNFFVTAPKNVSDIIPRTEVEKAIRMSRSRINDAFRLNDNSLEFLGIQPTLGPPNQPPVSgpsgssaepkscdkthtcppcpa*PELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG*Kartgggggs*eagitgtwynqlgstfivtagadgaltgyesavgnaesrywltgrydsapatdgsgtfalgwtvawkmnyrnahsaltwsgqyvggaerintqwlltsgtteanawkstivghdtffkvkpsaas*

FIG. 32A

Ace2Fc-Avitag nt sequence (3036 bp); IL2 leader (CAPITALIZED UNDERLINED), Linker (lowercase, underlined, bold), ACE2 (CAPITALIZED REGULAR TEXT), Fc (*CAPITALIZED, ITALICS*), AviTag™ *lowercase, italics*).

FIG. 32B

Ace2Fc-Avitag aa sequence: IL2 leader (CAPITALIZED UNDERLINED), Linker (lowercase, underlined, bold), ACE2 (CAPITALIZED REGULAR TEXT), Fc (*CAPITALIZED, ITALICS*), AviTag™ *lowercase, italics*).

<u>MYRMQLLSCIALSLALVTNS</u>gsrAAQSTIEEQAKTFLDKFNHEAEDLFYQSSLASWNYNTNITEENVQNMNNAGDKW SAFLKEQSTLAQMYPLQEIQNLTVKLQLQALQQNGSSVLSEDKSKRLNTILNTMSTIYSTGKVCNPDNPQECLLLEP GLNEIMANSLDYNERLWAWESWRSEVGKQLRPLYEEYVVLKNEMARANHYEDYGDYWRGDYEVNGVDGYDYSR GQLIEDVEHTFEEIKPLYEHLHAYVRAKLMNAYPSYISPIGCLPAHLLGDMWGRFWTNLYSLTVPFGQKPNIDVTDAM VDQAWDAQRIFKEAEKFFVSVGLPNMTQGFWENSMLTDPGNVQKAVCHPTAWDLGKGDFRILMCTKVTMDDFLTA HHEMGHIQYDMAYAAQPFLLRNGANEGFHEAVGEIMSLSAATPKHLKSIGLLSPDFQEDNETEINFLLKQALTIVGTL PFTYMLEKWRWMVFKGEIPKDQWMKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAKNMNVRPLLNYFEPLFTWLKDQNK NSFVGWSTDWSPYADQSIKVRISLKSALGDKAYEWNDNEMYLFRSSVAYAMRQYFLKVKNQMILFGEEDVRVANLK PRISFNFFVTAPKNVSDIIPRTEVEKAIRMSRSRINDAFRLNDNSLEFLGIQPTLGPPNQPPVSgpsgssaepkscdkthtc ppcpa*PELLGGPSVFLFPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEALHNHYTQKSLSLSPGK*artggggg sg*lndIfeaqkIewhe*

FIG. 33A

Ace2-Fc-Strep-Tag II® nt sequence (2394 bp): IL2 leader (CAPITALIZED UNDERLINED), Linker (lowercase, underlined, bold), ACE2 (CAPITALIZED REGULAR TEXT),
Fc (*CAPITALIZED, ITALICS*), Strep-Tag II® *lowercase, italics*).

ATGTACAGGATGCAACTCCTGTCTTGCATTGCACTAAGTCTTGCACTGTGCACGAATTCggctcgaggGCTGCTCAGTCCACCATTGAGGAACAGGCCAAGACATTTTGGAC
AAGTTAACCACGAAGCCAACCCTGTCTTGCATTGCACTAAGTCTTGCACTGTGCACTGCACGAATTCggctcgaggGCTGCTCAGTCCACCATTGAGGAACAGGCCAAGACATTTTGGAC
ATGTCTGCCTTTTAAAGGAACAGTCAGTCCAAACCTGTCTTATCAAAGTTCACTGTTCTATCAAAGTTACACCAATATACTGAAGAGAATGTCCAAAACATGAATAATGCTGGGACAA
TCAGTCCTTCAAGAACAGAGAGCAAACGGTTGACAACAATTTGCAACAGTTTAGACTACAATGAGAGGCTCTGGGCTTGGGAAAGCTGGAGATCGGCAGCGATGGCTATGACTAC
TGAAGAGTATGTGGTCTTGAAAATGACGATGCAAGCAAACATACCTTTGAAGAGATTGAGAACATCTTCATGTGAGGCAAGTTGATGAATGCTATCCTTCCTAT
AGCCCGCGCCAGTTGATTGAAGATGTGGAACATGCTCATTGCTTGTGTGGGTAGATTTGGGTAAGGCCGACAAATCGTACTCTTGACAGTTCCCTTTGACAGGACGAAGTAGATGTT
ATCAGTCCAATTGGAGGCTCCCTCAATGTTCAGAAGATGTGCACAAGCAGTCGCCATCAAGCTGTGAGAATTCGAGAAAATCCAAGGATTCTGACATGGACGA
CATGATTCACTTTCTGCAGCCACGAGATCAGGGCCATTACTTAGACAGGGCCATGATAGCATCAAGCACTGCACTGACCCAAGATCCTTAGAAGATCATGAAGTGTTGGGA
AATCATGTCACTTCGGACCTCCAATGCCATGTGGCAGATAGTTGGGCGCCGCCATGTGCCCAGCAAGCTGCAGCTGCACCTTGTCAAGAAGAGCCTGTCAAAGATCAAAGCAC
AGGGAGAGATAGTTGGGGTGGTGTCAAGAAGCAGATCAGAAGAACAGGCACTCCCTGTCAAGAAGGCCCTCTGCAACACTGTGACCATCGATGAATCGAAAGCAGGATGGTCAA
CCCTTACCAATTCCAGTTCGAAATCAGAAGCTGGAACAGAAGAATTTCTTTGGAAATGTTAGGAGCAAGATGCATGAAGCAGCTAAACCCATCAAAGCTGCACTGCCACTTTGAGCCCCTTATTACCT
TATGCTGAGGCTTGAAATGCCACCAGAACGACTGAAATTGCAAGAACCAAGAATTCTTTGGATGGAGTCCATATGTGCATGCCAAGTGCCAGAGCTGGAGATAAGCATCAAGCATTAGAGAGGATAGCAGTACTTTTAAAGTAAAACCTAAAAATCAGCTCTGGAGATA
AGCCATGAATGCAAGCAGAAGGACGAAGGACCAAGAAGATCAAGAAAGACAATGAAACGAACATGAACTTGTTCAAGTACTCGTTGCCATGCTGTTCCATCTCGATGAGGCAGTACTTTTAAAGTAAAACCTAAAAATCAGCTCTGGAGATA
ATGTGCGAGTGGCTAATCAATGATGCTTTCCGTCCGACCTAATTGAAACAGACAGGAGCTGCCACTCTCATCTTTTGTGTGGATGGAACGTAAGGATGATGATGGACAGGTGCTGAATCATTCCTGAGACTGAAGTTGAAAAGGCCATCAGGATGT
CCCGGAGCCGGATCAATGATGCTTTCCGTCCGACCTAATTGAAACAGACAAGAGTTTCTGGGGGATACAACAGCCTTCTGAGTTTCTGGGGGATACAACAGCCTTCTGAGTTTCTGGGGGATACAACAGCCTTCTGAGTCCTAACCAGCCCCGTTTCgggtcctcgagctcg
*agtctgaggccaaatctttgacaaaactcacacatgccccaccgtgcccagcaCCTGAACTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTA
CAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGA
GAAAACCATCTCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAAgctagctg*
*gagtcatccacaatlcgaaaag*TAG

FIG. 33B

Ace2-Fc-Strep-Tag II® aa sequence IL2 leader (CAPITALIZED UNDERLINED), Linker (lowercase, underlined, bold), ACE2 (CAPITALIZED REGULAR TEXT), Fc (*CAPITALIZED, ITALICS*), Strep-Tag II® *lowercase, italics*).

MYRMQLLSCIALSLALVTNSgsrAAQSTIEEQAKTFLDKFNHEAEDLFYQSSLASWNYNTNITEENVQNMNNAGDKW
SAFLKEQSTLAQMYPLQEIQNLTVKLQLQALQQNGSSVLSEDKSKRLNTILNTMSTIYSTGKVCNPDNPQECLLEPG
LNEIMANSLDYNERLWAWESWRSEVGKQLRPLYEEYVVLKNEMARANHYEDYGDYWRGDYEVNGVDGYDYSRG
QLIEDVEHTFEEIKPLYEHLHAYVRAKLMNAYPSYISPIGCLPAHLLGDMWGRFWTNLYSLTVPFGQKPNIDVTDAMV
DQAWDAQRIFKEAEKFFVSVGLPNMTQGFWENSMLTDPGNVQKAVCHPTAWDLGKGDFRILMCTKVTMDDFLTAH
HEMGHIQYDMAYAAQPFLLRNGANEGFHEAVGEIMSLSAATPKHLKSIGLLSPDFQEDNETEINFLLKQALTIVGTLPF
TYMLEKWRWMVFKGEIPKDQWMKKWWEMKREIVGVVEPVPHDETYCDPASLFHVSNDYSFIRYYTRTLYQFQFQE
ALCQAAKHEGPLHKCDISNSTEAGQKLFNMLRLGKSEPWTLALENVVGAKNMNVRPLLNYFEPLFTWLKDQNKNSF
VGWSTDWSPYADQSIKVRISLKSALGDKAYEWNDNEMYLFRSSVAYAMRQYFLKVKNQMILFGEEDVRVANLKPRIS
FNFFVTAPKNVSDIIPRTEVEKAIRMSRSRINDAFRLNDNSLEFLGIQPTLGPPNQPPVSgpsgssaepksedkthtcppcp
a*PELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK*aawshpqfek"

SEQUENCE LISTING

<160> NUMBER OF SEQ ID NOS: 52

<210> SEQ ID NO 1
<211> LENGTH: 24
<212> TYPE: PRT
<213> ORGANISM: Human
<400> SEQUENCE: 1

Asp Asp Glu Tyr Met Leu Ala Asp Ser Ile Ser Gly Asp Asp Leu Gly
1               5                   10                  15

Ser Gly Asp Leu Gly Ser Gly Asp
            20

<210> SEQ ID NO 2
<211> LENGTH: 21
<212> TYPE: PRT
<213> ORGANISM: human
<400> SEQUENCE: 2

Asp Asp Glu Tyr Met Leu Ala Asp Ser Ile Ser Gly Asp Asp Leu Gly
1               5                   10                  15

Ser Gly Asp Leu Gly
            20

<210> SEQ ID NO 3
<211> LENGTH: 16
<212> TYPE: PRT
<213> ORGANISM: human
<400> SEQUENCE: 3

Asp Asp Glu Tyr Met Leu Ala Asp Ser Ile Ser Gly Asp Asp Leu Gly
1               5                   10                  15

<210> SEQ ID NO 4
<211> LENGTH: 21
<212> TYPE: PRT
<213> ORGANISM: human
<400> SEQUENCE: 4

Met Glu Thr Asp Thr Leu Leu Leu Trp Val Leu Leu Leu Trp Val Pro
1               5                   10                  15

Gly Ser Thr Gly Asp
            20

<210> SEQ ID NO 5
<211> LENGTH: 20
<212> TYPE: PRT
<213> ORGANISM: human
<400> SEQUENCE: 5

Met Tyr Arg Met Gln Leu Leu Ser Cys Ile Ala Leu Ser Leu Ala Leu
1               5                   10                  15

Val Thr Asn Ser
            20

<210> SEQ ID NO 6
<211> LENGTH: 24
<212> TYPE: PRT
<213> ORGANISM: human
<400> SEQUENCE: 6

Met Pro Met Gly Ser Leu Gln Pro Leu Ala Thr Leu Tyr Leu Leu Gly
1               5                   10                  15

```
Met Leu Val Ala Ser Val Leu Ala
            20
```

<210> SEQ ID NO 7
<211> LENGTH: 21
<212> TYPE: PRT
<213> ORGANISM: human

<400> SEQUENCE: 7

```
Met Glu Thr Asp Thr Leu Leu Leu Trp Val Leu Leu Trp Val Pro
1               5                  10                  15

Gly Ser Thr Gly Asp
            20
```

<210> SEQ ID NO 8
<211> LENGTH: 20
<212> TYPE: PRT
<213> ORGANISM: human

<400> SEQUENCE: 8

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 9
<211> LENGTH: 24
<212> TYPE: PRT
<213> ORGANISM: human

<400> SEQUENCE: 9

```
Met Pro Met Gly Ser Leu Gln Pro Leu Ala Thr Leu Tyr Leu Leu Gly
1               5                   10                  15

Met Leu Val Ala Ser Val Leu Ala
            20
```

<210> SEQ ID NO 10
<211> LENGTH: 411
<212> TYPE: PRT
<213> ORGANISM: human

<400> SEQUENCE: 10

```
Pro Ser Leu Ile Lys Gln Gln Val Leu Lys Asn Val Arg Ile Asp Pro
1               5                   10                  15

Ser Ser Leu Ser Phe Asn Met Trp Lys Glu Ile Pro Ile Pro Phe Tyr
                20                  25                  30

Leu Ser Val Tyr Phe Phe Asp Val Met Asn Pro Ser Glu Ile Leu Lys
            35                  40                  45

Gly Glu Lys Pro Gln Val Arg Glu Arg Gly Pro Tyr Val Tyr Arg Glu
        50                  55                  60

Phe Arg His Lys Ser Asn Ile Thr Phe Asn Asn Asn Asp Thr Val Ser
65                  70                  75                  80

Phe Leu Glu Tyr Arg Thr Phe Gln Phe Gln Pro Ser Lys Ser His Gly
                85                  90                  95

Ser Glu Ser Asp Tyr Ile Val Met Pro Asn Ile Leu Val Leu Gly Ala
                100                 105                 110

Ala Val Met Met Glu Asn Lys Pro Met Thr Leu Lys Leu Ile Met Thr
            115                 120                 125

Leu Ala Phe Thr Thr Leu Gly Glu Arg Ala Phe Met Asn Arg Thr Val
```

```
                130               135               140
Gly Glu Ile Met Trp Gly Tyr Lys Asp Pro Leu Val Asn Leu Ile Asn
145                 150                 155                 160

Lys Tyr Phe Pro Gly Met Phe Pro Phe Lys Asp Lys Phe Gly Leu Phe
                165                 170                 175

Ala Glu Leu Asn Asn Ser Asp Ser Gly Leu Phe Thr Val Phe Thr Gly
                180                 185                 190

Val Gln Asn Ile Ser Arg Ile His Leu Val Asp Lys Trp Asn Gly Leu
                195                 200                 205

Ser Lys Val Asp Phe Trp His Ser Asp Gln Cys Asn Met Ile Asn Gly
            210                 215                 220

Thr Ser Gly Gln Met Trp Pro Pro Phe Met Thr Pro Glu Ser Ser Leu
225                 230                 235                 240

Glu Phe Tyr Ser Pro Glu Ala Cys Arg Ser Met Lys Leu Met Tyr Lys
                245                 250                 255

Glu Ser Gly Val Phe Glu Gly Ile Pro Thr Tyr Arg Phe Val Ala Pro
                260                 265                 270

Lys Thr Leu Phe Ala Asn Gly Ser Ile Tyr Pro Pro Asn Glu Gly Phe
            275                 280                 285

Cys Pro Cys Leu Glu Ser Gly Ile Gln Asn Val Ser Thr Cys Arg Phe
            290                 295                 300

Ser Ala Pro Leu Phe Leu Ser His Pro His Phe Leu Asn Ala Asp Pro
305                 310                 315                 320

Val Leu Ala Glu Ala Val Thr Gly Leu His Pro Asn Gln Glu Ala His
                325                 330                 335

Ser Leu Phe Leu Asp Ile His Pro Val Thr Gly Ile Pro Met Asn Cys
                340                 345                 350

Ser Val Lys Leu Gln Leu Ser Leu Tyr Met Lys Ser Val Ala Gly Ile
            355                 360                 365

Gly Gln Thr Gly Lys Ile Glu Pro Val Val Leu Pro Leu Leu Trp Phe
            370                 375                 380

Ala Glu Ser Gly Ala Met Glu Gly Glu Thr Leu His Thr Phe Tyr Thr
385                 390                 395                 400

Gln Leu Val Leu Met Pro Lys Val Met His Tyr
                405                 410

<210> SEQ ID NO 11
<211> LENGTH: 552
<212> TYPE: PRT
<213> ORGANISM: human

<400> SEQUENCE: 11

Met Gly Cys Ser Ala Lys Ala Arg Trp Ala Gly Ala Leu Gly Val
1               5                   10                  15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
            35                  40                  45

Ser Ser Leu Ser Phe Asn Met Trp Lys Glu Ile Pro Ile Pro Phe Tyr
        50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95
```

```
Phe Arg His Lys Ser Asn Ile Thr Phe Asn Asn Asp Thr Val Ser
            100                 105                 110

Phe Leu Glu Tyr Arg Thr Phe Gln Phe Gln Pro Ser Lys Ser His Gly
            115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
        210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
        275                 280                 285

Glu Ser Gly Val Phe Glu Gly Ile Pro Thr Tyr Arg Phe Val Ala Pro
        290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
            340                 345                 350

Val Leu Ala Glu Ala Val Thr Gly Leu His Pro Asn Gln Glu Ala His
        355                 360                 365

Ser Leu Phe Leu Asp Ile His Pro Val Thr Gly Ile Pro Met Asn Cys
        370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
            420                 425                 430

Gln Leu Val Leu Met Pro Lys Val Met His Tyr Ala Gln Tyr Val Leu
        435                 440                 445

Leu Ala Leu Gly Cys Val Leu Leu Val Pro Val Ile Cys Gln Ile
        450                 455                 460

Arg Ser Gln Val Gly Ala Gly Gln Arg Ala Ala Arg Ala Asp Ser His
465                 470                 475                 480

Ser Leu Ala Cys Trp Gly Lys Gly Ala Ser Asp Arg Thr Leu Trp Pro
                485                 490                 495

Thr Ala Ala Trp Ser Pro Pro Ala Ala Val Leu Arg Leu Cys Arg
            500                 505                 510

Ser Gly Ser Gly His Cys Trp Gly Leu Arg Ser Thr Leu Ala Ser Phe
```

```
            515                 520                 525
Ala Cys Arg Val Ala Thr Thr Leu Pro Val Leu Glu Gly Leu Gly Pro
        530                 535                 540

Ser Leu Gly Gly Gly Thr Gly Ser
545                 550

<210> SEQ ID NO 12
<211> LENGTH: 330
<212> TYPE: PRT
<213> ORGANISM: human

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 13
<211> LENGTH: 232
<212> TYPE: PRT
<213> ORGANISM: human

<400> SEQUENCE: 13

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 14
<211> LENGTH: 236
<212> TYPE: PRT
<213> ORGANISM: human

<400> SEQUENCE: 14

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

```
Cys Leu Val Ile Leu Phe Ala Cys Glu Val Ala Ala Gly Ile Trp Gly
                100                 105                 110
Phe Val Asn Lys Asp Gln Ile Ala Lys Asp Val Lys Gln Phe Tyr Asp
            115                 120                 125
Gln Ala Leu Gln Gln Ala Val Val Asp Asp Ala Asn Asn Ala Lys
        130                 135                 140
Ala Val Val Lys Thr Phe His Glu Thr Leu Asp Cys Cys Gly Ser Ser
145                 150                 155                 160
Thr Leu Thr Ala Leu Thr Thr Ser Val Leu Lys Asn Asn Leu Cys Pro
                165                 170                 175
Ser Gly Ser Asn Ile Ile Ser Asn Leu Phe Lys Glu Asp Cys His Gln
            180                 185                 190
Lys Ile Asp Asp Leu Phe Ser Gly Lys Leu Tyr Leu Ile Gly Ile Ala
        195                 200                 205
Ala Ile Val Val Ala Val Ile Met Ile Phe Glu Met Ile Leu Ser Met
210                 215                 220
Val Leu Cys Cys Gly Ile Arg Asn Ser Ser Val Tyr
225                 230                 235
```

<210> SEQ ID NO 15
<211> LENGTH: 89
<212> TYPE: PRT
<213> ORGANISM: human

<400> SEQUENCE: 15

```
Phe Val Asn Lys Asp Gln Ile Ala Lys Asp Val Lys Gln Phe Tyr Asp
1               5                   10                  15
Gln Ala Leu Gln Gln Ala Val Val Asp Asp Ala Asn Asn Ala Lys
        20                  25                  30
Ala Val Val Lys Thr Phe His Glu Thr Leu Asp Cys Cys Gly Ser Ser
            35                  40                  45
Thr Leu Thr Ala Leu Thr Thr Ser Val Leu Lys Asn Asn Leu Cys Pro
50                  55                  60
Ser Gly Ser Asn Ile Ile Ser Asn Leu Phe Lys Glu Asp Cys His Gln
65                  70                  75                  80
Lys Ile Asp Asp Leu Phe Ser Gly Lys
                85
```

<210> SEQ ID NO 16
<211> LENGTH: 14327
<212> TYPE: DNA
<213> ORGANISM: human

<400> SEQUENCE: 16

| | | |
|---|---|---|
| ggccggcgag cgggcggctg cgggcggcgc ggagcgggcg cgcggagcg agcgagcgag | 60 |
| agagcggcgc gggccgggcc atggggtggc gggcgccggg cgcgctgctg ctggcgctgc | 120 |
| tgctgcacgg gcggctgctg gcggtgaccc atgggctgag gcatacgat ggcttgtctc | 180 |
| tgcctgagga catagagacc gtcacagcaa gccaaatgcg ctggacacat cgtacctttt | 240 |
| ctgatgatga gtacatgctg ctgacagca tctcaggaga cgacctgggc agtggggacc | 300 |
| tgggcagcgg ggacttccag atggtttatt tccgagccct ggtgaattc actcgctcca | 360 |
| tcgagtacag ccctcagctg gaggatgcag gctccagaga gtttcgagag gtgtccgagg | 420 |
| ctgtggtaga cacgctggag tcggagtact gaaaattcc cggagaccag ttgtcagtg | 480 |
| tggtgttcat caaggagctg gatggctggg tttttgtgga gctcgatgtg ggctcggaag | 540 |

```
ggaatgcgga tggtgctcag attcaggaga tgctgctcag ggtcatctcc agcggctctg        600
tggcctccta cgtcacctct ccccagggat tccagttccg acgcctgggc acagtgcccc        660
agttcccaag agcctgcacg gaggccgagt ttgcctgcca cagctacaat gagtgtgtgg        720
ccctggagta tcgctgtgac cggcggcccg actgcaggga catgtctgat gagctcaatt        780
gtgaggagcc agtcctgggt atcagcccca cattctctct ccttgtggag acgacatctt        840
taccgccccg gccagagaca accatcatgc gacagccacc agtcacccac gctcctcagc        900
ccctgcttcc cggttccgtc aggcccctgc cctgtgggcc ccaggaggcc gcatgccgca        960
atgggcactg catccccaga gactacctct cgacggaca ggaggactgc gaggacggca       1020
gcgatgagct agactgtggc cccccgccac cctgtgagcc caacgagttc ccctgcggga       1080
atggacattg tgccctcaag ctgtggcgct gcgatggtga ctttgactgt gaggaccgaa       1140
ctgatgaagc caactgcccc accaagcgtc ctgaggaagt gtgcgggccc acacagttcc       1200
gatgcgtctc taccaacatg tgcatcccag ccagcttcca ctgtgacgag agagcgact       1260 gtcctgaccg gagcgacgag tttggctgca tgcccccca ggtggtgaca cctccccggg       1320
agtccatcca ggcttcccgg ggccagacag tgaccttcac ctgcgtggcc attggcgtcc       1380 ccaccccat catcaattgg aggctcaact ggggccacat cccctctcat cccagggtga       1440
cagtgaccag cgagggtggc cgtggcacac tgatcatccg tgatgtgaag gagtcagacc       1500
agggtgccta cacctgtgag gccatgaacg cccggggcat ggtgtttggc attcctgacg       1560
gtgtccttga gctcgtccca caacgaggcc cctgccctga cggccacttc tacctggagc       1620
acagcgccgc ctgcctgccc tgcttctgct ttggcatcac cagcgtgtgc cagagcaccc       1680
gccgcttccg ggaccagatc aggctgcgct tgaccaacc cgatgacttc aagggtgtga       1740
atgtgacaat gcctgcgcag cccggcacgc caccctctc ctccacgcag ctgcagatcg       1800
acccatccct gcacgagttc agctagtag acctgtcccg ccgcttcctc gtccacgact       1860
ccttctgggc tctgcctgaa cagttcctgg caacaaggt ggactccat ggcggctccc       1920 tgcgttacaa cgtgcgctac gagttggccc gtggcatgct ggagccagtg cagcggccgg       1980
acgtggtcct cgtgggtgcc gggtaccgcc tcctctcccg aggccacaca cccacccaac       2040
ctggtgctct gaaccagcgc caggtccagt tctctgagga gcactgggtc catgagtctg       2100
gccggccggt gcagcgcgcg gagctgctgc aggtgctgca gagcctggag gccgtgctca       2160
tccagaccgt gtacaacacc aagatggcta gcgtgggact tagcgacatc gccatggata       2220
ccaccgtcac cctgccacc agccatggcc gtgcccacag tgtggaggag tgcagatgcc       2280
ccattggcta ttctggcttg tcctgcgaga gctgtgatgc ccacttcact cgggtgcctg       2340
gtgggcccta cctgggcacc tgctctggtt gcagttgcaa tggccatgcc agctcctgtg       2400
accctgtgta tggccactgc ctgaattgcc agcacaacac ggaggggcca cagtgcaaca       2460
agtgcaaggc tggcttcttt ggggacgcca tgaaggccac ggccacttcc tgccggccct       2520
gcccttgccc atacatcgat gcctcccgca gattctcaga cacttgcttc ctggacacgg       2580
atggccaagc cacatgtgac gcctgtgccc caggctacac tggccgccgc tgtgagagct       2640 gtgccccgg atacgagggc aaccccatcc agccgcgg gaagtgcagg cccgtcaacc       2700
aggagattgt gcgctgtgac gagcgtggca gcatgggac ctccggggag gcctgccgct       2760
gtaagaacaa tgtggtgggg cgcttgtgca atgaatgtgc tgacggctct ttccacctga       2820 gtaccccgaaa ccccgatggc tgcctcaagt gcttctgcat gggtgtcagt cgccactgca       2880
ccagctcttc atggagccgt gcccagttgc atggggcctc tgaggagcct ggtcacttca       2940
```

```
gcctgaccaa cgccgcaagc acccacacca ccaacgaggg catcttctcc cccacgcccg   3000
gggaactggg attctcctcc ttccacagac tcttatctgg accctacttc tggagcctcc   3060
cttcacgctt cctggggggac aaggtgacct cctatggagg agagctgcgc ttcacagtga   3120
cccagaggtc ccagccgggc tccacacccc tgcacgggca gccgttggtg gtgctgcaag   3180
gtaacaacat catcctagag caccatgtgg cccaggagcc cagccccggc cagcccagca   3240
ccttcattgt gcctttccgg gagcaagcat ggcagcggcc cgatgggcag ccagccacac   3300
gggagcacct gctgatggca ctggcaggca tcgacaccct cctgatccga gcatcctacg   3360
cccagcagcc cgctgagagc agggtctctg gcatcagcat ggacgtggct gtgcccgagg   3420
aaaccggcca ggaccccgcg ctggaagtgg aacagtgctc ctgcccaccc gggtaccgtg   3480
ggccgtcctg ccaggactgt gacacaggct acacacgcac gcccagtggc ctctacctgg   3540
gtacctgtga acgctgcagc tgccatggcc actcagaggc ctgcgagcca gaaacaggtg   3600
cctgccaggg ctgccagcat cacacggagg ccctcggtg tgagcagtgc cagccaggat   3660
actacgggga cgcccagcgg gggacaccac aggactgcca gctgtgcccc tgctacggag   3720
accctgctgc cggccaggct gcccacactt gttttctgga cacagacggc caccccacct   3780
gtgatgcgtg ctccccaggc cacagtgggc gtcactgtga gaggtgcgcc cctggctact   3840
atggcaaccc cagccagggc cagccatgcc agagagacag ccaggtgcca gggcccatag   3900
gctgcaactg tgacccccaa ggcagcgtca gcagccagtg tgatgctgct ggtcagtgcc   3960
agtgcaaggc ccaggtagaa ggcctcactt gcagccactg ccggcccac cacttccacc   4020 tgagtgccag caacccagac ggctgcctgc cctgcttctg tatgggcatc acccagcagt   4080
gcgccagctc tgcctacaca cgccaccgtga tctccaccca ctttgcccct ggggacttcc   4140
aaggctttgc cctggtgaac ccacagcgaa acagccgcct gacaggagaa ttcactgtgg   4200
aacccgtgcc cgagggtgcc cagctctctt ttggcaactt tgcccaactc ggccatgagt   4260
ccttctactg gcagctgccg gagacatacc agggagacaa ggtggcggcc tacggtggga   4320
agttgcgata caccctctcc tacacagcag gcccacaggg cagcccactc tcggaccccg   4380
atgtgcagat cacgggcaac aacatcatgc tagtggcctc ccagcagcg ctgcagggcc   4440 cagagaggag gagctacgag atcatgttcc gagaggaatt ctggcgccgg cccgatgggc   4500
agccggccac acgcgagcac ctcctgatgg cactggccga cctggatgag ctcctgatcc   4560
gggccacgtt ctcctccgtg ccgctggtgg ccagcatcag cgcagtcagc ctggaggtcg   4620
cccagccggg gccctcaaac agaccccgcg ccctcgaggt ggaggagtgc cgctgcccgc   4680
caggctacat cggtctgtcc tgccaggact gtgccccgg ctacacgcgc accgggagtg   4740
ggctctacct cggccactgc gagctatgtg aatgcaatgg ccactcagac ctgtgccacc   4800
cagagactgg ggcctgctcg caatgccagc acaacgccgc aggggagttc tgcgagcttt   4860
gtgcccctgg ctactacgga gatgccacag ccggacgcc tgaggactgc agccctgtg    4920 cctgcccact gaccaaccca gagaacatgt tttcccgcac ctgtgagagc ctgggagccg   4980
gcgggtaccg ctgcacggcc tgcgaacccg gctacactgg ccagtactgt gagcagtgtg   5040
gcccaggtta cgtgggtaac cccagtgtgc aaggggggcca gtgcctgcca gagacaaacc   5100
aagccccact ggtggtcgag gtccatcctg ctcgaagcat agtgcccaa ggtggctccc    5160 actccctgcg gtgtcaggtc agtgggagcc caccccacta cttctattgg tcccgtgagg   5220
atgggcggcc tgtgcccagc ggcacccagc agcgacatca aggctccgag ctccacttcc   5280
```

```
ccagcgtcca gccctcggat gctggggtct acatttgcac ctgccgtaat ctccaccaat    5340
ccaataccag ccgggcagag ctgctggtca ctgaggctcc aagcaagccc atcacagtga    5400
ctgtggagga gcagcggagc cagagcgtgc gccccggagc tgacgtcacc ttcatctgca    5460
cagccaaaag caagtcccca gcctataccc tggtgtggac ccgcctgcac aacgggaaac    5520
tgcccacccg agccatggat ttcaatggca tcctgaccat tcgcaacgtc cagctgagtg    5580
atgcaggcac ctacgtgtgc accggctcca acatgtttgc catggaccag ggcacagcca    5640
ctctacatgt gcaggcctcg ggcaccttgt ccgcccccgt ggtctccatc catccgccac    5700
agctcacagt gcagcccggg caactggcgg agttccgctg cagcgccaca gggagcccca    5760
cgcccaccct cgagtggaca gggggccccg gcggccagct ccctgcgaag gcacaaatcc    5820
acggcggcat cctgcgcctg ccagctgtcg agcccacgga tcaggcccag tacttgtgcc    5880
gagcccacag cagcgctggg cagcaggtgg ccagggctgt gctccacgtg catggggcg    5940
gtgggcccag agtccaagtg agcccagaga gacccaggt ccacgcaggc cggaccgtca    6000
ggctgtactg cagggctgca ggcgtgccta gcgccaccat cacctggagg aaggaagggg    6060
gcagcctccc accacaggcc cggtcagagc gcacagacat cgcgacactg ctcatcccag    6120
ccatcacgac tgctgacgcc ggcttctacc tctgcgtggc caccagccct gcaggcactg    6180
cccaggcccg gatgcaagtg gttgtccttt cagcctcaga tgccagccca ccggggtca    6240
agattgagtc ctcatcgcct tctgtgacag aagggcaaac actcgacctc aactgtgtgg    6300
tggcagggtc agcccatgcc caggtcacct ggtacaggcg aggggtagc ctgcctcccc    6360
acacccaggt gcacggctcc cgtctgcggc tcccccaggt ctcaccagct gattctggag    6420
aatatgtgtg ccgtgtggag aatggatcgg gccccaagga ggcctccatt actgtgtctg    6480
tgctccacgg cacccattct ggccccagct acacccagt gcccggcagc acccggccca    6540
tccgcatcga gccctcctcc tcacacgtgg cggaagggca gaccctggat ctgaactgcg    6600
tggtgccggg gcaggcccac gcccaggtca cgtggcacaa gcgtggggc agcctccctg    6660
cccggcacca gaccccacggc tcgctgctgc ggctgcacca ggtgaccccg gccgactcag    6720
gcgagtatgt gtgccatgtg gtgggcacct ccggccccct agaggcctca gtcctggtca    6780
ccatcgaagc ctctgtcatc cctggaccca tcccacctgt caggatcgag tcttcatcct    6840
ccacagtggc cgagggccag accctggatc tgagctgcgt ggtggcaggg caggcccacg    6900
cccaggtcac atggtacaag cgtgggggca gcctccctgc ccggcaccag gttcgtggct    6960
cccgcctgta catcttccag gcctcacctg ccgatgcggg acagtacgtc tgccgggcca    7020
gcaacggcat ggaggcctcc atcacggtca cagtaactgg gacccagggg gccaacttag    7080
cctaccctgc cggcagcacc cagcccatcc gcatcgagcc ctcctcctcg caagtggcgg    7140
aagggcagac cctggatctg aactgcgtgg tgccgggca gtcccatgcc caggtcacgt    7200
ggcacaagcg tggggcagc ctccctgtcc ggcaccagac ccacggctcc ctgctgagac    7260
tctaccaagc gtcccccgcc gactcgggcg agtacgtgtg ccgagtgttg gcagctccg    7320
tgcctctaga ggcctctgtc ctggtcacca ttgagcctgc gggctcagtg cctgcacttg    7380
gggtcacccc cacggtccgg atcgagtcat cgtcttcgca agtggccgag gggcagaccc    7440
tggacctgaa ctgcctcgtt gctggtcagg cccatgccca ggtcacgtgg cacaagcgcg    7500
ggggcagcct cccggcccgg caccaggtgc atggctcgag ctacgcctg ctccaggtga    7560
ccccagctga ttcaggggag tacgtgtgcc gtgtggtcgg cagctcaggt acccaggaag    7620
cctcagtcct tgtcaccatc agcagcgcc ttagtggctc ccactcccag ggtgtggcgt    7680
```

```
acccgtccg catcgagtcc tcctcagcct ccctggccaa tggacacacc ctggacctca   7740
actgcctggt tgccagccag gctccccaca ccatcacctg gtataagcgt ggaggcagct   7800
tacccagccg gcaccagatc gtgggctccc ggctgcggat ccctcaggtg actccggcag   7860
actcgggcga gtacgtgtgt cacgtcagta acggtgcagg ctcccgggag acctcgctca   7920
tcgtcaccat ccagggcagc ggttcctccc acgtgcccag cgtctcccca ccgatcagga   7980
tcgagtcgtc ttcccccacg gtggtggaag ggcagacctt ggatctgaac tgcgtggtcg   8040
ccaggcagcc ccaggctatc atcacatggt acaagcgtgg gggcagcctt ccctcccgac   8100
accagaccca tggctcccac ctgcggttgc accaaatgtc tgtggctgac tcgggcgagt   8160
atgtgtgccg ggccaacaac aacatcgatg ccctggaggc ctccatcgtc atctccgtct   8220
cccctagcgc cggcagcccc tccgcccctg gcagctccat gcccatcaga attgagtcat   8280
cctcctcaca cgtggccgaa ggggagaccc tggatctgaa ctgcgtggtc cccgggcagg   8340
cccatgccca ggtcacttgg cacaagcgtg ggggcagcct ccccagtcac catcagaccc   8400
gcggctcacg gctgcggctg caccatgtgt ccccggccga ctcgggtgaa tacgtgtgcc   8460
gggtgatggg cagctctggc cccctggagg cctcagtcct ggtcaccatc gaagcctctg   8520
gctcaagtgc tgtccacgtc cccgcccag gtggagcccc acccatccgc atcgagccct   8580
cctcctcccg agtggcagaa gggcagaccc tggatctgaa gtgcgtggtg cccgggcagg   8640
cccacgccca ggtcacatgg cacaagcgtg gaggaaacct ccctgcccgg caccaggtcc   8700
acggcccact gctgaggctg aaccaggtgt ccccggctga ctctggcgag tactcgtgcc   8760
aagtgaccgg aagctcaggc accctggagg catctgtcct ggtcacaatt gagccctcca   8820
gcccaggacc cattcctgct ccaggactgg cccagcccat ctacatcgag gcctcctctt   8880
cacacgtgac tgaagggcag actctggatc tgaactgtgt ggtgcccggg caggcccatg   8940
cccaggtcac gtggtacaag cgcgggggca gcctccccgc ccggcaccag acccatggct   9000
cccagctgcg gctccacctc gtctcccctg ccgactcagg cgagtatgtg tgtcgtgcag   9060
ccagcggccc aggccctgag caagaagcct ccttcacagt caccgtcccg cccagtgagg   9120
ggtcttccta ccgccttagg agcccggtca tctccatcga cccgcccagc agcaccgtgc   9180
agcagggcca ggatgccagc ttcaagtgcc tcatccatga cggggcagcc cccatcagcc   9240
tcgagtggaa gacccggaac caggagctgg aggacaacgt ccacatcagt cccaatggct   9300
ccatcatcac catcgtgggc acccggccca gcaaccacgg tacctaccgc tgcgtggcct   9360
ccaatgccta cggtgtggcc cagagtgtgg tgaacctcag tgtgcacggg cccctacag   9420 tgtccgtgct ccccgagggc cccgtgtggg tgaaagtggg aaaggctgtc accctggagt   9480
gtgtcagtgc cggggagccc cgctcctctg ctcgttggac ccggatcagc agcaccctg   9540 ccaagttgga gcagcggaca tatgggctca tggacagcca cgcggtgctg cagatttcat   9600
cagctaaacc atcagatgcg ggcacttatg tgtgccttgc tcagaatgca ctaggcacag   9660
cacagaagca ggtggaggtg atcgtggaca cgggcgccat ggcccagggg gcccctcagg   9720
tccaagctga agaagctgag ctgactgtgg aggctggaca cacggccacc ttgcgctgct   9780
cagccacagg cagcccgcg cccaccatcc actggtccaa gctgcgttcc ccactgcct   9840 ggcagcaccg gctggaaggt gacacactca tcatacccg ggtagcccag caggactcgg   9900
gccagtacat ctgcaatgcc actagcctg ctgggcacgc tgaggccacc atcatcctgc   9960
acgtggagag cccaccatat gccaccacgg tcccagcagca cgcttcggtg caggcagggg   10020
```

```
agacggtgca gctccagtgc ctggctcacg ggacaccccc actcaccttc cagtggagcc   10080
gcgtgggcag cagccttcct gggagggcga ccgccaggaa cgagctgctg cactttgagc   10140
gtgcagcccc tgaggactca ggccgctacc gctgccgggt caccaacaag gtgggctcag   10200
ccgaggcctt tgcccagctg ctcgtccaag gccctcccgg ctctctccct gccacctcca   10260
tcccagcagg gtccacgccc accgtgcagg tcacgcctca gctagagacc aagagcattg   10320
gggccagcgt tgagttccac tgtgctgtgc ccagcgacca gggtacccag ctccgttggt   10380
tcaaggaagg gggtcagctg cctccgggtc acagcgtgca ggatggggtg ctccgaatcc   10440
agaacttgga ccagagctgc caagggacgt atatatgcca ggcccatgga ccttggggga   10500
aggcccaggc cagtgcccag ctggttatcc aagccctgcc ctcggtgctc atcaacatcc   10560
ggacctctgt gcagaccgtg gtggttggcc acgccgtgga gttcgaatgc ctggcactgg   10620
gtgaccccaa gcctcaggtg acatggagca agttggagg gcacctgcgg ccaggcattg   10680
tgcagagcgg aggtgtcgtc aggatcgccc acgtagagct ggctgatgcg ggacagtatc   10740
gctgcactgc caccaacgca gctggcacca cacaatccca cgtcctgctg cttgtgcaag   10800
ccttgcccca gatctcaatg ccccaagaag tccgtgtgcc tgctggttct gcagctgtct   10860 tccctgcat agcctcaggc tacccactc ctgacatcag ctggagcaag ctggatggca   10920
gcctgccacc tgacagccgc ctggagaaca catgctgat gctgccctca gtccgacccc   10980
aggacgcagg tacctacgtc tgcaccgcca ctaaccgcca gggcaaggtc aaagcctttg   11040
cccacctgca ggtgccagag cgggtggtgc cctacttcac gcagaccccc tactccttcc   11100
taccgctgcc caccatcaag gatgcctaca ggaagttcga gatcaagatc accttccggc   11160
ccgactcagc cgatgggatg ctgctgtaca tgggcagaa gcgagtccca gggagcccca   11220
ccaacctggc caaccggcag cccgacttca tctccttcgg cctcgtgggg ggaaggcccg   11280
agttccggtt cgatgcaggc tcaggcatgg ccaccatccg ccatcccaca ccactggccc   11340
tgggccattt ccacaccgtg accctgctgc gcagcctcac ccagggctcc ctgattgtgg   11400
gtgacctggc cccggtcaat gggacctccc agggcaagtt ccagggcctg atctgaacg   11460 aggaactcta cctgggtggc tatcctgact atggtgccat ccccaaggcg gggctgagca   11520
gcggcttcat aggctgtgtc cgggagctgc gcatccaggg cgaggagatc gtcttccatg   11580
acctcaacct cacggcgcac ggcatctccc actgccccac ctgtcgggac cggccctgcc   11640
agaatggcgg tcagtgccat gactctgaga gcagcagcta cgtgtgcgtc tgcccagctg   11700
gcttcaccgg gagccgctgt gagcactcgc aggccctgca ctgccatcca gaggcctgtg   11760 ggccccgacgc cacctgtgtg aaccggcctg acggtcgagg ctacacctgc cgctgccacc   11820
tgggccgctc ggggttgcgg tgtgaggaag tgtgacagt gaccaccccc tcgctgtcgg   11880
gtgctggctc ctacctggca ctgcccgccc tcaccaacac acaccacgag ctacgcctgg   11940
acgtggagtt caagccactc gcccctgacg gggtcctgct gttcagcggg gggaagagcg   12000
ggcctgtgga ggacttcgtg tccctggcga tggtgggcgg ccacctggag ttccgctatg   12060
agttggggtc agggctggcc gttctgcgga gcgccgagcc gctggccctg gccgctggc   12120 accgtgtgtc tgcagagcgt ctcaacaagg acggcagcct gcgggtgaat ggtggacgcc   12180
ctgtgctgcg ctcctcgccc ggcaagagcc agggcctcaa cctgcacacc ctgctctacc   12240 tgggggggtgt ggagccttcc gtgccactgt ccccggccac caacatgagc gctcacttcc   12300
gcggctgtgt gggcgaggtg tcagtgaatg gcaaacggct ggacctcacc tacagtttcc   12360
taggcagcca gggcatcggg caatgctatg atagctcccc atgtgagcgc cagccttgcc   12420
```

```
aacatggtgc cacgtgcatg cccgctggcg agtatgagtt ccagtgcctg tgtcgagatg   12480
gattcaaagg agacctgtgt gagcacgagg agaaccctg ccagctccgt gaaccctgtc    12540
tgcatggggg cacctgccag ggcacccgct gcctctgcct ccctggcttc tctggcccac    12600
gctgccaaca aggctctgga catggcatag cagagtccga ctggcatctt gaaggcagcg    12660
ggggcaatga tgcccctggg cagtacggag cctatttcca cgatgatggc ttcctcgcct    12720
tccctggcca tgtcttctcc aggagcctgc ccgaggtgcc cgagaccatc gagctggagg    12780
ttcggaccag cacagccagt ggcctcctgc tctggcaggg tgtggaggtg ggagaggccg    12840
gccaaggcaa ggacttcatc agcctcgggc ttcaagacgg gcaccttgtc ttcaggtacc    12900
agctgggtag tggggaggcc cgcctggtct ctgaggaccc catcaatgac ggcgagtggc    12960
accgggtgac agcactgcgg gagggccgca gaggttccat ccaagtcgac ggtgaggagc    13020
tggtcagcgg ccggtcccca ggtcccaacg tggcagtcaa cgccaagggc agcgtctaca    13080
tcggcggagc ccctgacgtg gccacgctga ccggggggcag attctcctcg ggcatcacag    13140
gctgtgtcaa gaacctggtg ctgcactcgg cccgacccgg cgccccgccc ccacagcccc    13200
tggacctgca gcaccgcgcc caggccgggg ccaacacacg cccctgcccc tcgtaggcac    13260
ctgcctgccc cacacggact cccgggccac gccccagccc gacaatgtcg agtatattat    13320
tattaatatt attatgaatt tttgtaagaa accgaggcga tgccacgctt tgctgctacc    13380
gccctgggct ggactggagg tgggcatgcc accctcacac acacagctgg gcaaagccac    13440
aaggctggcc agcaaggcag gttggatggg agtgggcacc tcagaaagtc accaggactt    13500
ggggtcagga acagtggctg ggtgggccca gaactgcccc cactgtcccc ctacccaccg    13560
atggagcccc cagatagagc tggggtggcct gtttctgcag cccttgggca gttctcactc    13620
ctaggagagc caacctcggc ttgtgggctg gtgccccaca gctacctgag acgggcatcg    13680
caggagtctc tgccacccac tcaggattgg gaattgtctt tagtgccggc tgtggagcaa    13740
aaggcagctc acccctgggc aggcggtccc catcccacc agctcgtttt tcagcacccc    13800
cacccacctc cacccagccc ctggcacctc ctctggcaga ctccccctcc taccacgtcc    13860
tcctggcctg cattcccacc cctcctgcc agcacacagc ctgggtccc tccctcaggg    13920
gctgtaaggg aaggcccacc ccaactctta ccaggagctg ctacaggcag agcccagcac    13980
tgatagggcc ccgcccaccg ggcccgccc accccaggcc acatcccac ccatctgaa    14040
gtgaaggccc agggactcct ccaacagaca acggacggac ggatgccgct ggtgctcagg    14100
aagagctagt gccttaggtg ggggaaggca ggactcacga ctgagagaga gaggagggg    14160
atatgaccac cctgccccat ctgcaggagc ctgaagatcc agctcaagtg ccatcctgcc    14220
agtgccccc agactgtggg gttgggacgc ctggcctctg tgtcctagaa gggaccctcc    14280
tgtggtcttt gtcttgattt ttcttaataa acggtgctat ccccgcc               14327
```

<210> SEQ ID NO 17
<211> LENGTH: 123
<212> TYPE: PRT
<213> ORGANISM: human

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Pro Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Glu His Ser Ile Asp Ser Val
 50                  55                  60

Lys Gly Arg Phe Thr Ile Ser Arg Asp Asn Ser Lys Asn Arg Leu Tyr
65                  70                  75                  80

Leu Gln Met Lys Ser Leu Arg Ala Glu Asp Met Ala Val Tyr Phe Cys
                85                  90                  95

Val Arg Gly Ala His Arg Ser Ser Trp Ser Gly Lys Arg Phe Asp Tyr
            100                 105                 110

Trp Gly Gln Gly Thr Leu Val Thr Ser Ser Ala
            115                 120

<210> SEQ ID NO 18
<211> LENGTH: 65
<212> TYPE: PRT
<213> ORGANISM: human

<400> SEQUENCE: 18

Tyr Leu Ser Asp Asp Glu Asp Met Leu Ala Asp Ser Ile Ser Gly Asp
1               5                   10                  15

Asp Leu Gly Ser Gly Asp Leu Gly Ser Gly Asp Phe Cys Thr Glu Ala
            20                  25                  30

Glu Phe Ala Cys His Ser Tyr Asn Glu Cys Val Ala Leu Glu Tyr Arg
        35                  40                  45

Cys Asp Arg Arg Pro Cys Arg Asp Met Ser Asp Glu Leu Asn Cys
    50                  55                  60

Glu
65

<210> SEQ ID NO 19
<211> LENGTH: 20
<212> TYPE: DNA
<213> ORGANISM: Bacteriophage T7

<400> SEQUENCE: 19
taatacgact cactataggg                                                 20

<210> SEQ ID NO 20
<211> LENGTH: 23
<212> TYPE: PRT
<213> ORGANISM: Homo sapiens

<400> SEQUENCE: 20

Asp Asp Glu Asp Met Ala Asp Ser Ile Ser Gly Asp Asp Leu Gly Ser
1               5                   10                  15

Gly Asp Leu Gly Ser Gly Asp
            20

<210> SEQ ID NO 21
<211> LENGTH: 23
<212> TYPE: PRT
<213> ORGANISM: Homo sapiens

<400> SEQUENCE: 21

Asp Asp Glu Asp Met Ala Asp Ser Ile Thr Gly Asp Asp Leu Gly Thr
1               5                   10                  15

Gly Asp Leu Gly Thr Gly Asp
            20

<210> SEQ ID NO 22
<211> LENGTH: 30
<212> TYPE: PRT
<213> ORGANISM: Homo sapiens

<400> SEQUENCE: 22

Gly Ser Gly Gly Gly Met Val Glu Gln Val Ser Gly Asp Cys Asp Asp
1               5                   10                  15

Glu Asp Gly Cys Gly Gly Ser Gly Ser Gly Glu Val Lys Arg
            20                  25                  30

<210> SEQ ID NO 23
<211> LENGTH: 26
<212> TYPE: PRT
<213> ORGANISM: Homo sapiens

<400> SEQUENCE: 23

Pro Gly Gln Glu Ser Asp Asp Phe Glu Leu Ser Gly Ser Gly Asp Leu
1               5                   10                  15

Asp Asp Leu Glu Asp Ser Met Ile Gly Pro
            20                  25

<210> SEQ ID NO 24
<211> LENGTH: 966
<212> TYPE: DNA
<213> ORGANISM: Artificial Sequence
<220> FEATURE:
<223> OTHER INFORMATION: P6Fc-HS Construct

<400> SEQUENCE: 24
atgtacagga tgcaactcct gtcttgcatt gcactaagtc ttgcacttgt cacgaattcg      60
gaggaacagg ccaagacatt tctggacaag tttaaccacg aagccgaaga cctgttctat     120
cagagctccg gcctggggaa gggcgacttc aggggctcga gtgctgagcc caaatcttgt    180
gacaaaactc acacatgccc accgtgccca gcacctgaac tcctgggggg accgtcagtc    240
ttcctcttcc ccccaaaacc caaggacacc ctcatgatct cccggacccc tgaggtcaca    300
tgcgtggtgg tggacgtgag ccacgaagac cctgaggtca agttcaactg gtacgtggac    360
ggcgtggagg tgcataatgc caagacaaag ccgcgggagg agcagtacaa cagcacgtac    420
cgtgtggtca gcgtcctcac cgtcctgcac caggactggc tgaatggcaa ggagtacaag    480
tgcaaggtct ccaacaaagc cctcccagcc cccatcgaga aaaccatctc caaagccaaa    540
ggcagcccc gagaaccaca ggtgtacacc ctgcccccat cccgggagga gatgaccaag    600
aaccaggtca gcctgacctg cctggtcaaa ggcttctatc ccagcgacat cgccgtggag    660
tgggagagca atgggcagcc ggagaacaac tacaagacca cgcctcccgt gctggactcc    720
gacggctcct tcttcctcta cagcaagctc accgtggaca agagcaggtg gcagcagggg    780
aacgtcttct catgctccgt gatgcatgag gctctgcaca accactacac gcagaagagc    840
ctctcctgt ctccgggtaa agcacgtacg ggcggcggcg cggatccga tgatgagtac    900
atgctggctg acagcatctc aggagacgac ctgggcagtg gggatctcgg atcaggcgac    960
atctag                                                               966

<210> SEQ ID NO 25
<211> LENGTH: 60
<212> TYPE: DNA
<213> ORGANISM: Artificial Sequence
<220> FEATURE:
<223> OTHER INFORMATION: IL-2 Leader

```
<400> SEQUENCE: 25
atgtacagga tgcaactcct gtcttgcatt gcactaagtc ttgcacttgt cacgaattcg         60

<210> SEQ ID NO 26
<211> LENGTH: 93
<212> TYPE: DNA
<213> ORGANISM: Artificial Sequence
<220> FEATURE:
<223> OTHER INFORMATION: ACE2 from P6Fc-HS construct

<400> SEQUENCE: 26
gaggaacagg ccaagacatt tctggacaag tttaaccacg aagccgaaga cctgttctat         60
cagagctccg gcctggggaa gggcgacttc agg                                     93

<210> SEQ ID NO 27
<211> LENGTH: 60
<212> TYPE: DNA
<213> ORGANISM: Artificial Sequence
<220> FEATURE:
<223> OTHER INFORMATION: linker 1 in P6Fc-HS

<400> SEQUENCE: 27
ggctcgagtg ctgagcccaa atcttgtgac aaaactcaca catgcccacc gtgcccagca         60

<210> SEQ ID NO 28
<211> LENGTH: 648
<212> TYPE: DNA
<213> ORGANISM: Artificial Sequence
<220> FEATURE:
<223> OTHER INFORMATION: Fc

<400> SEQUENCE: 28
cctgaactcc tggggggacc gtcagtcttc ctcttccccc caaaacccaa ggacaccctc         60
atgatctccc ggacccctga ggtcacatgc gtggtggtgg acgtgagcca cgaagaccct        120
gaggtcaagt tcaactggta cgtggacggc gtggaggtgc ataatgccaa gacaaagccg        180
cgggaggagc agtacaacag cacgtaccgt gtggtcagcg tcctcaccgt cctgcaccag        240
gactggctga atggcaagga gtacaagtgc aaggtctcca acaaagccct cccagccccc        300
atcgagaaaa ccatctccaa agccaaaggg cagccccgag aaccacaggt gtacaccctg        360
cccccatccc gggaggagat gaccaagaac caggtcagcc tgacctgcct ggtcaaaggc        420
ttctatccca gcgacatcgc cgtggagtgg gagagcaatg ggcagccgga gaacaactac        480
aagaccacgc ctcccgtgct ggactccgac ggctccttct tcctctacag caagctcacc        540
gtggacaaga gcaggtggca gcaggggaac gtcttctcat gctccgtgat gcatgaggct        600
ctgcacaacc actacacgca gaagagcctc tccctgtctc cgggtaaa                    648

<210> SEQ ID NO 29
<211> LENGTH: 27
<212> TYPE: DNA
<213> ORGANISM: Artificial Sequence
<220> FEATURE:
<223> OTHER INFORMATION: linker 2 in P6Fc-HS

<400> SEQUENCE: 29
gcacgtacgg gcggcggcgg cggatcc                                            27

<210> SEQ ID NO 30
<211> LENGTH: 72
<212> TYPE: DNA
```

```
<213> ORGANISM: Artificial Sequence
<220> FEATURE:
<223> OTHER INFORMATION: heparan sulfate

<400> SEQUENCE: 30
gatgatgagt acatgctggc tgacagcatc tcaggagacg acctgggcag tggggatctc      60
ggatcaggcg ac                                                          72

<210> SEQ ID NO 31
<211> LENGTH: 321
<212> TYPE: PRT
<213> ORGANISM: Artificial Sequence
<220> FEATURE:
<223> OTHER INFORMATION: Amino acid sequence of full-length P6Fc-HS
      construct

<400> SEQUENCE: 31
```

Met Tyr Arg Met Gln Leu Leu Ser Cys Ile Ala Leu Ser Leu Ala Leu
1               5                   10                  15

Val Thr Asn Ser Glu Glu Gln Ala Lys Thr Phe Leu Asp Lys Phe Asn
            20                  25                  30

His Glu Ala Glu Asp Leu Phe Tyr Gln Ser Ser Gly Leu Gly Lys Gly
        35                  40                  45

Asp Phe Arg Gly Ser Ser Ala Glu Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys Ala
        275                 280                 285

Arg Thr Gly Gly Gly Gly Ser Asp Asp Glu Tyr Met Leu Ala Asp
    290                 295                 300

Ser Ile Ser Gly Asp Asp Leu Gly Ser Gly Asp Leu Gly Ser Gly Asp

Ile

<210> SEQ ID NO 32
<211> LENGTH: 3066
<212> TYPE: DNA
<213> ORGANISM: Artificial Sequence
<220> FEATURE:
<223> OTHER INFORMATION: Full-length Ace2Fc-HS nucleotide sequence

<400> SEQUENCE: 32

```
atgtacagga tgcaactcct gtcttgcatt gcactaagtc ttgcacttgt cacgaattcg      60
ggctcgaggg ctgctcagtc caccattgag aacaggcca agacattttt ggacaagttt     120
aaccacgaag ccgaagacct gttctatcaa agttcacttg cttcttggaa ttataacacc     180
aatattactg aagagaatgt ccaaaacatg aataatgctg gggacaaatg gtctgccttt     240
ttaaaggaac agtccacact tgcccaaatg tatccactac aagaaattca gaatctcaca     300
gtcaagcttc agctgcaggc tcttcagcaa atgggtcttc agtgctctc agaagacaag      360 agcaaacggt tgaacacaat tctaaataca atgagcacca tctacagtac tggaaaagtt     420
tgtaacccag ataatccaca agaatgctta ttacttgaac caggtttgaa tgaaataatg     480
gcaaacagtt tagactacaa tgagaggctc tgggcttggg aaagctggag atctgaggtc     540
ggcaagcagc tgaggccatt atatgaagag tatgtggtct tgaaaaatga tggcaaga       600 gcaaatcatt atgaggacta tgggattat tggagaggag actatgaagt aaatggggta      660
gatggctatg actacagccg cggccagttg attgaagatg tggaacatac ctttgaagag     720
attaaaccat tatatgaaca tcttcatgcc tatgtgaggg caaagttgat gaatgcctat     780
ccttcctata tcagtccaat tggatgcctc cctgctcatt tgcttggtga tatgtggggt     840 agatttttgga caaatctgta ctctttgaca gttccctttg acagaaaacc aaacatagat     900
gttactgatg caatggtgga ccaggcctgg gatgcacaga gaatattcaa ggaggccgag     960
aagttctttg tatctgttgg tcttcctaat atgactcaag gattctggga aaattccatg    1020
ctaacggacc aggaaatgt tcagaaagca gtctgccatc ccacagcttg ggacctgggg    1080
aagggcgact tcaggatcct tatgtgcaca aaggtgacaa tggacgactt cctgacagct    1140
catcatgaga tggggcatat ccagtatgat atggcatatg ctgcacaacc tttctgcta    1200 agaaatggag ctaatgaagg attccatgaa gctgttgggg aaatcatgtc actttctgca    1260
gccacaccta gcattttaaa atccattggt cttctgtcac ccgatttttca agaagacaat    1320 gaaacagaaa taacttcct gctcaaacaa gcactcacga ttgttgggac tctgccattt    1380
acttacatgt tagagaagtg gaggtggatg gtctttaaag gggaaattcc caaagaccag    1440
tggatgaaaa agtggtggga gatgaagcga gagatagttg gggtggtgga acctgtgccc    1500
catgatgaaa catactgtga ccccgcatct ctgttccatg tttctaatga ttactcattc    1560
attcgatatt acacaaggac cctttaccaa ttccagtttc aagaagcact tgtcaagca    1620 gctaaacatg aaggccctct gcacaaatgt gacatctcaa actctacaga agctggacag    1680
aaactgttca atatgctgag gcttggaaaa tcagaaccct ggaccctagc attgaaaat    1740 gttgtaggag caagaacat gaatgtaagg ccactgctca actactttga gcccttattt    1800
acctggctga agaccagaa caagaattct tttgtgggat ggagtaccga ctggagtcca    1860
tatgcagacc aaagcataa agtgaggata agcctaaaat cagctctttgg agataaagca    1920 tatgaatgga acgacaatga aatgtacctg ttccgatcat ctgttgcata tgctatgagg    1980
```

```
cagtacttttt taaaagtaaa aaatcagatg attcttttg gggaggagga tgtgcgagtg    2040
gctaatttga aaccaagaat ctcctttaat ttctttgtca ctgcacctaa aaatgtgtct    2100
gatatcattc ctagaactga agttgaaaag gccatcagga tgtcccggag ccgtatcaat    2160
gatgctttcc gtctgaatga caacagccta gagtttctgg ggatacagcc aacacttgga    2220
cctcctaacc agccccctgt ttccgggccc tcgggctcga gtgctgagcc caaatcttgt    2280
gacaaaactc acacatgccc accgtgccca gcacctgaac tcctgggggg accgtcagtc    2340
ttcctcttcc ccccaaaacc caaggacacc ctcatgatct cccggacccc tgaggtcaca    2400
tgcgtggtgg tggacgtgag ccacgaagac cctgaggtca agttcaactg gtacgtggac    2460
ggcgtggagg tgcataatgc caagacaaag ccgcgggagg agcagtacaa cagcacgtac    2520
cgtgtggtca gcgtcctcac cgtcctgcac caggactggc tgaatggcaa ggagtacaag    2580
tgcaaggtct ccaacaaagc cctcccagcc cccatcgaga aaaccatctc caaagccaaa    2640
gggcagcccc gagaaccaca ggtgtacacc ctgcccccat cccgggagga gatgaccaag    2700
aaccaggtca gcctgacctg cctggtcaaa ggcttctatc ccagcgacat cgccgtggag    2760
tgggagagca atgggcagcc ggagaacaac tacaagacca cgcctcccgt gctggactcc    2820
gacggctcct tcttcctcta cagcaagctc accgtggaca agagcaggtg gcagcagggg    2880
aacgtcttct catgctccgt gatgcatgag gctctgcaca accactacac gcagaagagc    2940
ctctccctgt ctccgggtaa agcacgtacg gcggcggcg gcggatccga tgatgagtac    3000
atgctggctg acagcatctc aggagacgac ctgggcagtg gggatctcgg atcaggcgac    3060
atctag                                                                3066
```

```
<210> SEQ ID NO 33
<211> LENGTH: 9
<212> TYPE: DNA
<213> ORGANISM: Artificial Sequence
<220> FEATURE:
<223> OTHER INFORMATION: linker 1 in Ace2Fc-HS

<400> SEQUENCE: 33 ggctcgagg                                                                    9

<210> SEQ ID NO 34
<211> LENGTH: 2175
<212> TYPE: DNA
<213> ORGANISM: Artificial Sequence
<220> FEATURE:
<223> OTHER INFORMATION: ACE2 in Ace2Fc-HS

<400> SEQUENCE: 34
gctgctcagt ccaccattga ggaacaggcc aagacatttt tggacaagtt taaccacgaa      60
gccgaagacc tgttctatca aagttcactt gcttcttgga attataacac caatattact     120
gaagagaatg tccaaaacat gaataatgct ggggacaaat ggtctgcctt ttaaaggaa      180 cagtccacac ttgcccaaat gtatccacta caagaaattc agaatctcac agtcaagctt     240
cagctgcagg ctcttcagca aaatgggtct tcagtgctct cagaagacaa gagcaaacgg     300
ttgaacacaa ttctaaatac aatgagcacc atctacagta ctggaaaagt ttgtaaccca     360
gataatccac aagaatgctt attacttgaa ccaggtttga atgaaataat ggcaaacagt     420
ttagactaca atgagaggct ctgggcttgg gaaagctgga gatctgaggt cggcaagcag     480
ctgaggccat tatatgaaga gtatgtggtc ttgaaaaatg agatggcaag agcaaatcat     540
```

```
tatgaggact atgggatta ttggagagga gactatgaag taaatggggt agatggctat      600
gactacagcc gcggccagtt gattgaagat gtggaacata cctttgaaga gattaaacca      660
ttatatgaac atcttcatgc ctatgtgagg gcaaagttga tgaatgccta tccttcctat      720
atcagtccaa ttggatgcct ccctgctcat ttgcttggtg atatgtgggg tagattttgg      780
acaaatctgt actctttgac agttcccttt ggacagaaac caaacataga tgttactgat      840
gcaatggtgg accaggcctg ggatgcacag agaatattca aggaggccga gaagttcttt      900
gtatctgttg gtcttcctaa tatgactcaa ggattctggg aaaattccat gctaacggac      960
ccaggaaatg ttcagaaagc agtctgccat cccacagctt gggacctggg aagggcgac      1020 ttcaggatcc ttatgtgcac aaaggtgaca atggacgact cctgacagc tcatcatgag      1080 atggggcata tccagtatga tatggcatat gctgcacaac ctttctgct aagaaatgga      1140 gctaatgaag gattccatga agctgttggg gaaatcatgt cactttctgc agccacacct      1200
aagcatttaa aatccattgg tcttctgtca cccgattttc aagaagacaa tgaaacagaa      1260
ataaacttcc tgctcaaaca agcactcacg attgttggga ctctgccatt tacttacatg      1320
ttagagaagt ggaggtggat ggtctttaaa gggaaattc ccaaagacca gtggatgaaa      1380
aagtggtggg agatgaagcg agagatagtt ggggtggtgg aacctgtgcc ccatgatgaa      1440
acatactgtg accccgcatc tctgttccat gtttctaatg attactcatt cattcgatat      1500
tacacaagga cccttacca attccagttt caagaagcac tttgtcaagc agctaaacat      1560
gaaggccctc tgcacaaatg tgacatctca aactctacag aagctggaca gaaactgttc      1620
aatatgctga ggcttggaaa atcagaaccc tggaccctag cattggaaa tgttgtagga      1680 gcaaagaaca tgaatgtaag gccactgctc aactactttg agcccttatt tacctggctg      1740
aaagaccaga caagaattc ttttgtggga tggagtaccg actggagtcc atatgcagac      1800
caaagcatca agtgaggat aagcctaaaa tcagctcttg gagataaagc atatgaatgg      1860
aacgacaatg aaatgtacct gttccgatca tctgttgcat atgctatgag gcagtacttt      1920
ttaaaagtaa aaatcagat gattcttttt ggggaggagg atgtgcgagt ggctaatttg      1980
aaaccaagaa tctcctttaa tttctttgtc actgcaccta aaaatgtgtc tgatatcatt      2040
cctagaactg aagttgaaaa ggccatcagg atgtcccgga gccgtatcaa tgatgctttc      2100
cgtctgaatg acaacagcct agagtttctg gggatacagc caacacttgg acctcctaac      2160
cagccccctg tttcc                                                        2175

<210> SEQ ID NO 35
<211> LENGTH: 69
<212> TYPE: DNA
<213> ORGANISM: Artificial Sequence
<220> FEATURE:
<223> OTHER INFORMATION: linker 2 in Ace2Fc-HS

<400> SEQUENCE: 35
gggccctcgg gctcgagtgc tgagcccaaa tcttgtgaca aaactcacac atgcccaccg      60
tgcccagca                                                               69

<210> SEQ ID NO 36
<211> LENGTH: 27
<212> TYPE: DNA
<213> ORGANISM: Artificial Sequence
<220> FEATURE:
<223> OTHER INFORMATION: linker 3 in Ace2Fc-HS

<400> SEQUENCE: 36
```

<210> SEQ ID NO 37
<211> LENGTH: 1021
<212> TYPE: PRT
<213> ORGANISM: Artificial Sequence
<220> FEATURE:
<223> OTHER INFORMATION: Amino acid sequence of Ace2Fc-HS

<400> SEQUENCE: 37

```
Met Tyr Arg Met Gln Leu Leu Ser Cys Ile Ala Leu Ser Leu Ala Leu
1               5                   10                  15

Val Thr Asn Ser Gly Ser Arg Ala Ala Gln Ser Thr Ile Glu Glu Gln
            20                  25                  30

Ala Lys Thr Phe Leu Asp Lys Phe Asn His Glu Ala Glu Asp Leu Phe
        35                  40                  45

Tyr Gln Ser Ser Leu Ala Ser Trp Asn Tyr Asn Thr Asn Ile Thr Glu
    50                  55                  60

Glu Asn Val Gln Asn Met Asn Asn Ala Gly Asp Lys Trp Ser Ala Phe
65                  70                  75                  80

Leu Lys Glu Gln Ser Thr Leu Ala Gln Met Tyr Pro Leu Gln Glu Ile
                85                  90                  95

Gln Asn Leu Thr Val Lys Leu Gln Leu Gln Ala Leu Gln Gln Asn Gly
            100                 105                 110

Ser Ser Val Leu Ser Glu Asp Lys Ser Lys Arg Leu Asn Thr Ile Leu
        115                 120                 125

Asn Thr Met Ser Thr Ile Tyr Ser Thr Gly Lys Val Cys Asn Pro Asp
    130                 135                 140

Asn Pro Gln Glu Cys Leu Leu Leu Glu Pro Gly Leu Asn Glu Ile Met
145                 150                 155                 160

Ala Asn Ser Leu Asp Tyr Asn Glu Arg Leu Trp Ala Trp Glu Ser Trp
                165                 170                 175

Arg Ser Glu Val Gly Lys Gln Leu Arg Pro Leu Tyr Glu Glu Tyr Val
            180                 185                 190

Val Leu Lys Asn Glu Met Ala Arg Ala Asn His Tyr Glu Asp Tyr Gly
        195                 200                 205

Asp Tyr Trp Arg Gly Asp Tyr Glu Val Asn Gly Val Asp Gly Tyr Asp
    210                 215                 220

Tyr Ser Arg Gly Gln Leu Ile Glu Asp Val Glu His Thr Phe Glu Glu
225                 230                 235                 240

Ile Lys Pro Leu Tyr Glu His Leu His Ala Tyr Val Arg Ala Lys Leu
                245                 250                 255

Met Asn Ala Tyr Pro Ser Tyr Ile Ser Pro Ile Gly Cys Leu Pro Ala
            260                 265                 270

His Leu Leu Gly Asp Met Trp Gly Arg Phe Trp Thr Asn Leu Tyr Ser
        275                 280                 285

Leu Thr Val Pro Phe Gly Gln Lys Pro Asn Ile Asp Val Thr Asp Ala
    290                 295                 300

Met Val Asp Gln Ala Trp Asp Ala Gln Arg Ile Phe Lys Glu Ala Glu
305                 310                 315                 320

Lys Phe Phe Val Ser Val Gly Leu Pro Asn Met Thr Gln Gly Phe Trp
                325                 330                 335

Glu Asn Ser Met Leu Thr Asp Pro Gly Asn Val Gln Lys Ala Val Cys
            340                 345                 350
```

-continued

His Pro Thr Ala Trp Asp Leu Gly Lys Gly Asp Phe Arg Ile Leu Met
            355                 360                 365

Cys Thr Lys Val Thr Met Asp Asp Phe Leu Thr Ala His His Glu Met
370                 375                 380

Gly His Ile Gln Tyr Asp Met Ala Tyr Ala Ala Gln Pro Phe Leu Leu
385                 390                 395                 400

Arg Asn Gly Ala Asn Glu Gly Phe His Glu Ala Val Gly Glu Ile Met
                405                 410                 415

Ser Leu Ser Ala Ala Thr Pro Lys His Leu Lys Ser Ile Gly Leu Leu
            420                 425                 430

Ser Pro Asp Phe Gln Glu Asp Asn Glu Thr Glu Ile Asn Phe Leu Leu
        435                 440                 445

Lys Gln Ala Leu Thr Ile Val Gly Thr Leu Pro Phe Thr Tyr Met Leu
450                 455                 460

Glu Lys Trp Arg Trp Met Val Phe Lys Gly Glu Ile Pro Lys Asp Gln
465                 470                 475                 480

Trp Met Lys Lys Trp Trp Glu Met Lys Arg Glu Ile Val Gly Val Val
                485                 490                 495

Glu Pro Val Pro His Asp Glu Thr Tyr Cys Asp Pro Ala Ser Leu Phe
            500                 505                 510

His Val Ser Asn Asp Tyr Ser Phe Ile Arg Tyr Tyr Thr Arg Thr Leu
        515                 520                 525

Tyr Gln Phe Gln Phe Gln Glu Ala Leu Cys Gln Ala Ala Lys His Glu
        530                 535                 540

Gly Pro Leu His Lys Cys Asp Ile Ser Asn Ser Thr Glu Ala Gly Gln
545                 550                 555                 560

Lys Leu Phe Asn Met Leu Arg Leu Gly Lys Ser Glu Pro Trp Thr Leu
                565                 570                 575

Ala Leu Glu Asn Val Val Gly Ala Lys Asn Met Asn Val Arg Pro Leu
            580                 585                 590

Leu Asn Tyr Phe Glu Pro Leu Phe Thr Trp Leu Lys Asp Gln Asn Lys
        595                 600                 605

Asn Ser Phe Val Gly Trp Ser Thr Asp Trp Ser Pro Tyr Ala Asp Gln
        610                 615                 620

Ser Ile Lys Val Arg Ile Ser Leu Lys Ser Ala Leu Gly Asp Lys Ala
625                 630                 635                 640

Tyr Glu Trp Asn Asp Asn Glu Met Tyr Leu Phe Arg Ser Ser Val Ala
                645                 650                 655

Tyr Ala Met Arg Gln Tyr Phe Leu Lys Val Lys Asn Gln Met Ile Leu
            660                 665                 670

Phe Gly Glu Glu Asp Val Arg Val Ala Asn Leu Lys Pro Arg Ile Ser
        675                 680                 685

Phe Asn Phe Phe Val Thr Ala Pro Lys Asn Val Ser Asp Ile Ile Pro
        690                 695                 700

Arg Thr Glu Val Glu Lys Ala Ile Arg Met Ser Arg Ser Arg Ile Asn
705                 710                 715                 720

Asp Ala Phe Arg Leu Asn Asp Asn Ser Leu Glu Phe Leu Gly Ile Gln
                725                 730                 735

Pro Thr Leu Gly Pro Pro Asn Gln Pro Pro Val Ser Gly Pro Ser Gly
            740                 745                 750

Ser Ser Ala Glu Pro Lys Ser Cys Asp Lys Thr His Thr Cys Pro Pro
        755                 760                 765

Cys Pro Ala Pro Glu Leu Leu Gly Gly Pro Ser Val Phe Leu Phe Pro

```
                    770                 775                 780
Pro Lys Pro Lys Asp Thr Leu Met Ile Ser Arg Thr Pro Glu Val Thr
785                 790                 795                 800

Cys Val Val Asp Val Ser His Glu Asp Pro Glu Val Lys Phe Asn
                805                 810                 815

Trp Tyr Val Asp Gly Val Glu Val His Asn Ala Lys Thr Lys Pro Arg
                820                 825                 830

Glu Glu Gln Tyr Asn Ser Thr Tyr Arg Val Val Ser Val Leu Thr Val
                835                 840                 845

Leu His Gln Asp Trp Leu Asn Gly Lys Glu Tyr Lys Cys Lys Val Ser
                850                 855                 860

Asn Lys Ala Leu Pro Ala Pro Ile Glu Lys Thr Ile Ser Lys Ala Lys
865                 870                 875                 880

Gly Gln Pro Arg Glu Pro Gln Val Tyr Thr Leu Pro Pro Ser Arg Glu
                885                 890                 895

Glu Met Thr Lys Asn Gln Val Ser Leu Thr Cys Leu Val Lys Gly Phe
                900                 905                 910

Tyr Pro Ser Asp Ile Ala Val Glu Trp Glu Ser Asn Gly Gln Pro Glu
                915                 920                 925

Asn Asn Tyr Lys Thr Thr Pro Pro Val Leu Asp Ser Asp Gly Ser Phe
930                 935                 940

Phe Leu Tyr Ser Lys Leu Thr Val Asp Lys Ser Arg Trp Gln Gln Gly
945                 950                 955                 960

Asn Val Phe Ser Cys Ser Val Met His Glu Ala Leu His Asn His Tyr
                965                 970                 975

Thr Gln Lys Ser Leu Ser Leu Ser Pro Gly Lys Ala Arg Thr Gly Gly
                980                 985                 990

Gly Gly Gly Ser Asp Asp Glu Tyr  Met Leu Ala Asp Ser  Ile Ser Gly
                995                 1000                 1005

Asp Asp  Leu Gly Ser Gly Asp  Leu Gly Ser Gly Asp  Ile
     1010                 1015                 1020

<210> SEQ ID NO 38
<211> LENGTH: 1227
<212> TYPE: DNA
<213> ORGANISM: Artificial Sequence
<220> FEATURE:
<223> OTHER INFORMATION: Complete nucleotide sequence of P61Fc-HS

<400> SEQUENCE: 38
atgtacagga tgcaactcct gtcttgcatt gcactaagtc ttgcacttgt cacgaattcg      60
gcagcagctg ctcagtccac cattgaggaa caggccaaga catttttgga caagtttaac     120
cacgaagccg aagacctgtt ctatcaaagt tcacttgctt cttggaatta taacaccaat     180
attactgaag agaatgtcca aacatgaat aatgctgggg acaaatggtc tgccttttta     240
aaggaacagt ccacacttgc ccaaatgtat ccactacaag aaattcagaa tctcacagga     300
ggaggacaag gattctggga aaattccatg ctaacggacc aggaaatgt tcagaaagca     360 gtctgccatc ccacagcttg ggacctgggg aagggcgact caggggggcc ctcgggctcg     420
agtgctgagc ccaaatcttg tgacaaaact cacacatgcc caccgtgccc agcacctgaa     480
ctcctggggg gaccgtcagt cttcctcttc cccccaaaac ccaaggacac cctcatgatc     540
tcccggaccc ctgaggtcac atgcgtggtg gtggacgtga gccacgaaga ccctgaggtc     600
aagttcaact ggtacgtgga cggcgtggag gtgcataatg ccaagacaaa gccgcgggag     660
```

```
gagcagtaca acagcacgta ccgtgtggtc agcgtcctca ccgtcctgca ccaggactgg      720
ctgaatggca aggagtacaa gtgcaaggtc tccaacaaag ccctcccagc ccccatcgag      780
aaaaccatct ccaaagccaa agggcagccc cgagaaccac aggtgtacac cctgcccca      840 tcccgggagg agatgaccaa gaaccaggtc agcctgacct gcctggtcaa aggcttctat      900
cccagcgaca tcgccgtgga gtgggagagc aatgggcagc cggagaacaa ctacaagacc      960
acgcctcccg tgctggactc cgacggctcc ttcttcctct acagcaagct caccgtggac     1020
aagagcaggt ggcagcaggg gaacgtcttc tcatgctccg tgatgcatga ggctctgcac     1080
aaccactaca cgcagaagag cctctccctg tctccgggta aagcacgtac gggcggcggc     1140
ggcggatccg atgatgagta catgctggct gacagcatct caggagacga cctgggcagt     1200
ggggatctcg gatcaggcga catctag                                         1227
```

```
<210> SEQ ID NO 39
<211> LENGTH: 6
<212> TYPE: DNA
<213> ORGANISM: Artificial Sequence
<220> FEATURE:
<223> OTHER INFORMATION: linker 1 in P61Fc-HS

<400> SEQUENCE: 39 gcagca                                                                   6
```

```
<210> SEQ ID NO 40
<211> LENGTH: 231
<212> TYPE: DNA
<213> ORGANISM: Artificial Sequence
<220> FEATURE:
<223> OTHER INFORMATION: ACE2-1 portion in P61Fc-HS

<400> SEQUENCE: 40
gctgctcagt ccaccattga ggaacaggcc aagacatttt tggacaagtt taaccacgaa       60
gccgaagacc tgttctatca aagttcactt gcttcttgga attataacac caatattact      120
gaagagaatg tccaaaacat gaataatgct ggggacaaat ggtctgcctt tttaaaggaa      180
cagtccacac ttgcccaaat gtatccacta caagaaattc agaatctcac a              231
```

```
<210> SEQ ID NO 41
<211> LENGTH: 9
<212> TYPE: DNA
<213> ORGANISM: Artificial Sequence
<220> FEATURE:
<223> OTHER INFORMATION: linker 2 in P61Fc-HS

<400> SEQUENCE: 41 ggaggagga                                                                9
```

```
<210> SEQ ID NO 42
<211> LENGTH: 99
<212> TYPE: DNA
<213> ORGANISM: Artificial Sequence
<220> FEATURE:
<223> OTHER INFORMATION: ACE2-2 portion in P61Fc-HS

<400> SEQUENCE: 42
caaggattct gggaaaattc catgctaacg gacccaggaa atgttcagaa agcagtctgc       60
catcccacag cttgggacct ggggaagggc gacttcagg                              99
```

```
<210> SEQ ID NO 43
<211> LENGTH: 69
```

<212> TYPE: DNA
<213> ORGANISM: Artificial Sequence
<220> FEATURE:
<223> OTHER INFORMATION: linker 3 in P61Fc-HS

<400> SEQUENCE: 43
gggccctcgg gctcgagtgc tgagcccaaa tcttgtgaca aaactcacac atgcccaccg     60
tgcccagca                                                            69

<210> SEQ ID NO 44
<211> LENGTH: 27
<212> TYPE: DNA
<213> ORGANISM: Artificial Sequence
<220> FEATURE:
<223> OTHER INFORMATION: linker 4 in P61Fc-HS

<400> SEQUENCE: 44
gcacgtacgg gcggcggcgg cggatcc                                        27

<210> SEQ ID NO 45
<211> LENGTH: 408
<212> TYPE: PRT
<213> ORGANISM: Artificial Sequence
<220> FEATURE:
<223> OTHER INFORMATION: Amino acid sequence of P61Fc-HS

<400> SEQUENCE: 45

Met Tyr Arg Met Gln Leu Leu Ser Cys Ile Ala Leu Ser Leu Ala Leu
1               5                   10                  15

Val Thr Asn Ser Ala Ala Ala Gln Ser Thr Ile Glu Glu Gln Ala
            20                  25                  30

Lys Thr Phe Leu Asp Lys Phe Asn His Glu Ala Glu Asp Leu Phe Tyr
        35                  40                  45

Gln Ser Ser Leu Ala Ser Trp Asn Tyr Asn Thr Asn Ile Thr Glu Glu
    50                  55                  60

Asn Val Gln Asn Met Asn Asn Ala Gly Asp Lys Trp Ser Ala Phe Leu
65                  70                  75                  80

Lys Glu Gln Ser Thr Leu Ala Gln Met Tyr Pro Leu Gln Glu Ile Gln
                85                  90                  95

Asn Leu Thr Gly Gly Gly Gln Gly Phe Trp Glu Asn Ser Met Leu Thr
            100                 105                 110

Asp Pro Gly Asn Val Gln Lys Ala Val Cys His Pro Thr Ala Trp Asp
        115                 120                 125

Leu Gly Lys Gly Asp Phe Arg Gly Pro Ser Gly Ser Ser Ala Glu Pro
    130                 135                 140

Lys Ser Cys Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro

```
                    245                 250                 255
Ala Pro Ile Glu Lys Thr Ile Ser Lys Ala Lys Gly Gln Pro Arg Glu
                260                 265                 270

Pro Gln Val Tyr Thr Leu Pro Pro Ser Arg Glu Glu Met Thr Lys Asn
            275                 280                 285

Gln Val Ser Leu Thr Cys Leu Val Lys Gly Phe Tyr Pro Ser Asp Ile
        290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
                340                 345                 350

Ser Val Met His Glu Ala Leu His Asn His Tyr Thr Gln Lys Ser Leu
            355                 360                 365

Ser Leu Ser Pro Gly Lys Ala Arg Thr Gly Gly Gly Gly Ser Asp
        370                 375                 380

Asp Glu Tyr Met Leu Ala Asp Ser Ile Ser Gly Asp Asp Leu Gly Ser
385                 390                 395                 400

Gly Asp Leu Gly Ser Gly Asp Ile
                405

<210> SEQ ID NO 46
<211> LENGTH: 3369
<212> TYPE: DNA
<213> ORGANISM: Artificial Sequence
<220> FEATURE:
<223> OTHER INFORMATION: ACE2-Fc-SA DNA sequence

<400> SEQUENCE: 46
atgtacagga tgcaactcct gtcttgcatt gcactaagtc ttgcacttgt cacgaattcg      60
ggctcgaggg ctgctcagtc caccattgag aacaggcca agacatttt ggacaagttt      120 aaccacgaag ccgaagacct gttctatcaa agttcacttg cttcttggaa ttataacacc     180
aatattactg aagagaatgt ccaaaacatg aataatgctg gggacaaatg gtctgccttt     240
ttaaaggaac agtccacact tgcccaaatg tatccactac aagaaattca gaatctcaca     300
gtcaagcttc agctgcaggc tcttcagcaa aatgggtctt cagtgctctc agaagacaag     360
agcaaacggt tgaacacaat tctaaataca atgagcacca tctacagtac tggaaaagtt     420
tgtaacccag ataatccaca agaatgctta ttacttgaac aggtttgaa tgaaataatg     480 gcaaacagtt tagactacaa tgagaggctc tgggcttggg aaagctggag atctgaggtc     540
ggcaagcagc tgaggccatt atatgaagag tatgtggtct tgaaaaatga gatggcaaga     600
gcaaatcatt atgaggacta tgggattat tggagaggag actatgaagt aaatgggta      660 gatggctatg actacagccg cggccagttg attgaagatg tggaacatac ctttgaagag     720
attaaaccat atatgaaca tcttcatgcc tatgtgaggg caaagttgat gaatgcctat     780
ccttcctata tcagtccaat tggatgcctc cctgctcatt tgcttggtga tatgtgggt     840 agattttgga caaatctgta ctcttttaca gttccctttg acagaaaacc aaacatagat     900
gttactgatg caatggtgga ccaggcctgg gatgcacaga atattcaa ggaggccgag      960 aagttctttg tatctgttgg tcttcctaat atgactcaag gattctggga aaattccatg     1020 ctaacgacc aggaaatgt tcagaaagca gtctgccatc ccacagcttg ggacctgggg     1080
aagggcgact tcaggatcct tatgtgcaca aaggtgacaa tggacgactt cctgacagct     1140
```

```
catcatgaga tgggcatat ccagtatgat atggcatatg ctgcacaacc tttctgcta    1200 agaaatggag ctaatgaagg attccatgaa gctgttgggg aaatcatgtc actttctgca   1260
gccacaccta agcatttaaa atccattggt cttctgtcac ccgattttca agaagacaat   1320
gaaacagaaa taaacttcct gctcaaacaa gcactcacga ttgttgggac tctgccattt   1380
acttacatgt tagagaagtg gaggtggatg gtctttaaag gggaaattcc caaagaccag   1440
tggatgaaaa agtggtggga gatgaagcga gagatagttg gggtggtgga acctgtgccc   1500
catgatgaaa catactgtga ccccgcatct ctgttccatg tttctaatga ttactcattc   1560
attcgatatt acacaaggac cctttaccaa ttccagtttc aagaagcact tgtcaagca    1620 gctaaacatg aaggccctct gcacaaatgt gacatctcaa actctacaga agctggacag   1680
aaactgttca atatgctgag gcttggaaaa tcagaaccct ggaccctagc attggaaaat   1740
gttgtaggag caaagaacat gaatgtaagg ccactgctca actactttga gcccttattt   1800
acctggctga agaccagaa caagaattct tttgtgggat ggagtaccga ctggagtcca    1860
tatgcagacc aaagcatcaa agtgaggata agcctaaaat cagctcttgg agataaagca   1920
tatgaatgga acgacaatga aatgtacctg ttccgatcat ctgttgcata tgctatgagg   1980
cagtactttt taaaagtaaa aaatcagatg attcttttg gggaggagga tgtgcgagtg    2040
gctaatttga aaccaagaat ctcctttaat ttctttgtca ctgcacctaa aaatgtgtct   2100
gatatcattc ctagaactga agttgaaaag gccatcagga tgtcccggag ccgtatcaat   2160
gatgctttcc gtctgaatga caacagccta gagtttctgg ggatacagcc aacacttgga   2220
cctcctaacc agcccctgt tccgggccc tcgggctcga gtgctgagcc caaatcttgt      2280
gacaaaactc acacatgccc accgtgccca gcacctgaac tcctgggggg accgtcagtc   2340
ttcctcttcc cccaaaacc caaggacacc ctcatgatct cccggacccc tgaggtcaca    2400
tgcgtggtgg tggacgtgag ccacgaagac cctgaggtca agttcaactg gtacgtggac   2460
ggcgtggagg tgcataatgc caagacaaag ccgcgggagg agcagtacaa cagcacgtac   2520
cgtgtggtca gcgtcctcac cgtcctgcac caggactggc tgaatggcaa ggagtacaag   2580
tgcaaggtct ccaacaaagc cctcccagcc cccatcgaga aaaccatctc caaagccaaa   2640
gggcagcccc gagaaccaca ggtgtacacc ctgcccccat cccgggagga tgaccaag     2700 aaccaggtca gcctgacctg cctggtcaaa ggcttctatc ccagcgacat cgccgtggag   2760
tgggagagca atgggcagcc ggagaacaac tacaagacca cgcctcccgt gctggactcc   2820
gacggctcct tcttcctcta cagcaagctc accgtggaca agagcaggtg gcagcagggg   2880
aacgtcttct catgctccgt gatgcatgag gctctgcaca accactacac gcagaagagc   2940
ctctccctgt ctccgggtaa agcacgtacg ggcggcggcg gcggatccga agctggcata   3000
acaggcacgt ggtacaatca actcgggagc acgtttattg tgacagcagg agcggatgga   3060
gcactgacgg ggacttacga gagtgctgtg ggtaacgccg agtctcgata tgtactgaca   3120
ggcagatacg atagcgcacc ggccaccgac ggttcaggaa cggccctggg ctggaccgtt   3180
gcttggaaga taactacag gaacgcacac agtgcaacta catggtctgg ccagtacgtg    3240
gggggagcgg aagccaggat aaacacgcag tggctcctta ctagcggaac cacagaagcg   3300
aacgcatgga aatctacact ggtggggcat gacacgttta cgaaggtaaa accctctgcg   3360
gctagttag                                                           3369
```

<210> SEQ ID NO 47

<211> LENGTH: 1122
<212> TYPE: PRT
<213> ORGANISM: Artificial Sequence
<220> FEATURE:
<223> OTHER INFORMATION: ACE2-Fc-SA amino acid sequence

<400> SEQUENCE: 47

```
Met Tyr Arg Met Gln Leu Leu Ser Cys Ile Ala Leu Ser Leu Ala Leu
1               5                   10                  15

Val Thr Asn Ser Gly Ser Arg Ala Ala Gln Ser Thr Ile Glu Glu Gln
            20                  25                  30

Ala Lys Thr Phe Leu Asp Lys Phe Asn His Glu Ala Glu Asp Leu Phe
        35                  40                  45

Tyr Gln Ser Ser Leu Ala Ser Trp Asn Tyr Asn Thr Asn Ile Thr Glu
    50                  55                  60

Glu Asn Val Gln Asn Met Asn Asn Ala Gly Asp Lys Trp Ser Ala Phe
65                  70                  75                  80

Leu Lys Glu Gln Ser Thr Leu Ala Gln Met Tyr Pro Leu Gln Glu Ile
                85                  90                  95

Gln Asn Leu Thr Val Lys Leu Gln Leu Gln Ala Leu Gln Gln Asn Gly
            100                 105                 110

Ser Ser Val Leu Ser Glu Asp Lys Ser Lys Arg Leu Asn Thr Ile Leu
        115                 120                 125

Asn Thr Met Ser Thr Ile Tyr Ser Thr Gly Lys Val Cys Asn Pro Asp
    130                 135                 140

Asn Pro Gln Glu Cys Leu Leu Leu Glu Pro Gly Leu Asn Glu Ile Met
145                 150                 155                 160

Ala Asn Ser Leu Asp Tyr Asn Glu Arg Leu Trp Ala Trp Glu Ser Trp
                165                 170                 175

Arg Ser Glu Val Gly Lys Gln Leu Arg Pro Leu Tyr Glu Glu Tyr Val
            180                 185                 190

Val Leu Lys Asn Glu Met Ala Arg Ala Asn His Tyr Glu Asp Tyr Gly
        195                 200                 205

Asp Tyr Trp Arg Gly Asp Tyr Glu Val Asn Gly Val Asp Gly Tyr Asp
    210                 215                 220

Tyr Ser Arg Gly Gln Leu Ile Glu Asp Val Glu His Thr Phe Glu Glu
225                 230                 235                 240

Ile Lys Pro Leu Tyr Glu His Leu His Ala Tyr Val Arg Ala Lys Leu
                245                 250                 255

Met Asn Ala Tyr Pro Ser Tyr Ile Ser Pro Ile Gly Cys Leu Pro Ala
            260                 265                 270

His Leu Leu Gly Asp Met Trp Gly Arg Phe Trp Thr Asn Leu Tyr Ser
        275                 280                 285

Leu Thr Val Pro Phe Gly Gln Lys Pro Asn Ile Asp Val Thr Asp Ala
    290                 295                 300

Met Val Asp Gln Ala Trp Asp Ala Gln Arg Ile Phe Lys Glu Ala Glu
305                 310                 315                 320

Lys Phe Phe Val Ser Val Gly Leu Pro Asn Met Thr Gln Gly Phe Trp
                325                 330                 335

Glu Asn Ser Met Leu Thr Asp Pro Gly Asn Val Gln Lys Ala Val Cys
            340                 345                 350

His Pro Thr Ala Trp Asp Leu Gly Lys Gly Asp Phe Arg Ile Leu Met
        355                 360                 365

Cys Thr Lys Val Thr Met Asp Asp Phe Leu Thr Ala His His Glu Met
    370                 375                 380
```

```
Gly His Ile Gln Tyr Asp Met Ala Tyr Ala Ala Gln Pro Phe Leu Leu
385                 390                 395                 400

Arg Asn Gly Ala Asn Glu Gly Phe His Glu Ala Val Gly Glu Ile Met
                405                 410                 415

Ser Leu Ser Ala Ala Thr Pro Lys His Leu Lys Ser Ile Gly Leu Leu
            420                 425                 430

Ser Pro Asp Phe Gln Glu Asp Asn Glu Thr Glu Ile Asn Phe Leu Leu
        435                 440                 445

Lys Gln Ala Leu Thr Ile Val Gly Thr Leu Pro Phe Thr Tyr Met Leu
    450                 455                 460

Glu Lys Trp Arg Trp Met Val Phe Lys Gly Ile Pro Lys Asp Gln
465                 470                 475                 480

Trp Met Lys Lys Trp Trp Glu Met Lys Arg Glu Ile Val Gly Val Val
                485                 490                 495

Glu Pro Val Pro His Asp Glu Thr Tyr Cys Asp Pro Ala Ser Leu Phe
                500                 505                 510

His Val Ser Asn Asp Tyr Ser Phe Ile Arg Tyr Tyr Thr Arg Thr Leu
            515                 520                 525

Tyr Gln Phe Gln Phe Gln Glu Ala Leu Cys Gln Ala Ala Lys His Glu
    530                 535                 540

Gly Pro Leu His Lys Cys Asp Ile Ser Asn Ser Thr Glu Ala Gly Gln
545                 550                 555                 560

Lys Leu Phe Asn Met Leu Arg Leu Gly Lys Ser Glu Pro Trp Thr Leu
                565                 570                 575

Ala Leu Glu Asn Val Val Gly Ala Lys Asn Met Asn Val Arg Pro Leu
                580                 585                 590

Leu Asn Tyr Phe Glu Pro Leu Phe Thr Trp Leu Lys Asp Gln Asn Lys
            595                 600                 605

Asn Ser Phe Val Gly Trp Ser Thr Asp Trp Ser Pro Tyr Ala Asp Gln
            610                 615                 620

Ser Ile Lys Val Arg Ile Ser Leu Lys Ser Ala Leu Gly Asp Lys Ala
625                 630                 635                 640

Tyr Glu Trp Asn Asp Asn Glu Met Tyr Leu Phe Arg Ser Ser Val Ala
                645                 650                 655

Tyr Ala Met Arg Gln Tyr Phe Leu Lys Val Lys Asn Gln Met Ile Leu
                660                 665                 670

Phe Gly Glu Glu Asp Val Arg Val Ala Asn Leu Lys Pro Arg Ile Ser
            675                 680                 685

Phe Asn Phe Phe Val Thr Ala Pro Lys Asn Val Ser Asp Ile Ile Pro
            690                 695                 700

Arg Thr Glu Val Glu Lys Ala Ile Arg Met Ser Arg Ser Arg Ile Asn
705                 710                 715                 720

Asp Ala Phe Arg Leu Asn Asp Asn Ser Leu Glu Phe Leu Gly Ile Gln
                725                 730                 735

Pro Thr Leu Gly Pro Pro Asn Gln Pro Val Ser Gly Pro Ser Gly
            740                 745                 750

Ser Ser Ala Glu Pro Lys Ser Cys Asp Lys Thr His Thr Cys Pro Pro
        755                 760                 765

Cys Pro Ala Pro Glu Leu Leu Gly Gly Pro Ser Val Phe Leu Phe Pro
        770                 775                 780

Pro Lys Pro Lys Asp Thr Leu Met Ile Ser Arg Thr Pro Glu Val Thr
785                 790                 795                 800
```

| | | | | | | | | | | | |
|---|---|---|---|---|---|---|---|---|---|---|---|
Cys Val Val Val Asp Val Ser His Glu Asp Pro Glu Val Lys Phe Asn
805 810 815

Trp Tyr Val Asp Gly Val Glu Val His Asn Ala Lys Thr Lys Pro Arg
820 825 830

Glu Glu Gln Tyr Asn Ser Thr Tyr Arg Val Val Ser Val Leu Thr Val
835 840 845

Leu His Gln Asp Trp Leu Asn Gly Lys Glu Tyr Lys Cys Lys Val Ser
850 855 860

Asn Lys Ala Leu Pro Ala Pro Ile Glu Lys Thr Ile Ser Lys Ala Lys
865 870 875 880

Gly Gln Pro Arg Glu Pro Gln Val Tyr Thr Leu Pro Pro Ser Arg Glu
885 890 895

Glu Met Thr Lys Asn Gln Val Ser Leu Thr Cys Leu Val Lys Gly Phe
900 905 910

Tyr Pro Ser Asp Ile Ala Val Glu Trp Glu Ser Asn Gly Gln Pro Glu
915 920 925

Asn Asn Tyr Lys Thr Thr Pro Pro Val Leu Asp Ser Asp Gly Ser Phe
930 935 940

Phe Leu Tyr Ser Lys Leu Thr Val Asp Lys Ser Arg Trp Gln Gln Gly
945 950 955 960

Asn Val Phe Ser Cys Ser Val Met His Glu Ala Leu His Asn His Tyr
965 970 975

Thr Gln Lys Ser Leu Ser Leu Ser Pro Gly Lys Ala Arg Thr Gly Gly
980 985 990

Gly Gly Gly Ser Glu Ala Gly Ile Thr Gly Thr Trp Tyr Asn Gln Leu
995 1000 1005

Gly Ser Thr Phe Ile Val Thr Ala Gly Ala Asp Gly Ala Leu Thr
1010 1015 1020

Gly Thr Tyr Glu Ser Ala Val Gly Asn Ala Glu Ser Arg Tyr Val
1025 1030 1035

Leu Thr Gly Arg Tyr Asp Ser Ala Pro Ala Thr Asp Gly Ser Gly
1040 1045 1050

Thr Ala Leu Gly Trp Thr Val Ala Trp Lys Asn Asn Tyr Arg Asn
1055 1060 1065

Ala His Ser Ala Thr Thr Trp Ser Gly Gln Tyr Val Gly Gly Ala
1070 1075 1080

Glu Ala Arg Ile Asn Thr Gln Trp Leu Leu Thr Ser Gly Thr Thr
1085 1090 1095

Glu Ala Asn Ala Trp Lys Ser Thr Leu Val Gly His Asp Thr Phe
1100 1105 1110

Thr Lys Val Lys Pro Ser Ala Ala Ser
1115 1120

<210> SEQ ID NO 48
<211> LENGTH: 3036
<212> TYPE: DNA
<213> ORGANISM: Artificial Sequence
<220> FEATURE:
<223> OTHER INFORMATION: ACE2-Fc-AviTag DNA sequence

<400> SEQUENCE: 48
atgtacagga tgcaactcct gtcttgcatt gcactaagtc ttgcacttgt cacgaattcg      60
ggctcgaggg ctgctcagtc caccattgag aacaggcca agacattttt ggacaagttt     120
aaccacgaag ccgaagacct gttctatcaa agttcacttg cttcttggaa ttataacacc    180

-continued

```
aatattactg aagagaatgt ccaaaacatg aataatgctg gggacaaatg gtctgccttt    240
ttaaaggaac agtccacact tgcccaaatg tatccactac aagaaattca gaatctcaca    300
gtcaagcttc agctgcaggc tcttcagcaa aatgggtctt cagtgctctc agaagacaag    360
agcaaacggt tgaacacaat tctaaataca atgagcacca tctacagtac tggaaaagtt    420
tgtaacccag ataatccaca agaatgctta ttacttgaac caggtttgaa tgaaataatg    480
gcaaacagtt tagactacaa tgagaggctc tgggcttggg aaagctggag atctgaggtc    540
ggcaagcagc tgaggccatt atatgaagag tatgtggtct gaaaaatga gatggcaaga    600 gcaaatcatt atgaggacta tggggattat tggagaggag actatgaagt aaatggggta    660
gatggctatg actacagccg cggccagttg attgaagatg tggaacatac ctttgaagag    720
attaaaccat tatatgaaca tcttcatgcc tatgtgaggg caaagttgat gaatgcctat    780
ccttcctata tcagtccaat ggatgcctc cctgctcatt tgcttggtga tatgtggggt    840
agattttgga caaatctgta ctctttgaca gttcccttt gacagaaacc aaacatagat    900
gttactgatg caatggtgga ccaggcctgg gatgcacaga gaatattcaa ggaggccgag    960
aagttctttg tatctgttgg tcttcctaat atgactcaag gattctggga aaattccatg   1020
ctaacggacc caggaaatgt tcagaaagca gtctgccatc ccacagcttg ggacctgggg   1080
aagggcgact tcaggatcct tatgtgcaca aaggtgacaa tggacgactt cctgacagct   1140
catcatgaga tggggcatat ccagtatgat atggcatatg ctgcacaacc ttttctgcta   1200
agaaatggag ctaatgaagg attccatgaa gctgttgggg aaatcatgtc actttctgca   1260
gccacaccta agcattttaaa atccattggt cttctgtcac ccgattttca agaagacaat   1320
gaaacagaaa taaacttcct gctcaaacaa gcactcacga ttgttgggac tctgccattt   1380
acttacatgt tagagaagtg gaggtggatg gtctttaaag gggaaattcc caaagaccag   1440
tggatgaaaa agtggtggga gatgaagcga gagatagttg gggtggtgga acctgtgccc   1500
catgatgaaa catactgtga ccccgcatct ctgttccatg tttctaatga ttactcattc   1560
attcgatatt acacaaggac cctttaccaa ttccagtttc aagaagcact tgtcaagca   1620 gctaaacatg aaggccctct gcacaaatgt gacatctcaa actctacaga agctggacag   1680
aaactgttca atatgctgag gcttggaaaa tcagaaccct ggaccctagc attggaaaat   1740
gttgtaggag caaagaacat gaatgtaagg ccactgctca actactttga gcccttattt   1800
acctggctga agaccagaa caagaattct tttgtgggat ggagtaccga ctggagtcca   1860
tatgcagacc aaagcatcaa agtgaggata agcctaaaat cagctcttgg agataaagca   1920
tatgaatgga acgacaatga aatgtacctg ttccgatcat ctgttgcata tgctatgagg   1980
cagtactttt taaagtaaa aaatcagatg attctttttg ggaggagga tgtgcgagtg   2040 gctaatttga aaccaagaat ctcctttaat ttctttgtca ctgcacctaa aaatgtgtct   2100
gatatcattc ctagaactga agttgaaaag gccatcagga tgtcccggag ccgtatcaat   2160
gatgctttcc gtctgaatga caacagccta gagtttctgg ggatacagcc aacacttgga   2220
cctcctaacc agcccctgt ttccgggccc tcgggctcga gtgctgagcc caaatcttgt   2280
gacaaaactc acacatgccc accgtgccca gcacctgaac tcctgggggg accgtcagtc   2340
ttcctcttcc ccccaaaacc caaggacacc ctcatgatct cccggacccc tgaggtcaca   2400
tgcgtggtgg tggacgtgag ccacgaagac cctgaggtca agttcaactg gtacgtggac   2460
ggcgtggagg tgcataatgc caagacaaag ccgcgggagg agcagtacaa cagcacgtac   2520
cgtgtggtca gcgtcctcac cgtcctgcac caggactggc tgaatggcaa ggagtacaag   2580
```

-continued

```
tgcaaggtct ccaacaaagc cctcccagcc cccatcgaga aaaccatctc caaagccaaa    2640
gggcagcccc gagaaccaca ggtgtacacc ctgcccccat cccggggagga gatgaccaag    2700 aaccaggtca gcctgacctg cctggtcaaa ggcttctatc ccagcgacat cgccgtggag    2760
tgggagagca atgggcagcc ggagaacaac tacaagacca cgcctcccgt gctggactcc    2820
gacggctcct tcttcctcta cagcaagctc accgtggaca agagcaggtg gcagcagggg    2880
aacgtcttct catgctccgt gatgcatgag gctctgcaca accactacac gcagaagagc    2940
ctctccctgt ctccgggtaa agcacgtacg ggcggcggcg gcggatccgg gctgaatgat    3000
attttcgaag cacagaaaat tgaatggcat gagtag                              3036
```

<210> SEQ ID NO 49
<211> LENGTH: 1011
<212> TYPE: PRT
<213> ORGANISM: Artificial Sequence
<220> FEATURE:
<223> OTHER INFORMATION: ACE2-Fc-AviTag amino acid sequence

<400> SEQUENCE: 49

```
Met Tyr Arg Met Gln Leu Leu Ser Cys Ile Ala Leu Ser Leu Ala Leu
1               5                   10                  15

Val Thr Asn Ser Gly Ser Arg Ala Ala Gln Ser Thr Ile Glu Glu Gln
            20                  25                  30

Ala Lys Thr Phe Leu Asp Lys Phe Asn His Glu Ala Glu Asp Leu Phe
        35                  40                  45

Tyr Gln Ser Ser Leu Ala Ser Trp Asn Tyr Asn Thr Asn Ile Thr Glu
    50                  55                  60

Glu Asn Val Gln Asn Met Asn Asn Ala Gly Asp Lys Trp Ser Ala Phe
65                  70                  75                  80

Leu Lys Glu Gln Ser Thr Leu Ala Gln Met Tyr Pro Leu Gln Glu Ile
                85                  90                  95

Gln Asn Leu Thr Val Lys Leu Gln Leu Gln Ala Leu Gln Gln Asn Gly
            100                 105                 110

Ser Ser Val Leu Ser Glu Asp Lys Ser Lys Arg Leu Asn Thr Ile Leu
        115                 120                 125

Asn Thr Met Ser Thr Ile Tyr Ser Thr Gly Lys Val Cys Asn Pro Asp
    130                 135                 140

Asn Pro Gln Glu Cys Leu Leu Leu Glu Pro Gly Leu Asn Glu Ile Met
145                 150                 155                 160

Ala Asn Ser Leu Asp Tyr Asn Glu Arg Leu Trp Ala Trp Glu Ser Trp
                165                 170                 175

Arg Ser Glu Val Gly Lys Gln Leu Arg Pro Leu Tyr Glu Glu Tyr Val
            180                 185                 190

Val Leu Lys Asn Glu Met Ala Arg Ala Asn His Tyr Glu Asp Tyr Gly
        195                 200                 205

Asp Tyr Trp Arg Gly Asp Tyr Glu Val Asn Gly Val Asp Gly Tyr Asp
    210                 215                 220

Tyr Ser Arg Gly Gln Leu Ile Glu Asp Val Glu His Thr Phe Glu Glu
225                 230                 235                 240

Ile Lys Pro Leu Tyr Glu His Leu His Ala Tyr Val Arg Ala Lys Leu
                245                 250                 255

Met Asn Ala Tyr Pro Ser Tyr Ile Ser Pro Ile Gly Cys Leu Pro Ala
            260                 265                 270

His Leu Leu Gly Asp Met Trp Gly Arg Phe Trp Thr Asn Leu Tyr Ser
```

```
                275                 280                 285
Leu Thr Val Pro Phe Gly Gln Lys Pro Asn Ile Asp Val Thr Asp Ala
            290                 295                 300
Met Val Asp Gln Ala Trp Asp Ala Gln Arg Ile Phe Lys Glu Ala Glu
305                 310                 315                 320
Lys Phe Phe Val Ser Val Gly Leu Pro Asn Met Thr Gln Gly Phe Trp
                325                 330                 335
Glu Asn Ser Met Leu Thr Asp Pro Gly Asn Val Gln Lys Ala Val Cys
            340                 345                 350
His Pro Thr Ala Trp Asp Leu Gly Lys Gly Asp Phe Arg Ile Leu Met
            355                 360                 365
Cys Thr Lys Val Thr Met Asp Asp Phe Leu Thr Ala His His Glu Met
        370                 375                 380
Gly His Ile Gln Tyr Asp Met Ala Tyr Ala Ala Gln Pro Phe Leu Leu
385                 390                 395                 400
Arg Asn Gly Ala Asn Glu Gly Phe His Glu Ala Val Gly Glu Ile Met
                405                 410                 415
Ser Leu Ser Ala Ala Thr Pro Lys His Leu Lys Ser Ile Gly Leu Leu
            420                 425                 430
Ser Pro Asp Phe Gln Glu Asp Asn Glu Thr Glu Ile Asn Phe Leu Leu
        435                 440                 445
Lys Gln Ala Leu Thr Ile Val Gly Thr Leu Pro Phe Thr Tyr Met Leu
450                 455                 460
Glu Lys Trp Arg Trp Met Val Phe Lys Gly Glu Ile Pro Lys Asp Gln
465                 470                 475                 480
Trp Met Lys Lys Trp Trp Glu Met Lys Arg Glu Ile Val Gly Val Val
                485                 490                 495
Glu Pro Val Pro His Asp Glu Thr Tyr Cys Asp Pro Ala Ser Leu Phe
            500                 505                 510
His Val Ser Asn Asp Tyr Ser Phe Ile Arg Tyr Tyr Thr Arg Thr Leu
            515                 520                 525
Tyr Gln Phe Gln Phe Gln Glu Ala Leu Cys Gln Ala Ala Lys His Glu
        530                 535                 540
Gly Pro Leu His Lys Cys Asp Ile Ser Asn Ser Thr Glu Ala Gly Gln
545                 550                 555                 560
Lys Leu Phe Asn Met Leu Arg Leu Gly Lys Ser Glu Pro Trp Thr Leu
                565                 570                 575
Ala Leu Glu Asn Val Val Gly Ala Lys Asn Met Asn Val Arg Pro Leu
            580                 585                 590
Leu Asn Tyr Phe Glu Pro Leu Phe Thr Trp Leu Lys Asp Gln Asn Lys
        595                 600                 605
Asn Ser Phe Val Gly Trp Ser Thr Asp Trp Ser Pro Tyr Ala Asp Gln
        610                 615                 620
Ser Ile Lys Val Arg Ile Ser Leu Lys Ser Ala Leu Gly Asp Lys Ala
625                 630                 635                 640
Tyr Glu Trp Asn Asp Asn Glu Met Tyr Leu Phe Arg Ser Ser Val Ala
                645                 650                 655
Tyr Ala Met Arg Gln Tyr Phe Leu Lys Val Lys Asn Gln Met Ile Leu
            660                 665                 670
Phe Gly Glu Glu Asp Val Arg Val Ala Asn Leu Lys Pro Arg Ile Ser
        675                 680                 685
Phe Asn Phe Phe Val Thr Ala Pro Lys Asn Val Ser Asp Ile Ile Pro
        690                 695                 700
```

| | | | | | | | | | | | |
|---|---|---|---|---|---|---|---|---|---|---|---|
| Arg | Thr | Glu | Val | Glu | Lys | Ala | Ile | Arg | Met | Ser | Arg | Ser | Arg | Ile | Asn |
| 705 | | | | 710 | | | | | 715 | | | | | 720 | |

Arg Thr Glu Val Glu Lys Ala Ile Arg Met Ser Arg Ser Arg Ile Asn
705                 710                 715                 720

Asp Ala Phe Arg Leu Asn Asp Asn Ser Leu Glu Phe Leu Gly Ile Gln
            725                 730                     735

Pro Thr Leu Gly Pro Pro Asn Gln Pro Pro Val Ser Gly Pro Ser Gly
            740                 745                 750

Ser Ser Ala Glu Pro Lys Ser Cys Asp Lys Thr His Thr Cys Pro Pro
            755                 760                 765

Cys Pro Ala Pro Glu Leu Leu Gly Gly Pro Ser Val Phe Leu Phe Pro
770                 775                 780

Pro Lys Pro Lys Asp Thr Leu Met Ile Ser Arg Thr Pro Glu Val Thr
785                 790                 795                 800

Cys Val Val Val Asp Val Ser His Glu Asp Pro Glu Val Lys Phe Asn
                805                 810                 815

Trp Tyr Val Asp Gly Val Glu Val His Asn Ala Lys Thr Lys Pro Arg
            820                 825                 830

Glu Glu Gln Tyr Asn Ser Thr Tyr Arg Val Val Ser Val Leu Thr Val
            835                 840                 845

Leu His Gln Asp Trp Leu Asn Gly Lys Glu Tyr Lys Cys Lys Val Ser
850                 855                 860

Asn Lys Ala Leu Pro Ala Pro Ile Glu Lys Thr Ile Ser Lys Ala Lys
865                 870                 875                 880

Gly Gln Pro Arg Glu Pro Gln Val Tyr Thr Leu Pro Pro Ser Arg Glu
            885                 890                 895

Glu Met Thr Lys Asn Gln Val Ser Leu Thr Cys Leu Val Lys Gly Phe
            900                 905                 910

Tyr Pro Ser Asp Ile Ala Val Glu Trp Glu Ser Asn Gly Gln Pro Glu
            915                 920                 925

Asn Asn Tyr Lys Thr Thr Pro Pro Val Leu Asp Ser Asp Gly Ser Phe
930                 935                 940

Phe Leu Tyr Ser Lys Leu Thr Val Asp Lys Ser Arg Trp Gln Gln Gly
945                 950                 955                 960

Asn Val Phe Ser Cys Ser Val Met His Glu Ala Leu His Asn His Tyr
                965                 970                 975

Thr Gln Lys Ser Leu Ser Leu Ser Pro Gly Lys Ala Arg Thr Gly Gly
            980                 985                 990

Gly Gly Gly Ser Gly Leu Asn Asp Ile Phe Glu Ala Gln Lys Ile Glu
            995                 1000                1005

Trp His Glu
    1010

<210> SEQ ID NO 50
<211> LENGTH: 2994
<212> TYPE: DNA
<213> ORGANISM: Artificial Sequence
<220> FEATURE:
<223> OTHER INFORMATION: ACE2-Fc-Strep-Tag II DNA sequence

<400> SEQUENCE: 50
atgtacagga tgcaactcct gtcttgcatt gcactaagtc ttgcacttgt cacgaattcg    60
ggctcgaggg ctgctcagtc caccattgag aacaggcca agacattttt ggacaagttt   120
aaccacgaag ccgaagacct gttctatcaa agttcacttg cttcttggaa ttataacacc   180
aatattactg aagagaatgt ccaaaacatg aataatgctg gggacaaatg gtctgccttt   240

```
ttaaaggaac agtccacact tgcccaaatg tatccactac aagaaattca gaatctcaca    300
gtcaagcttc agctgcaggc tcttcagcaa aatgggtctt cagtgctctc agaagacaag    360
agcaaacggt tgaacacaat tctaaataca atgagcacca tctacagtac tggaaaagtt    420
tgtaacccag ataatccaca agaatgctta ttacttgaac caggtttgaa tgaaataatg    480
gcaaacagtt tagactacaa tgagaggctc tgggcttggg aaagctggag atctgaggtc    540
ggcaagcagc tgaggccatt atatgaagag tatgtggtct tgaaaaatga gatggcaaga    600
gcaaatcatt atgaggacta tggggattat tggagaggag actatgaagt aaatggggta    660
gatggctatg actacagccg cggccagttg attgaagatg tggaacatac ctttgaagag    720
attaaaccat tatatgaaca tcttcatgcc tatgtgaggg caaagttgat gaatgcctat    780
ccttcctata tcagtccaat tggatgcctc cctgctcatt tgcttggtga tatgtggggt    840
agattttgga caaatctgta ctctttgaca gttccctttg acagaaaacc aaacatagat    900
gttactgatg caatggtgga ccaggcctgg gatgcacaga gaatattcaa ggaggccgag    960
aagttctttg tatctgttgg tcttcctaat atgactcaag gattctggga aaattccatg   1020
ctaacggacc aggaaatgt tcagaaagca gtctgccatc ccacagcttg gacctgggg    1080
aagggcgact tcaggatcct tatgtgcaca aaggtgacaa tggacgactt cctgacagct   1140
catcatgaga tggggcatat ccagtatgat atggcatatg ctgcacaacc ttttctgcta   1200
agaaatggag ctaatgaagg attccatgaa gctgttgggg aaatcatgtc actttctgca   1260
gccacaccta agcatttaaa atccattggt cttctgtcac ccgattttca agaagacaat   1320
gaaacagaaa taaacttcct gctcaaacaa gcactcacga ttgttgggac tctgccattt   1380
acttacatgt tagagaagtg gaggtggatg gtctttaaag gggaaattcc caaagaccag   1440
tggatgaaaa agtggtggga gatgaagcga gagatagttg gggtggtgga acctgtgccc   1500
catgatgaaa catactgtga ccccgcatct ctgttccatg tttctaatga ttactcattc   1560
attcgatatt acacaaggac cctttaccaa ttccagtttc aagaagcact tgtgtcaagca   1620
gctaaacatg aaggccctct gcacaaatgt gacatctcaa actctacaga agctggacag   1680
aaaactgttca atatgctgag gcttggaaaa tcagaacccct ggaccctagc attggaaaat   1740
gttgtaggag caaagaacat gaatgtaagg ccactgctca actactttga gcccttatt    1800
acctggctga agaccagaa caagaattct tttgtgggat ggagtaccga ctggagtcca   1860
tatgcagacc aaagcatcaa agtgaggata agcctaaaat cagctcttgg agataaagca   1920
tatgaatgga cgacaatga atgtacctg ttccgatcat ctgttgcata tgctatgagg   1980
cagtactttt taaaagtaaa aaatcagatg attcttttg gggaggagga tgtgcgagtg   2040
gctaatttga aaccaagaat ctcctttaat ttctttgtca ctgcacctaa aaatgtgtct   2100
gatatcattc ctagaactga agttgaaaag gccatcagga tgtcccggag ccgtatcaat   2160
gatgctttcc gtctgaatga caacagccta gagttctctgg ggatacagcc aacacttgga   2220
cctcctaacc agccccctgt ttccgggccc tcgggctcga gtgctgagcc caaatcttgt   2280
gacaaaactc acacatgcccc accgtgcccca gcacctgaac tcctgggggg accgtcagtc   2340
ttcctcttcc cccaaaaccc caaggacacc ctcatgatct cccggacccc tgaggtcaca   2400
tgcgtggtgg tggacgtgag ccacgaagac cctgaggtca gttcaactg gtacgtggac   2460
ggcgtggagg tgcataatgc caagacaaag ccgcgggagg agcagtacaa cagcacgtac   2520
cgtgtggtca gcgtcctcac cgtcctgcac caggactggc tgaatggcaa ggagtacaag   2580
tgcaaggtct ccaacaaagc cctcccagcc cccatcgaga aaaccatctc caaagccaaa   2640
```

```
gggcagcccc gagaaccaca ggtgtacacc ctgcccccat cccgggagga gatgaccaag   2700
aaccaggtca gcctgacctg cctggtcaaa ggcttctatc ccagcgacat cgccgtggag   2760
tgggagagca atgggcagcc ggagaacaac tacaagacca cgcctcccgt gctggactcc   2820
gacggctcct tcttcctcta cagcaagctc accgtggaca agagcaggtg gcagcagggg   2880
aacgtcttct catgctccgt gatgcatgag gctctgcaca accactacac gcagaagagc   2940
ctctcactgt ctccgggtaa agccgcctgg agtcatccac aattcgaaaa gtag         2994
```

<210> SEQ ID NO 51
<211> LENGTH: 997
<212> TYPE: PRT
<213> ORGANISM: Artificial Sequence
<220> FEATURE:
<223> OTHER INFORMATION: ACE2-Fc-Strep-Tag II amino acid sequence

<400> SEQUENCE: 51

```
Met Tyr Arg Met Gln Leu Leu Ser Cys Ile Ala Leu Ser Leu Ala Leu
1               5                   10                  15

Val Thr Asn Ser Gly Ser Arg Ala Ala Gln Ser Thr Ile Glu Glu Gln
            20                  25                  30

Ala Lys Thr Phe Leu Asp Lys Phe Asn His Glu Ala Glu Asp Leu Phe
        35                  40                  45

Tyr Gln Ser Ser Leu Ala Ser Trp Asn Tyr Asn Thr Asn Ile Thr Glu
    50                  55                  60

Glu Asn Val Gln Asn Met Asn Asn Ala Gly Asp Lys Trp Ser Ala Phe
65                  70                  75                  80

Leu Lys Glu Gln Ser Thr Leu Ala Gln Met Tyr Pro Leu Gln Glu Ile
                85                  90                  95

Gln Asn Leu Thr Val Lys Leu Gln Leu Gln Ala Leu Gln Gln Asn Gly
            100                 105                 110

Ser Ser Val Leu Ser Glu Asp Lys Ser Lys Arg Leu Asn Thr Ile Leu
        115                 120                 125

Asn Thr Met Ser Thr Ile Tyr Ser Thr Gly Lys Val Cys Asn Pro Asp
    130                 135                 140

Asn Pro Gln Glu Cys Leu Leu Leu Glu Pro Gly Leu Asn Glu Ile Met
145                 150                 155                 160

Ala Asn Ser Leu Asp Tyr Asn Glu Arg Leu Trp Ala Trp Glu Ser Trp
                165                 170                 175

Arg Ser Glu Val Gly Lys Gln Leu Arg Pro Leu Tyr Glu Glu Tyr Val
            180                 185                 190

Val Leu Lys Asn Glu Met Ala Arg Ala Asn His Tyr Glu Asp Tyr Gly
        195                 200                 205

Asp Tyr Trp Arg Gly Asp Tyr Glu Val Asn Gly Val Asp Gly Tyr Asp
    210                 215                 220

Tyr Ser Arg Gly Gln Leu Ile Glu Asp Val Glu His Thr Phe Glu Glu
225                 230                 235                 240

Ile Lys Pro Leu Tyr Glu His Leu His Ala Tyr Val Arg Ala Lys Leu
                245                 250                 255

Met Asn Ala Tyr Pro Ser Tyr Ile Ser Pro Ile Gly Cys Leu Pro Ala
            260                 265                 270

His Leu Leu Gly Asp Met Trp Gly Arg Phe Trp Thr Asn Leu Tyr Ser
        275                 280                 285

Leu Thr Val Pro Phe Gly Gln Lys Pro Asn Ile Asp Val Thr Asp Ala
    290                 295                 300
```

```
Met Val Asp Gln Ala Trp Asp Ala Gln Arg Ile Phe Lys Glu Ala Glu
305                 310                 315                 320

Lys Phe Phe Val Ser Val Gly Leu Pro Asn Met Thr Gln Gly Phe Trp
                325                 330                 335

Glu Asn Ser Met Leu Thr Asp Pro Gly Asn Val Gln Lys Ala Val Cys
            340                 345                 350

His Pro Thr Ala Trp Asp Leu Gly Lys Gly Asp Phe Arg Ile Leu Met
        355                 360                 365

Cys Thr Lys Val Thr Met Asp Asp Phe Leu Thr Ala His His Glu Met
    370                 375                 380

Gly His Ile Gln Tyr Asp Met Ala Tyr Ala Ala Gln Pro Phe Leu Leu
385                 390                 395                 400

Arg Asn Gly Ala Asn Glu Gly Phe His Glu Ala Val Gly Glu Ile Met
                405                 410                 415

Ser Leu Ser Ala Ala Thr Pro Lys His Leu Lys Ser Ile Gly Leu Leu
            420                 425                 430

Ser Pro Asp Phe Gln Glu Asp Asn Glu Thr Glu Ile Asn Phe Leu Leu
        435                 440                 445

Lys Gln Ala Leu Thr Ile Val Gly Thr Leu Pro Phe Thr Tyr Met Leu
450                 455                 460

Glu Lys Trp Arg Trp Met Val Phe Lys Gly Glu Ile Pro Lys Asp Gln
465                 470                 475                 480

Trp Met Lys Lys Trp Trp Glu Met Lys Arg Glu Ile Val Gly Val Val
                485                 490                 495

Glu Pro Val Pro His Asp Glu Thr Tyr Cys Asp Pro Ala Ser Leu Phe
            500                 505                 510

His Val Ser Asn Asp Tyr Ser Phe Ile Arg Tyr Tyr Thr Arg Thr Leu
        515                 520                 525

Tyr Gln Phe Gln Phe Gln Glu Ala Leu Cys Gln Ala Ala Lys His Glu
530                 535                 540

Gly Pro Leu His Lys Cys Asp Ile Ser Asn Ser Thr Glu Ala Gly Gln
545                 550                 555                 560

Lys Leu Phe Asn Met Leu Arg Leu Gly Lys Ser Glu Pro Trp Thr Leu
                565                 570                 575

Ala Leu Glu Asn Val Val Gly Ala Lys Asn Met Asn Val Arg Pro Leu
            580                 585                 590

Leu Asn Tyr Phe Glu Pro Leu Phe Thr Trp Leu Lys Asp Gln Asn Lys
        595                 600                 605

Asn Ser Phe Val Gly Trp Ser Thr Asp Trp Ser Pro Tyr Ala Asp Gln
610                 615                 620

Ser Ile Lys Val Arg Ile Ser Leu Lys Ser Ala Leu Gly Asp Lys Ala
625                 630                 635                 640

Tyr Glu Trp Asn Asp Asn Glu Met Tyr Leu Phe Arg Ser Ser Val Ala
                645                 650                 655

Tyr Ala Met Arg Gln Tyr Phe Leu Lys Val Lys Asn Gln Met Ile Leu
            660                 665                 670

Phe Gly Glu Glu Asp Val Arg Val Ala Asn Leu Lys Pro Arg Ile Ser
        675                 680                 685

Phe Asn Phe Phe Val Thr Ala Pro Lys Asn Val Ser Asp Ile Ile Pro
690                 695                 700

Arg Thr Glu Val Glu Lys Ala Ile Arg Met Ser Arg Ser Arg Ile Asn
705                 710                 715                 720
```

```
Asp Ala Phe Arg Leu Asn Asp Asn Ser Leu Glu Phe Leu Gly Ile Gln
                725                 730                 735

Pro Thr Leu Gly Pro Pro Asn Gln Pro Pro Val Ser Gly Pro Ser Gly
            740                 745                 750

Ser Ser Ala Glu Pro Lys Ser Cys Asp Lys Thr His Thr Cys Pro Pro
            755                 760                 765

Cys Pro Ala Pro Glu Leu Leu Gly Gly Pro Ser Val Phe Leu Phe Pro
    770                 775                 780

Pro Lys Pro Lys Asp Thr Leu Met Ile Ser Arg Thr Pro Glu Val Thr
785                 790                 795                 800

Cys Val Val Val Asp Val Ser His Glu Asp Pro Glu Val Lys Phe Asn
                805                 810                 815

Trp Tyr Val Asp Gly Val Glu Val His Asn Ala Lys Thr Lys Pro Arg
                820                 825                 830

Glu Glu Gln Tyr Asn Ser Thr Tyr Arg Val Val Ser Val Leu Thr Val
            835                 840                 845

Leu His Gln Asp Trp Leu Asn Gly Lys Glu Tyr Lys Cys Lys Val Ser
    850                 855                 860

Asn Lys Ala Leu Pro Ala Pro Ile Glu Lys Thr Ile Ser Lys Ala Lys
865                 870                 875                 880

Gly Gln Pro Arg Glu Pro Gln Val Tyr Thr Leu Pro Pro Ser Arg Glu
                885                 890                 895

Glu Met Thr Lys Asn Gln Val Ser Leu Thr Cys Leu Val Lys Gly Phe
            900                 905                 910

Tyr Pro Ser Asp Ile Ala Val Glu Trp Glu Ser Asn Gly Gln Pro Glu
            915                 920                 925

Asn Asn Tyr Lys Thr Thr Pro Pro Val Leu Asp Ser Asp Gly Ser Phe
930                 935                 940

Phe Leu Tyr Ser Lys Leu Thr Val Asp Lys Ser Arg Trp Gln Gln Gly
945                 950                 955                 960

Asn Val Phe Ser Cys Ser Val Met His Glu Ala Leu His Asn His Tyr
                965                 970                 975

Thr Gln Lys Ser Leu Ser Leu Ser Pro Gly Lys Ala Ala Trp Ser His
            980                 985                 990

Pro Gln Phe Glu Lys
        995

<210> SEQ ID NO 52
<211> LENGTH: 8
<212> TYPE: PRT
<213> ORGANISM: Human immunodeficiency virus

<400> SEQUENCE: 52

Cys Cys Ser Cys Gly Ser Cys Cys
1               5
```

METHODS AND COMPOSITIONS FOR TREATING AND PREVENTING VIRAL INFECTION

REFERENCE TO RELATED APPLICATIONS

This application is a continuation of International Application No. PCT/US2021/014818, filed Jan. 23, 2021, which claims the benefit of priority of U.S. Provisional Application No. 62/965,033, filed Jan. 23, 2020, and U.S. Provisional Application No. 63/050,473, filed Jul. 10, 2020, the contents of which are incorporated by reference as if written herein in their entireties.

INCORPORATION OF SEQUENCE LISTING

The sequence listing that is contained in the file named "HAN0001-401-PC_ST25," which is 107 kilobytes as measured in Microsoft Windows operating system and was created on Jan. 21, 2021, is filed electronically herewith and incorporated herein by reference.

BACKGROUND

The present disclosure relates to virology. More particularly, the present disclosure related to methods and compositions for treating and preventing viral infection.

Entry into host cells by viruses is mediated by viral envelope (Env) proteins that bind to cell surface receptors of host cells. Binding of viruses to their receptors requires specific domain recognition, but also involves charge interactions between a positive (+) charge present in the viral proteins and a negative (−) charge present in receptors. Receptors can be negatively charged by a stretch of acidic amino acids or protein sulfation. The latter ensures a strong (−) charge due to a large ionization potential provided by a $SO_4$ group in physiologic pH in a cell. One example of a virus that uses this mechanism is Hepatitis C virus (HCV), which is one of the leading causes of preventable death globally, with an estimated 400,000 deaths each year. There is no effective vaccine for HCV, but expensive curative drugs against HCV are currently available. Although the HCV drug treatment is effective in majority (~90%) of patients, a significant fraction of patients remains untreatable. Moreover, the long term (>~10 years) efficacy of HCV treatment remains to be seen. Another example of a virus that uses the same mechanism is Hepatitis B virus (HBV), which, as a member of Hepadnaviridae family, causes chronic infection in 250 million people, with an annual mortality rate of 600,000. Although an effective HBV vaccine is available, there is no curative HBV drug that effectively treats virus infection. Current HBV drugs only suppress the replication of the virus, rendering most people continue them for life. HBV as well as HCV remains as a global health problem. The present disclosure thus provides a treatment for viruses, including HCV and HBV, that is both effective for all types of viruses and more cost effective for patients seeking treatment by providing recombinant polypeptides for treating or preventing viral infection comprising: a) Ig Fc fragment and b) a sulfated polysaccharide as a first ligand binding site; and c) at least one viral receptor fragment as the second binding site. Thus, target viruses are efficiently bound and neutralized by co-operative binding nature of the recombinant Fc.

SUMMARY

In one aspect, the disclosure provides a recombinant polypeptide comprising an Ig Fc fragment conjugated to at least one viral receptor. In some embodiments, the recombinant polypeptide includes an Fc fragment and 2 viral receptors. In some embodiments, the at least one viral receptor is selected from heparan sulfate proteoglycan (HSPG), CD81, SRB1, CD26, ACE2, CD147, sialic acid, DC-SIGN (CD209), AXL, Tyro3, TIM-1, PtdSer R (CD300a), NPC1, and NTCP. In some embodiments, the recombinant polypeptide comprises an Ig Fc fragment and a streptavidin (SA) or an AviTag™ or a Strep-Tag II®. In some embodiments, the recombinant polypeptide is part of a complex comprising multiple copies of the recombinant polypeptide, thereby forming, e.g., a dimer, a trimer, a tetramer, an octamer, a decamer, or more. In some embodiments, a dimer of the recombinant polypeptide can complex with multiple copies of the dimer complex.

In one aspect, the disclosure provides a recombinant polypeptide comprising: a) an immunoglobulin Fc fragment and a sulfated polysaccharide; and b) at least one viral receptor or fragment thereof. In one embodiment, (a) and (b) are capable of co-operative binding of at least one viral envelope protein. In another embodiment, the sulfated polysaccharide is heparan sulfate (HS). In another embodiment, the HS is a proteoglycan (HSPG). In another embodiment, the HSPG contains two or more sulfation sites. In another embodiment, the sulfation site comprises a serine-glycine-aspartic acid (SGD) motif. In another embodiment, the SGD motif is within 7, 8, 9, and/or 10 residues of at least one acidic amino acid residue. In another embodiment, the at least one viral receptor or fragment thereof is for a virus family selected from the group consisting of flaviviridae, coronaviridae, and hepadnaviridae. In another embodiment, the virus family is flaviviridae. In another embodiment, the flaviviridae virus is selected from the group consisting of HCV, West Nile, and Dengue. In another embodiment, the virus is HCV. In another embodiment, the at least one viral receptor or fragment thereof is CD81 and/or Scavenger Receptor B-1 (SRB1). In another embodiment, the virus is West Nile or Dengue. In another embodiment, the at least one viral receptor or fragment thereof is AXL and/or TIM-1 and/or TIM-4. In another embodiment, the virus family is coronaviridae. In another embodiment, the coronaviridae virus is Middle East Respiratory Syndrome (MERS). In another embodiment, the at least one viral receptor or fragment thereof is CD26 and/or CD26-Blade4 and/or CD26-B4C. In another embodiment, the coronaviridae virus is Severe Acute Respiratory Syndrome (SARS). In another embodiment, the severe acute respiratory syndrome (SARS) virus is SARS-CoV or SARS-CoV-2. In another embodiment, the at least one viral receptor or fragment thereof is selected from the group consisting of ACE2, CD147, sialic acid, and SRB1. In another embodiment, the at least one viral receptor or fragment thereof is ACE2. In another embodiment, the sulfated polysaccharide is HSPG. In another embodiment, the at least one viral receptor or fragment thereof is CD147. In another embodiment, the sulfated polysaccharide is HSPG. In another embodiment, the at least one viral receptor or fragment thereof is sialic acid. In another embodiment, the sulfated polysaccharide is HSPG. In another embodiment, the at least one viral receptor or fragment thereof is SRB1. In another embodiment, the sulfated polysaccharide is HSPG. In another embodiment, the coronaviridae virus is a Setracovirus. In another embodiment, the Setracovirus is human coronavirus (hCoV)-NL63. In another embodiment, the at least one viral receptor or fragment thereof is ACE2. In another embodiment, the sulfated polysaccharide is HSPG. In another embodiment, the virus family is hepadnaviridae. In another embodiment, the virus is HBV. In another embodiment, the at least one viral receptor or fragment thereof is NTCP (sodium taurocholate co-transporting polypeptide). In another embodiment, the sulfated polysaccharide is HSPG. In another embodiment, the disclosure provides a pharmaceutical composition comprising a recombinant polypeptide as described herein. In another embodiment, the disclosure provides a method of preventing or treating a viral infection in a subject in need thereof, comprising administering to the subject a therapeutically or prophylactically effective amount of a pharmaceutical composition as described herein. In another embodiment, the viral infection is a result of a virus family selected from the group consisting of flaviviridae, coronaviridae, and hepadnaviridae. In another embodiment, the virus family is flaviviridae. In another embodiment, the flaviviridae virus is selected from the group consisting of HCV, West Nile, and Dengue. In another embodiment, the virus family is coronaviridae. In another embodiment, the coronaviridae virus is MERS, SARS, or hCoV-NL63. In another embodiment, the virus family is hepadnaviridae. In another embodiment, the hepadnaviridae virus is HBV. In another embodiment, the disclosure provides a RNA molecule comprising: a) a first ribonucleotide sequence having a 5'-Cap or expressing an Internal Ribosome Entry Site (IRES); and b) a second ribonucleotide sequence expressing a recombinant polypeptide as described herein. In another embodiment, the disclosure provides a therapeutic composition comprising: a) a live viral expression vector; and b) a polynucleotide sequence expressing a recombinant polypeptide as described herein. In another embodiment, the expression vector is an adenovirus vector or a vaccinia vector. In another embodiment, the adenovirus vector is selected from the group consisting of Ad5, Ad26, and adeno-associated virus (AAV). In another embodiment, the vaccinia vector is Canary Pox.

In another embodiment, the disclosure provides an expression system comprising a polynucleotide sequence encoding a recombinant polypeptide as described herein. In another embodiment, the disclosure provides a recombinant polypeptide for treating SARS-CoV-2 infection comprising an amino acid sequence having at least 95% sequence identity to a sequence set forth as SEQ ID NOs:31, 37, or 45. In one embodiment, the disclosure provides a polynucleotide encoding a recombinant polypeptide as described herein, wherein the polynucleotide comprises at least 95% sequence identity to a sequence set forth as SEQ ID NOs: 25-30. In another embodiment, the disclosure provides a polynucleotide encoding a recombinant polypeptide as described herein, wherein the polynucleotide comprises at least 95% sequence identity to a sequence set forth as SEQ ID NOs:25, 28, 30, 34-36, and 38. In another embodiment, the disclosure provides a polynucleotide encoding a recombinant polypeptide as described herein, wherein the polynucleotide comprises at least 95% sequence identity to a sequence set forth as SEQ ID NOs:25, 28, 30, and 39-44. In another embodiment, the disclosure provides a recombinant polypeptide for treating SARS-CoV-2 infection comprising an amino acid sequence set forth as SEQ ID NOs:31, 37, or 45. In another embodiment, the disclosure provides a polynucleotide encoding a recombinant polypeptide as described herein, wherein the polynucleotide comprises SEQ ID NOs: 25-30. In another embodiment, the disclosure provides a polynucleotide encoding a recombinant polypeptide as described herein, wherein the polynucleotide comprises SEQ ID NOs:25, 28, 30, 34-36, and 38. In another embodiment, the disclosure provides a polynucleotide encoding a recombinant polypeptide as described herein, wherein the polynucleotide comprises SEQ ID NOs:25, 28, 30, and 39-44.

In another embodiment, the disclosure provides a pharmaceutical composition comprising a recombinant polypeptide as described herein. In another embodiment, the disclosure provides a a method of preventing or treating a viral infection in a subject in need thereof, comprising administering to the subject a therapeutically or prophylactically effective amount of a pharmaceutical composition as described herein. In one embodiment, the viral infection is a result of the coronaviridae virus family. In another embodiment, the coronaviridae virus is severe acute respiratory syndrome (SARS) virus or human coronavirus (hCoV)-NL63. In another embodiment, the severe acute respiratory syndrome (SARS) virus is SARS-CoV or SARS-CoV-2. In another embodiment, the pharmaceutical composition is administered via the respiratory pathway or intravenously. In another embodiment, administration via the respiratory pathway comprises the use of an inhaler for the lower respiratory tract, or an intra-nasal spray for the upper respiratory tract. In another embodiment, such a method further comprises administration of heparin for treatment of SARS-CoV, SARS-CoV-2, or human coronavirus (hCoV)-NL63 infection. In another embodiment, the heparin prevents entry of the SARS-CoV, SARS-CoV-2, or human coronavirus (hCoV)-NL63 virus into a host cell.

In another aspect, the disclosure provides a recombinant polypeptide comprising: a) an Ig Fc fragment; b) a first viral receptor, wherein the receptor is ACE2 or fragment thereof; and c) a second viral receptor. In one embodiment, the second viral receptor is selected from the group consisting of HSPG, CD147, sialic acid, and SRB1. In another embodiment, the second viral receptor is HSPG. In another embodiment, the second viral receptor is CD147. In another embodiment, the second viral receptor is sialic acid. In another embodiment, the second viral receptor is SRB1. In another embodiment, a polypeptide as described herein is used for the treatment of SARS-CoV, SARS-CoV-2, or human coronavirus (hCoV)-NL63. In another embodiment, the disclosure provides a pharmaceutical composition comprising a recombinant polypeptide described herein. In another embodiment, In another embodiment, the disclosure provides method of preventing or treating a viral infection in a subject in need thereof, comprising administering to the subject a therapeutically or prophylactically effective amount of a pharmaceutical composition as described herein. In another embodiment, the disclosure provides a RNA molecule comprising: a) a first ribonucleotide sequence having a 5'-Cap or expressing an Internal Ribosome Entry Site (IRES); and b) a second ribonucleotide sequence expressing a recombinant polypeptide as described herein. In another embodiment, the disclosure provides a therapeutic composition comprising: a) a live viral expression vector; and b) a polynucleotide sequence expressing a recombinant polypeptide as described herein.

In another aspect, the disclosure provides a recombinant polypeptide comprising: a) an Ig Fc fragment; b) a viral receptor or fragment thereof; and c) streptavidin. In another embodiment, the viral receptor is selected from the group consisting of HSPG, CD81, SRB1, CD26, ACE2, CD147, sialic acid, DC-SIGN (CD209), AXL, Tyro3, TIM-1, PtdSer R (CD300a), NPC1, and NTCP. In another embodiment, the viral receptor is ACE2. In another embodiment, a recombinant polypeptide as described herein, used for the treatment of SARS-CoV, SARS-CoV-2, or human coronavirus (hCoV)-NL63. In another embodiment, the disclosure provides a pharmaceutical composition comprising a recombinant polypeptide as described herein. In another embodiment, the disclosure provides a method of preventing or treating a viral infection in a subject in need thereof, comprising administering to the subject a therapeutically or prophylactically effective amount of a pharmaceutical composition as described herein. In another embodiment, the disclosure provides a RNA molecule comprising: a) a first ribonucleotide sequence having a 5'-Cap or expressing an Internal Ribosome Entry Site (IRES); and b) a second ribonucleotide sequence expressing a recombinant polypeptide as described herein. In another embodiment, the disclosure provides a therapeutic composition comprising: a) a live viral expression vector; and b) a polynucleotide sequence expressing a recombinant polypeptide as described herein.

In another aspect, the disclosure provides a recombinant polypeptide comprising: a) an Ig Fc fragment; b) a first viral receptor, and c) a second viral receptor. In one embodiment, the first viral receptor is selected from the group consisting of DC-SIGN (CD209), AXL, Tyro3, TIM-1, PtdSer R (CD300a), TIM-1 and NPC1. In another embodiment, the second viral receptor is selected from the group consisting of DC-SIGN (CD209), AXL, Tyro3, TIM-1, PtdSer R (CD300a), TIM-1 and NPC1. In another embodiment, a recombinant polypeptide as described herein is used for the treatment of Zika or Ebola. In another embodiment, the disclosure provides a pharmaceutical composition comprising a recombinant polypeptide as described herein. In another embodiment, the disclosure provides a method of preventing or treating a viral infection in a subject in need thereof, comprising administering to the subject a therapeutically or prophylactically effective amount of a pharmaceutical composition as described herein. In another embodiment, the disclosure provides a RNA molecule comprising: a) a first ribonucleotide sequence having a 5'-Cap or expressing an Internal Ribosome Entry Site (IRES); and b) a second ribonucleotide sequence expressing a recombinant polypeptide as described herein. In another embodiment, the disclosure provides a therapeutic composition comprising: a) a live viral expression vector; and b) a polynucleotide sequence expressing a recombinant polypeptide as described herein.

Embodiment 1—A recombinant polypeptide comprising an Ig Fc fragment conjugated to at least one viral receptor.

Embodiment 2—A recombinant polypeptide comprising an Fc fragment conjugated to 2 viral receptors.

Embodiment 3—The recombinant polypeptide of Embodiments 1 or 2, wherein the at least one viral receptor is selected from heparan sulfate proteoglycan (HSPG), CD81, SRB1, CD26, ACE2, CD147, sialic acid, DC-SIGN (CD209), AXL, Tyro3, TIM-1, PtdSer R (CD300a), NPC1, and NTCP.

Embodiment 4—The recombinant polypeptide of any of Embodiments 1-3, further comprising a streptavidin (SA) or an AviTag™ or a Strep-Tag II®.

Embodiment 5—The recombinant polypeptide of any of Embodiments 1-4, wherein the recombinant polypeptide is part of a complex comprising multiple copies of the recombinant polypeptide, thereby forming, e.g., a dimer, a trimer, a tetramer, an octamer, a decamer, or more.

Embodiment 6—The recombinant polypeptide of any of Embodiments 1-5, wherein a dimer of the recombinant polypeptide can complex with multiple copies of the dimer complex.

Embodiment 7—A recombinant polypeptide comprising: a) an immunoglobulin Fc fragment and a sulfated polysaccharide; and b) at least one viral receptor or fragment thereof.

Embodiment 8—The recombinant polypeptide of any of Embodiments 1-7, wherein (a) and (b) are capable of co-operative binding of at least one viral envelope protein.

Embodiment 9—The recombinant polypeptide of any of Embodiments 1-8, wherein the sulfated polysaccharide is heparan sulfate (HS).

Embodiment 10—The recombinant polypeptide of any of Embodiments 1-9, wherein the HS is part of a heparan sulfate proteoglycan (HSPG).

Embodiment 11—The recombinant polypeptide of any of Embodiments 1-10, wherein the HSPG contains two or more sulfation sites.

Embodiment 12—The recombinant polypeptide of any of Embodiments 1-11, wherein the sulfation site comprises a serine-glycine-aspartic acid (SGD) motif.

Embodiment 13—The recombinant polypeptide of any of Embodiments 1-12, wherein the SGD motif is within 7, 8, 9, and/or 10 residues of at least one acidic amino acid residue.

Embodiment 14—The recombinant polypeptide of any of Embodiments 1-13, wherein the at least one viral receptor or fragment thereof is for a virus family selected from the group consisting of flaviviridae, coronaviridae, and hepadnaviridae.

Embodiment 15—The recombinant polypeptide of any of Embodiments 1-14, wherein the virus family is flaviviridae.

Embodiment 16—The recombinant polypeptide of any of Embodiments 1-15, wherein the flaviviridae virus is selected from the group consisting of HCV, West Nile, and Dengue.

Embodiment 17—The recombinant polypeptide of any of Embodiments 1-16, wherein the virus is HCV.

Embodiment 18—The recombinant polypeptide of any of Embodiments 1-17, wherein the at least one viral receptor or fragment thereof is CD81 and/or Scavenger Receptor B-1 (SRB1).

Embodiment 19—The recombinant polypeptide of any of Embodiments 1-18, wherein the virus is West Nile or Dengue.

Embodiment 20—The recombinant polypeptide of any of Embodiments 1-19, wherein the at least one viral receptor or fragment thereof is AXL and/or TIM-1 and/or TIM-4.

Embodiment 21—The recombinant polypeptide of any of Embodiments 1-20, wherein the virus family is coronaviridae.

Embodiment 22—The recombinant polypeptide of any of Embodiments 1-21, wherein the coronaviridae virus is Middle East Respiratory Syndrome (MERS).

Embodiment 23—The recombinant polypeptide of any of Embodiments 1-22, wherein the at least one viral receptor or fragment thereof is CD26 and/or CD26-Blade4 and/or CD26-B4C.

Embodiment 24—The recombinant polypeptide of any of Embodiments 1-23, wherein the coronaviridae virus is Severe Acute Respiratory Syndrome (SARS).

Embodiment 25—The recombinant polypeptide of any of Embodiments 1-24, wherein the severe acute respiratory syndrome (SARS) virus is SARS-CoV or SARS-CoV-2.

Embodiment 26—The recombinant polypeptide of any of Embodiments 1-25, wherein the at least one viral receptor or fragment thereof is selected from the group consisting of ACE2, CD147, sialic acid, and SRB1.

Embodiment 27—The recombinant polypeptide of any of Embodiments 1-26, wherein the at least one viral receptor or fragment thereof is ACE2.

Embodiment 28—The recombinant polypeptide of any of Embodiments 1-27, wherein the sulfated polysaccharide is HSPG.

Embodiment 29—The recombinant polypeptide of any of Embodiments 1-28, wherein the at least one viral receptor or fragment thereof is CD147.

Embodiment 30—The recombinant polypeptide of any of Embodiments 1-29, wherein the sulfated polysaccharide is HSPG.

Embodiment 31—The recombinant polypeptide of any of Embodiments 1-30, wherein the at least one viral receptor or fragment thereof is sialic acid.

Embodiment 32—The recombinant polypeptide of any of Embodiments 1-31, wherein the sulfated polysaccharide is HSPG.

Embodiment 33—The recombinant polypeptide of any of Embodiments 1-32, wherein the at least one viral receptor or fragment thereof is SRB1.

Embodiment 34—The recombinant polypeptide of any of Embodiments 1-33, wherein the sulfated polysaccharide is HSPG.

Embodiment 35—The recombinant polypeptide of any of Embodiments 1-34, wherein the coronaviridae virus is a Setracovirus.

Embodiment 36—The recombinant polypeptide of any of Embodiments 1-35, wherein the Setracovirus is human coronavirus (hCoV)-NL63.

Embodiment 37—The recombinant polypeptide of any of Embodiments 1-36, wherein the at least one viral receptor or fragment thereof is ACE2.

Embodiment 38—The recombinant polypeptide of any of Embodiments 1-37, wherein the sulfated polysaccharide is HSPG.

Embodiment 39—The recombinant polypeptide of any of Embodiments 1-38, wherein the virus family is hepadnaviridae.

Embodiment 40—The recombinant polypeptide of any of Embodiments 1-39, wherein the virus is HBV.

Embodiment 41—The recombinant polypeptide of any of Embodiments 1-40, wherein the at least one viral receptor or fragment thereof is NTCP (sodium taurocholate co-transporting polypeptide).

Embodiment 42—The recombinant polypeptide of any of Embodiments 1-41, wherein the sulfated polysaccharide is HSPG.

Embodiment 43—A pharmaceutical composition comprising the recombinant polypeptide of any of Embodiments 1-42.

Embodiment 44—A method of preventing or treating a viral infection in a subject in need thereof, comprising administering to the subject a therapeutically or prophylactically effective amount of the pharmaceutical composition of any of Embodiments 1-43.

Embodiment 45—The method of any of Embodiments 1-44, wherein the viral infection is a result of a virus family selected from the group consisting of flaviviridae, coronaviridae, and hepadnaviridae.

Embodiment 46—The method of any of Embodiments 1-45, wherein the virus family is flaviviridae.

Embodiment 47—The method of any of Embodiments 1-46, wherein the flaviviridae virus is selected from the group consisting of HCV, West Nile, and Dengue.

Embodiment 48—The method of any of Embodiments 1-47, wherein the virus family is coronaviridae.

Embodiment 49—The method of any of Embodiments 1-48, wherein the coronaviridae virus is MERS, SARS, or hCoV-NL63.

Embodiment 50—The method of any of Embodiments 1-49, wherein the virus family is hepadnaviridae.

Embodiment 51—The method of any of Embodiments 1-50, wherein the hepadnaviridae virus is HBV.

Embodiment 52—A RNA molecule comprising: a) a first ribonucleotide sequence having a 5'-Cap or expressing an Internal Ribosome Entry Site (IRES); and b) a second ribonucleotide sequence expressing the recombinant polypeptide of any of Embodiments 1-51.

Embodiment 53—A therapeutic composition comprising: a) a live viral expression vector; and b) a polynucleotide sequence expressing the recombinant polypeptide of any of Embodiments 1-52.

Embodiment 54—The therapeutic composition of any of Embodiments 1-53, wherein the expression vector is an adenovirus vector or a vaccinia vector.

Embodiment 55—The therapeutic composition of any of Embodiments 1-54, wherein the adenovirus vector is selected from the group consisting of Ad5, Ad26, and adeno-associated virus (AAV).

Embodiment 56—The therapeutic composition of any of Embodiments 1-55, wherein the vaccinia vector is Canary Pox.

Embodiment 57—An expression system comprising a polynucleotide sequence encoding the recombinant polypeptide of any of Embodiments 1-56.

Embodiment 58—A recombinant polypeptide for treating SARS-CoV-2 infection comprising an amino acid sequence having at least 95% sequence identity to a sequence set forth as SEQ ID NOs:31, 37, or 45.

Embodiment 59—A polynucleotide encoding the recombinant polypeptide of any of Embodiments 1-58, wherein the polynucleotide comprises at least 95% sequence identity to a sequence set forth as SEQ ID NOs:25-30.

Embodiment 60—A polynucleotide encoding the recombinant polypeptide of any of Embodiments 1-59, wherein the polynucleotide comprises at least 95% sequence identity to a sequence set forth as SEQ ID NOs:25, 28, 30, 34-36, and 38.

Embodiment 61—A polynucleotide encoding the recombinant polypeptide of any of Embodiments 1-60, wherein the polynucleotide comprises at least 95% sequence identity to a sequence set forth as SEQ ID NOs:25, 28, 30, and 39-44.

Embodiment 62—A recombinant polypeptide for treating SARS-CoV-2 infection comprising an amino acid sequence set forth as SEQ ID NOs:31, 37, or 45.

Embodiment 63—A polynucleotide encoding the recombinant polypeptide of any of Embodiments 1-62, wherein the polynucleotide comprises SEQ ID NOs:25-30.

Embodiment 64—A polynucleotide encoding the recombinant polypeptide of any of Embodiments 1-63, wherein the polynucleotide comprises SEQ ID NOs:25, 28, 30, 34-36, and 38.

Embodiment 65—A polynucleotide encoding the recombinant polypeptide of any of Embodiments 1-64, wherein the polynucleotide comprises SEQ ID NOs:25, 28, 30, and 39-44.

Embodiment 66—A pharmaceutical composition comprising the recombinant polypeptide of any of Embodiments 1-65.

Embodiment 67—A method of preventing or treating a viral infection in a subject in need thereof, comprising administering to the subject a therapeutically or prophylactically effective amount of the pharmaceutical composition of any of Embodiments 1-66.

Embodiment 68—The method of any of Embodiments 1-67, wherein the viral infection is a result of the coronaviridae virus family.

Embodiment 69—The method of any of Embodiments 1-68, wherein the coronaviridae virus is severe acute respiratory syndrome (SARS) virus or human coronavirus (hCoV)-NL63.

Embodiment 70—The method of any of Embodiments 1-69, wherein the severe acute respiratory syndrome (SARS) virus is SARS-CoV or SARS-CoV-2.

Embodiment 71—The method of any of Embodiments 1-70, wherein the pharmaceutical composition is administered via the respiratory pathway or intravenously.

Embodiment 72—The method of any of Embodiments 1-71, wherein administration via the respiratory pathway comprises the use of an inhaler for the lower respiratory tract, or an intra-nasal spray for the upper respiratory tract.

Embodiment 73—The method of any of Embodiments 1-72, further comprising administration of heparin for treatment of SARS-CoV, SARS-CoV-2, or human coronavirus (hCoV)-NL63 infection.

Embodiment 74—The method of any of Embodiments 1-73, wherein the heparin prevents entry of the SARS-CoV, SARS-CoV-2, or human coronavirus (hCoV)-NL63 virus into a host cell.

Embodiment 75—A recombinant polypeptide comprising: a) an Ig Fc fragment; b) a first viral receptor, wherein the receptor is ACE2 or fragment thereof; and c) a second viral receptor.

Embodiment 76—The recombinant polypeptide of any of Embodiments 1-75, wherein the second viral receptor is selected from the group consisting of HSPG, CD147, sialic acid, and SRB1.

Embodiment 77—The recombinant polypeptide of any of Embodiments 1-76, wherein the second viral receptor is HSPG.

Embodiment 78—The recombinant polypeptide of any of Embodiments 1-77, wherein the second viral receptor is CD147.

Embodiment 79—The recombinant polypeptide of any of Embodiments 1-78, wherein the second viral receptor is sialic acid.

Embodiment 80—The recombinant polypeptide of any of Embodiments 1-79, wherein the second viral receptor is SRB1.

Embodiment 81—The recombinant polypeptide of any of Embodiments 1-80, used for the treatment of SARS-CoV, SARS-CoV-2, or human coronavirus (hCoV)-NL63.

Embodiment 82—A pharmaceutical composition comprising the recombinant polypeptide of any of any of Embodiments 1-81.

Embodiment 83—A method of preventing or treating a viral infection in a subject in need thereof, comprising administering to the subject a therapeutically or prophylactically effective amount of the pharmaceutical composition of any of Embodiments 1-82.

Embodiment 84—A RNA molecule comprising: a) a first ribonucleotide sequence having a 5'-Cap or expressing an Internal Ribosome Entry Site (IRES); and b) a second ribonucleotide sequence expressing the recombinant polypeptide of any of Embodiments 1-83.

Embodiment 85—A therapeutic composition comprising: a) a live viral expression vector; and b) a polynucleotide sequence expressing the recombinant polypeptide of any of any of Embodiments 1-84.

Embodiment 86—A recombinant polypeptide comprising: a) an Ig Fc fragment; b) a viral receptor or fragment thereof; and c) streptavidin.

Embodiment 87—The recombinant polypeptide of any of Embodiments 1-86, wherein the viral receptor is selected from the group consisting of HSPG, CD81, SRB1, CD26, ACE2, CD147, sialic acid, DC-SIGN (CD209), AXL, Tyro3, TIM-1, PtdSer R (CD300a), NPC1, and NTCP.

Embodiment 88—The recombinant polypeptide of any of Embodiments 1-87, wherein the viral receptor is ACE2.

Embodiment 89—The recombinant polypeptide of any of Embodiments 1-88, used for the treatment of SARS-CoV, SARS-CoV-2, or human coronavirus (hCoV)-NL63.

Embodiment 90—A pharmaceutical composition comprising the recombinant polypeptide of any of Embodiments 1-89.

Embodiment 91—A method of preventing or treating a viral infection in a subject in need thereof, comprising administering to the subject a therapeutically or prophylactically effective amount of a pharmaceutical composition as described herein.

Embodiment 92—A RNA molecule comprising: a) a first ribonucleotide sequence having a 5'-Cap or expressing an Internal Ribosome Entry Site (IRES); and b) a second ribonucleotide sequence expressing the recombinant polypeptide of any of Embodiments 1-91.

Embodiment 93—A therapeutic composition comprising: a) a live viral expression vector; and b) a polynucleotide sequence expressing the recombinant polypeptide of any of Embodiments 1-92.

Embodiment 94—A recombinant polypeptide comprising: a) an Ig Fc fragment; b) a first viral receptor, and c) a second viral receptor.

Embodiment 95—The recombinant polypeptide of any of Embodiments 1-94, wherein the first viral receptor is selected from the group consisting of DC-SIGN (CD209), AXL, Tyro3, TIM-1, PtdSer R (CD300a), TIM-1 and NPC1.

Embodiment 96—The recombinant polypeptide of any of Embodiments 1-95, wherein the second viral receptor is selected from the group consisting of DC-SIGN (CD209), AXL, Tyro3, TIM-1, PtdSer R (CD300a), TIM-1 and NPC1.

Embodiment 97—The recombinant polypeptide of any of any of Embodiments 1-96, used for the treatment of Zika.

Embodiment 98—The recombinant polypeptide of any of Embodiments 1-97, used for the treatment of Ebola.

Embodiment 99—A pharmaceutical composition comprising the recombinant polypeptide of any of Embodiments 1-98.

Embodiment 100—A method of preventing or treating a viral infection in a subject in need thereof, comprising administering to the subject a therapeutically or prophylactically effective amount of the pharmaceutical composition of any of Embodiments 1-99.

Embodiment 101—A RNA molecule comprising: a) a first ribonucleotide sequence having a 5'-Cap or expressing an Internal Ribosome Entry Site (IRES); and b) a second ribonucleotide sequence expressing the recombinant polypeptide of any of Embodiments 1-100.

Embodiment 102—A therapeutic composition comprising: a) a live viral expression vector; and b) a polynucleotide sequence expressing the recombinant polypeptide of any of any of Embodiments 1-101.

BRIEF DESCRIPTION OF THE DRAWINGS

FIG. 1—Shows a schematic of a recombinant polypeptide as described herein for treatment or prevention of Hepatitis C virus (HCV), having an Fc and viral receptor fragments.

Figure 2:
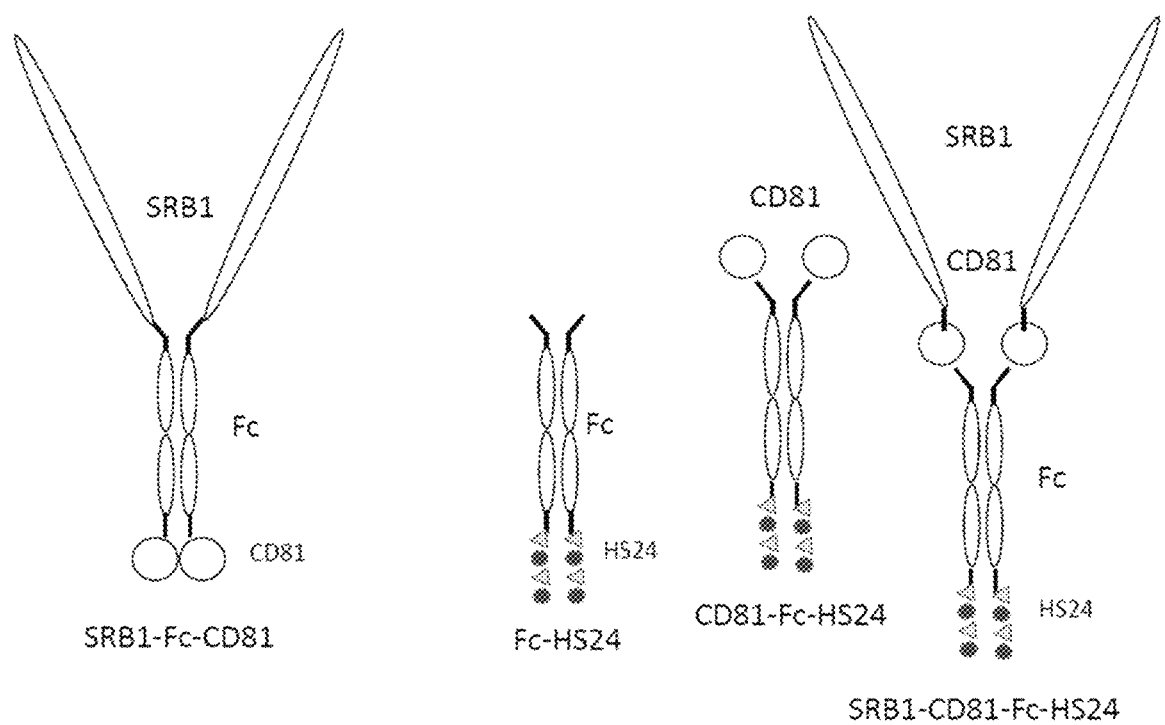

FIG. 2—Shows variants of recombinant polypeptides for treatment or prevention of HCV.

Figure 3:
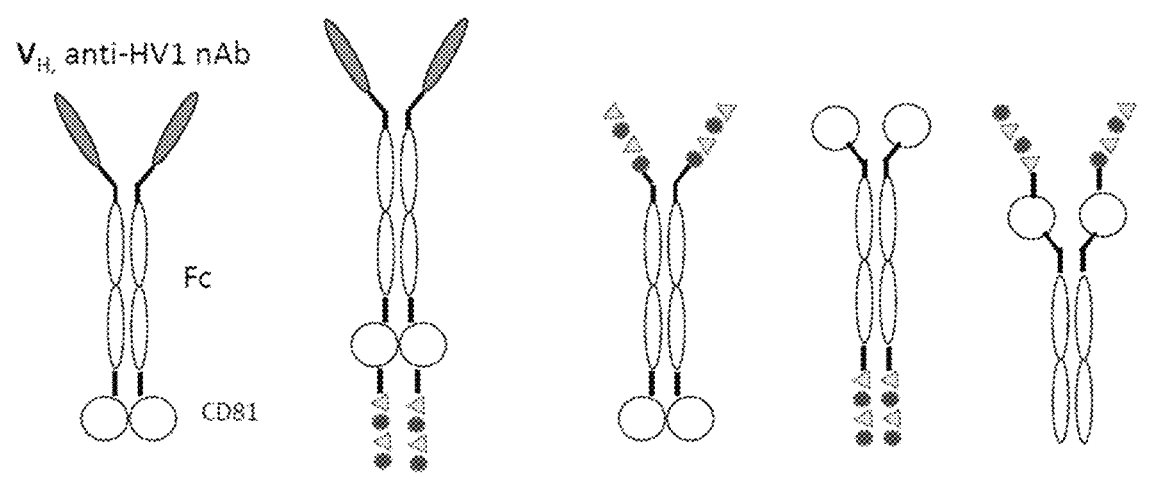

FIG. 3—Shows variants of recombinant polypeptides for treatment or prevention of HCV.

Figure 4:
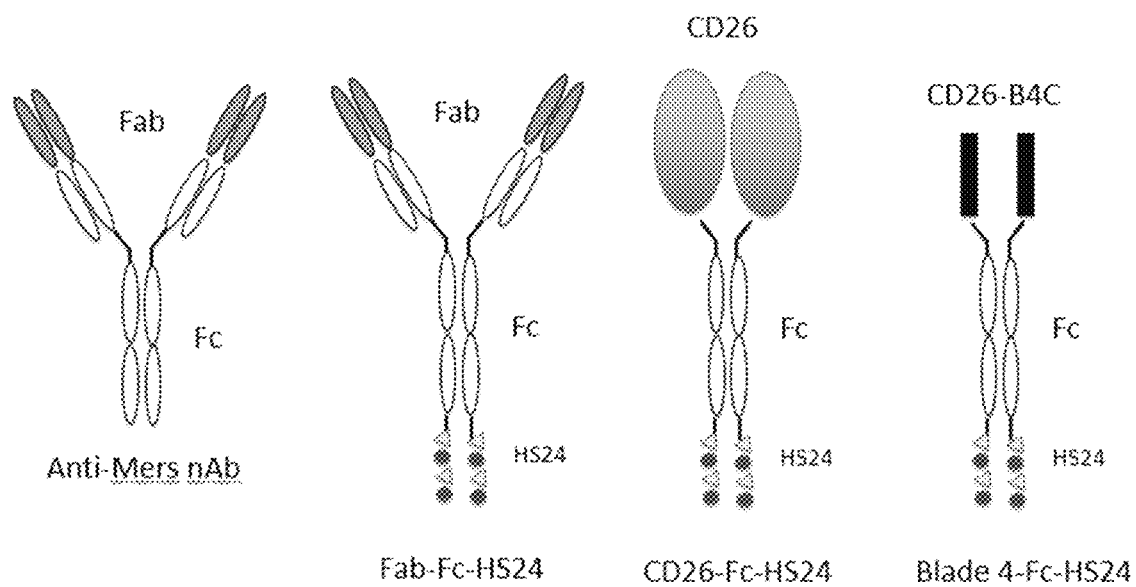

FIG. 4—Shows a schematic of a recombinant polypeptide as described herein for treatment or prevention of the Middle East Respiratory syndrome (MERS) virus, having an Fc and viral receptor fragments.

Figure 5:
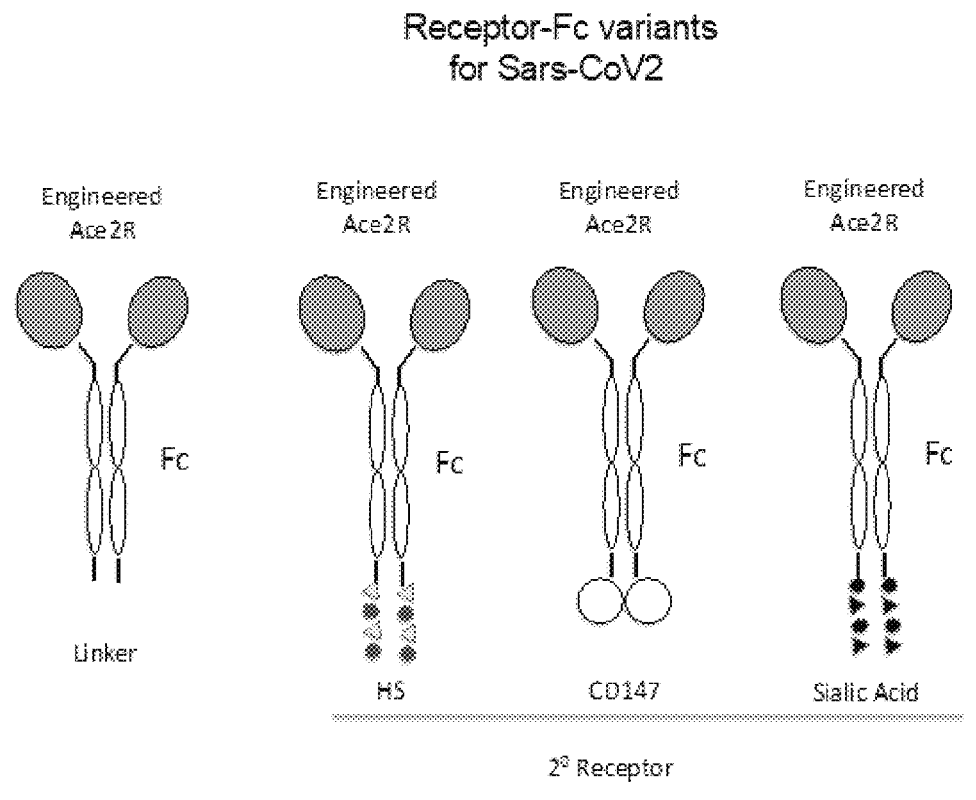

FIG. 5—Shows a schematic of receptor-Fc variants for SARS-CoV-2.

FIG. 6—Shows the sequence of the human SRB1 extracellular domain (top) and full-length sequence (bottom), corresponding to SEQ ID NOs:10 and 11, respectively.

FIG. 7—Shows the sequence of the human CD81 full-length sequence (top) and extracellular domain (bottom), corresponding to SEQ ID NOs:14 and 15, respectively.

Figure 8:
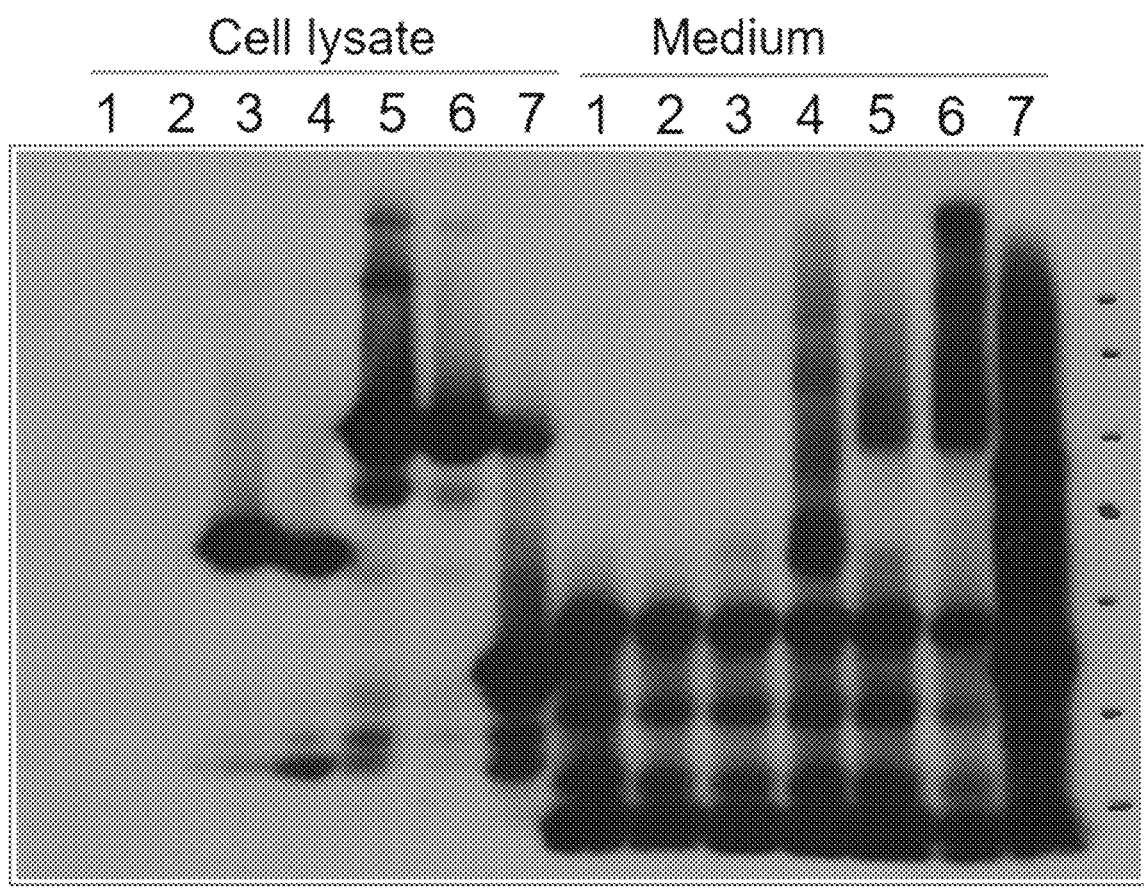

FIG. 8—Shows expression of various R-Ig proteins in 293T cells, using rabbit anti-human IgG Ab-HRP, 1:2000 for 1 hour. Lanes of the gel are labeled and are as follows: (1) Mock; (2) Mock; (3) CD26-Fc-HS; (4) CD26-AA-Fc-HS; (5) Srb1-CD81-Fc-HS; (6) Srb1-AA-CD81-Fc-HS; (7) CD81-Fc-HS. CD26 refers to blade-4 portion of protein. AA refers to extra 2 alanine residues at the N-terminus of the signal peptide to increase secretion.

Figure 9:
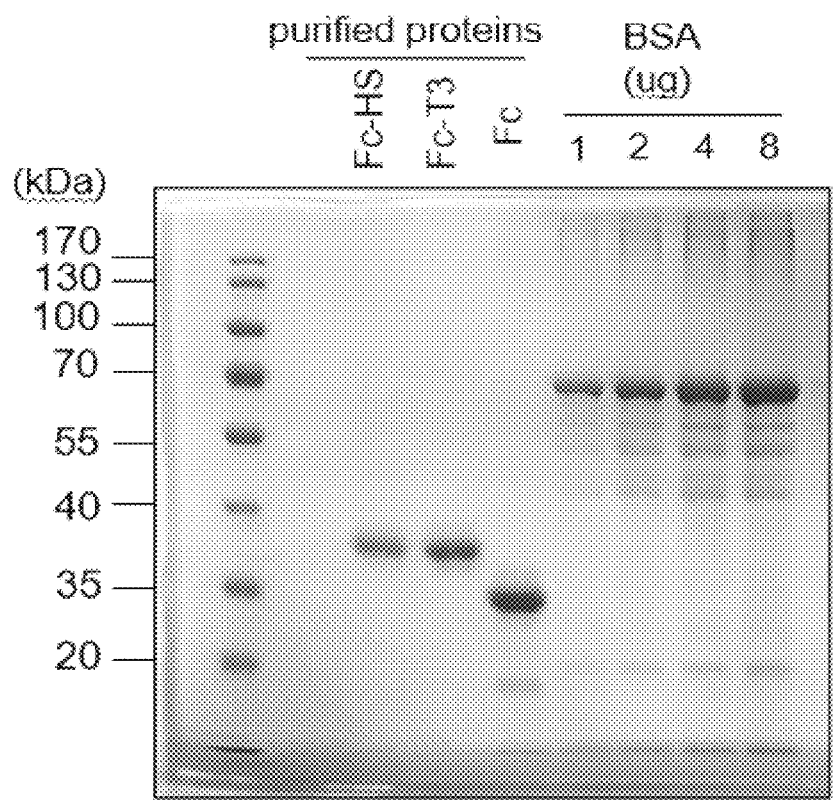

FIG. 9—Shows an SDS-PAGE gel demonstrating expression of purified Fc-HS and Fc-T3 proteins.

Figure 10:
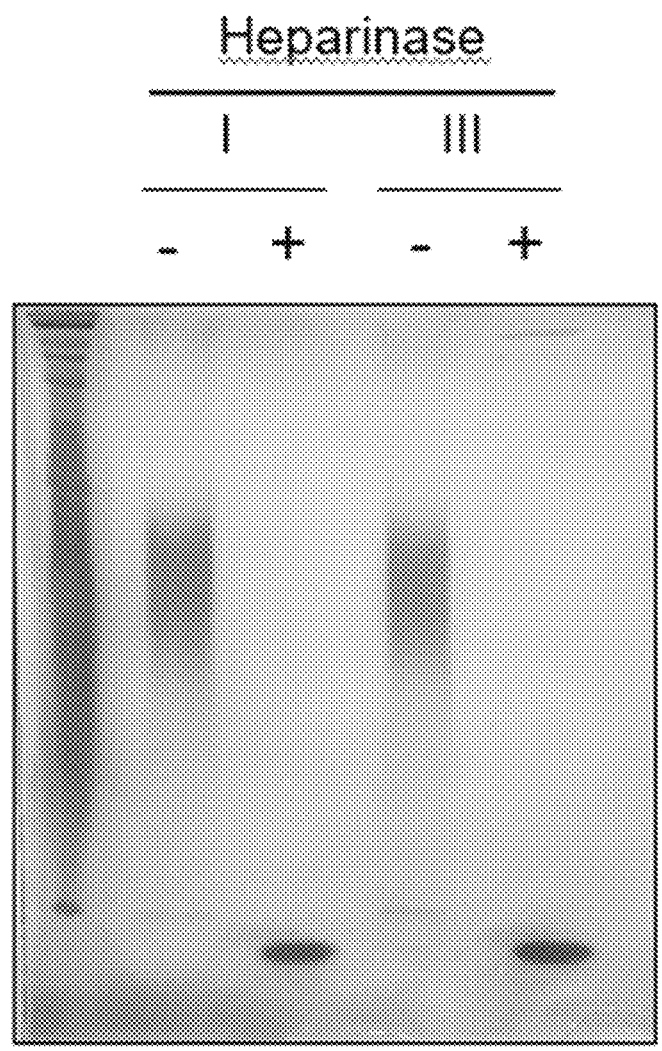

FIG. 10—Shows an SDS-PAGE gel demonstrating cleavage of heparin. Heparin was digested with enzymes at 30° C. for 24 h, analyzed by 20% SDS-PAGE, and visualized by Alcian blue/Silver staining.

Figure 11:
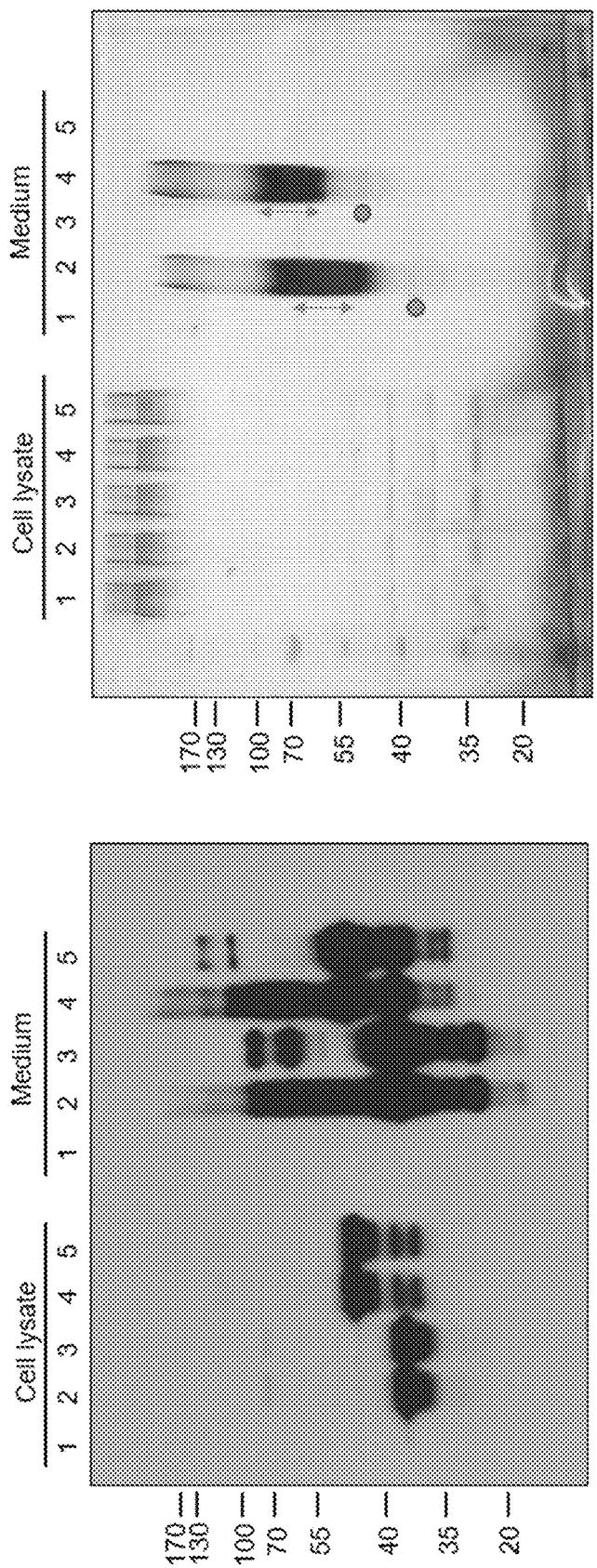

FIG. 11—Shows GAG-glycosylation of mock (control), pFc-HS, pFc-T3, pCD81-Fc-HS, and pCD81-Fc-T3. Sample 1: Mock; Sample 2: pFc-HS; Sample 3: pFc-T3; Sample 4: pCD81-Fc-HS; Sample 5: pCD81-Fc-T3. Left side shows western blot analysis. DNA samples were transfected into 293T cells. Cell lysates (5 µl of 400 µl total) and conditioned media (5 µl of 50 µl total) were captured by Protein-A beads, boiled in SDS gel buffer with DTT, and subjected to 10% SDS-PAGE. Western blot analysis was performed using Anti-human IgG Fc-HRP. Right side shows GAG-proteins stained with alcian blue/silver. DNA was transfected into 293T cells. Cell lysates (5 µl of 400 µl total) and conditioned media (5 µl of 50 µl total) were captured by Protein-A beads, boiled in SDS gel buffer with DTT, and subjected to 10% SDS-PAGE. Gel was visualized with alcian blue/silver staining. Slow migrating diffuse bands represent GAG. Blue dots indicate the size of the unglycosylated protein, and double-sided arrows indicate GAG-glycosylated protein. Each protein is found in cell lysate and culture medium. Only secreted proteins are GAG-glycosylated; glycosylation is coupled with the secretion pathway.

Figure 12:
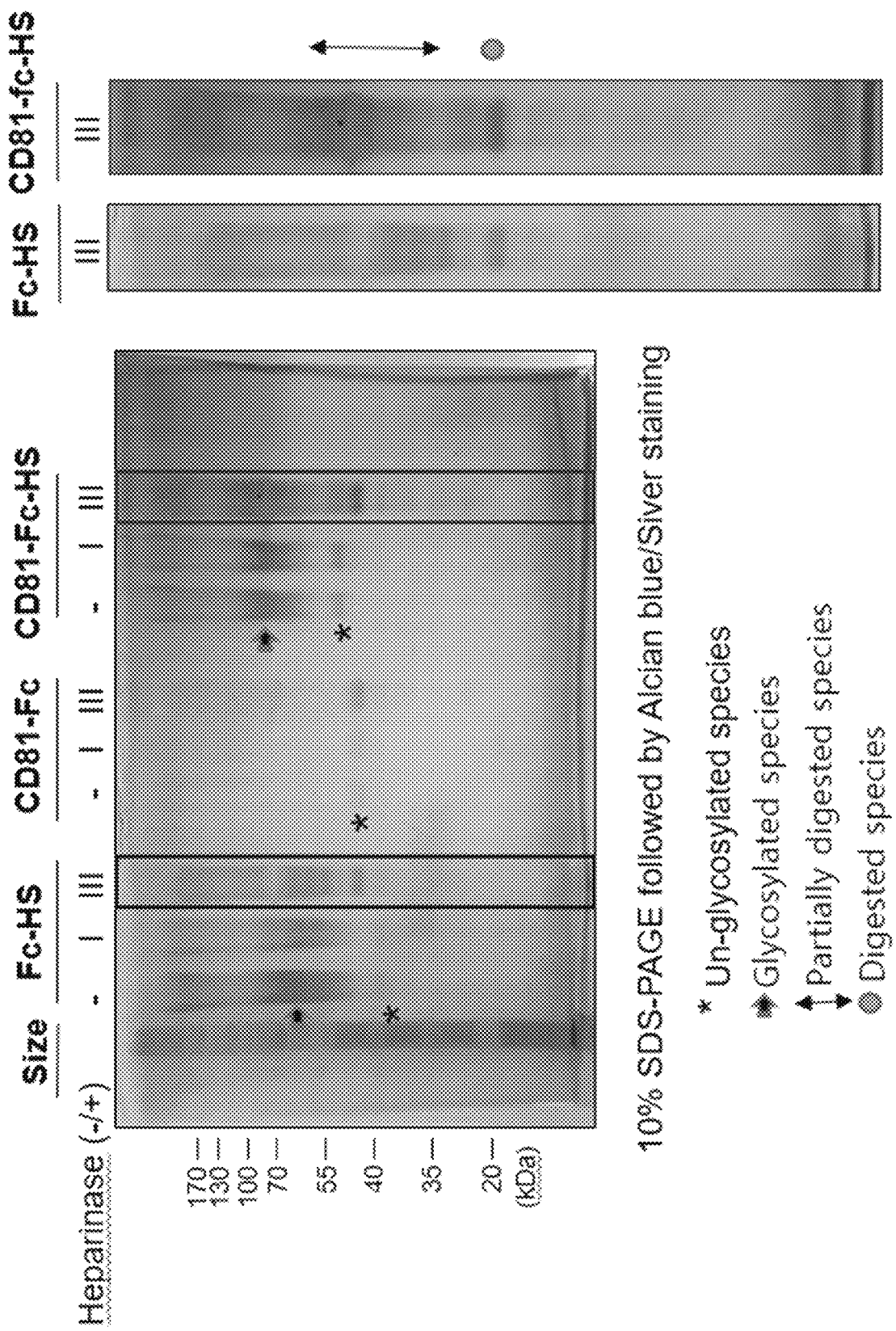

FIG. 12—Shows expression of HS in 293T cells digested with Heparinase I or Heparinase III. Secreted proteins in media were bound to Protein A beads and partially digested with Heparinase I or Heparinase III. Digested proteins were analyzed by 10% SDS-PAGE followed by alcian blue/silver staining to visualize GAG glycoproteins.

Figure 13:
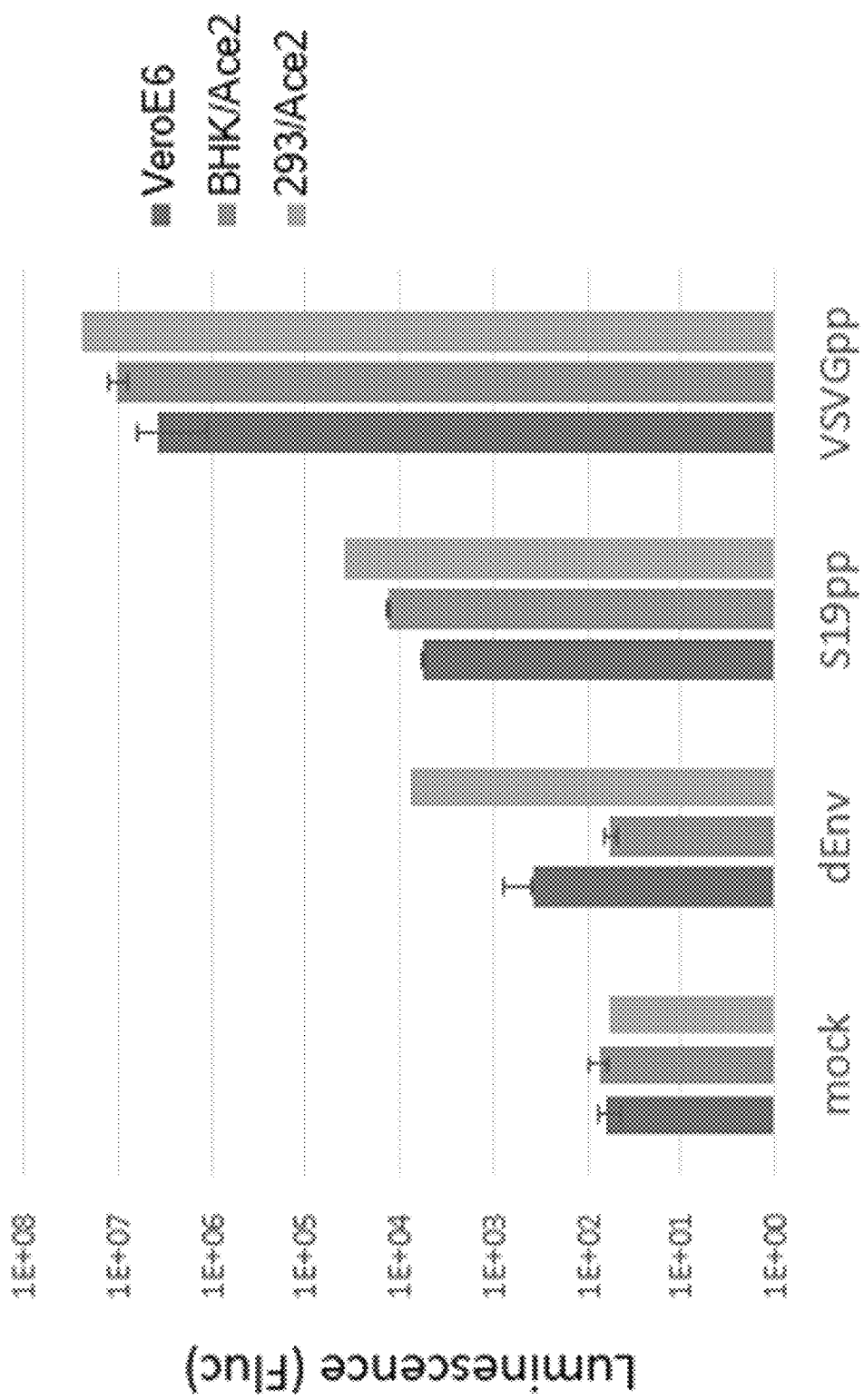

FIG. 13—Shows luminescence of retrovirus (murine leukemia virus, MLV)-based SARS-CoV-2 pseudovirus particles (pp), referred to herein as MLV-Spp, used to infect VeroE6 cells, BHK cells expressing ACE2 (BHK/ACE2), and 293T cells expressing ACE2 (bottom left).

Figure 14:
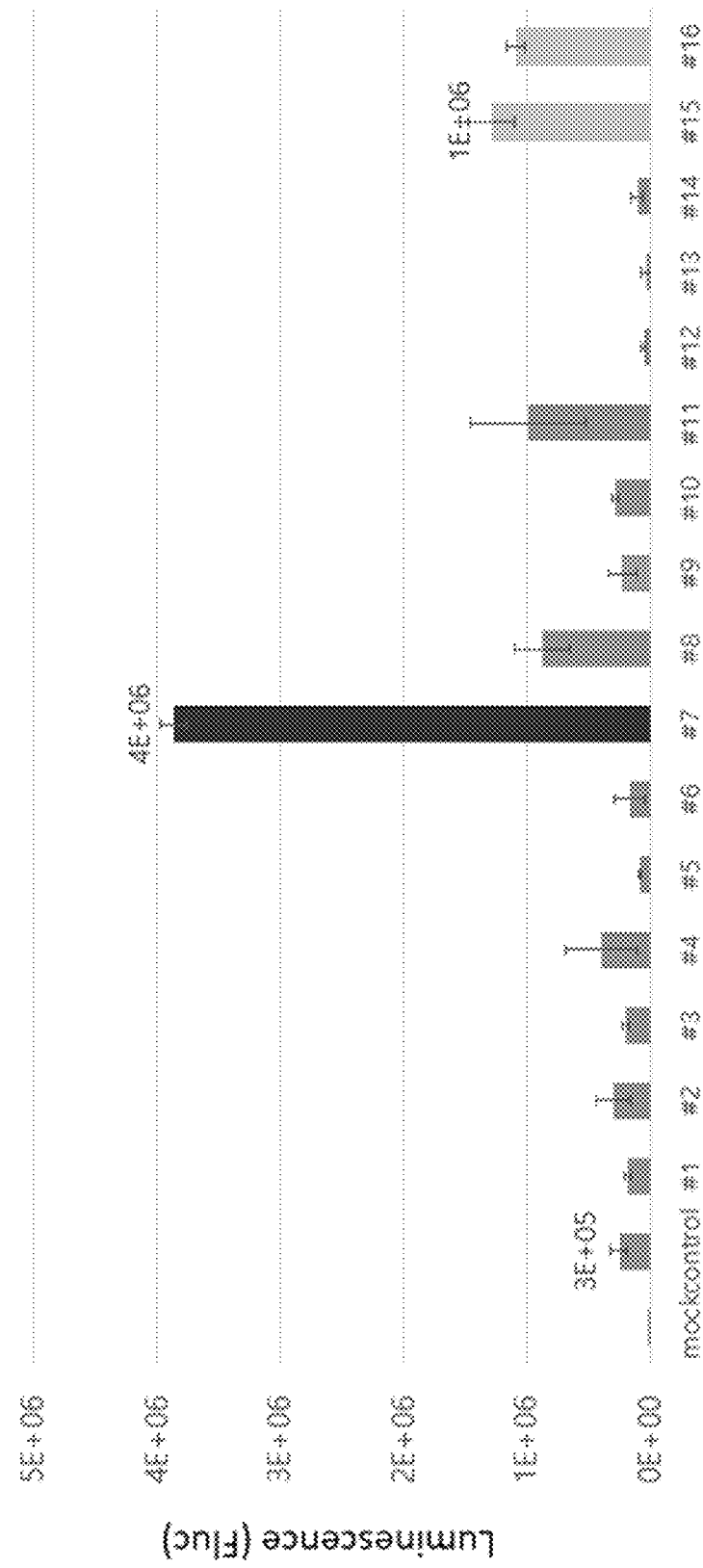

FIG. 14—Shows selection of stable target cell line for highly permissive infection of VeroE6 cells expressing TMPRSS2 by SARS-CoV-2.

Figure 15:
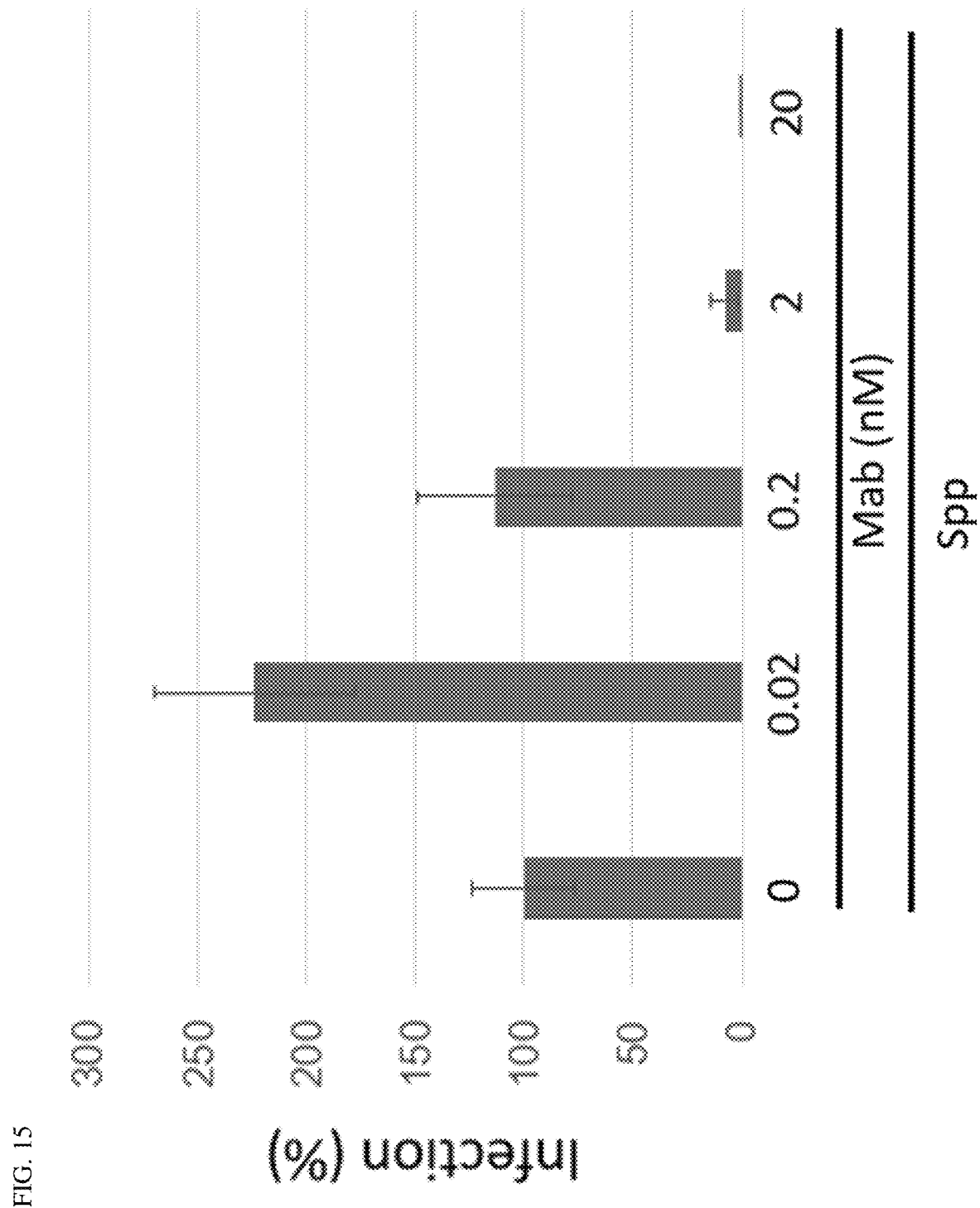

FIG. 15—Shows inhibition of SARS-CoV-2 pseudovirus infection by neutralizing monoclonal antibody.

Figure 16A:
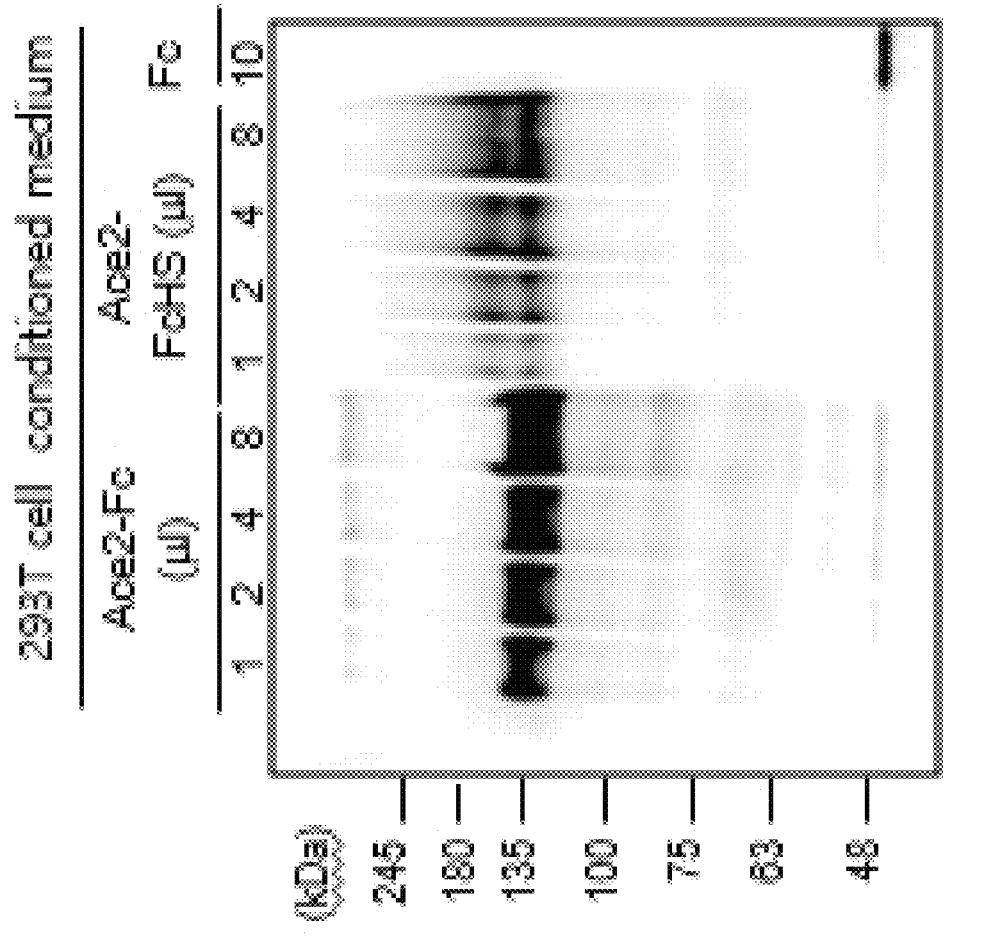
Figure 16B:
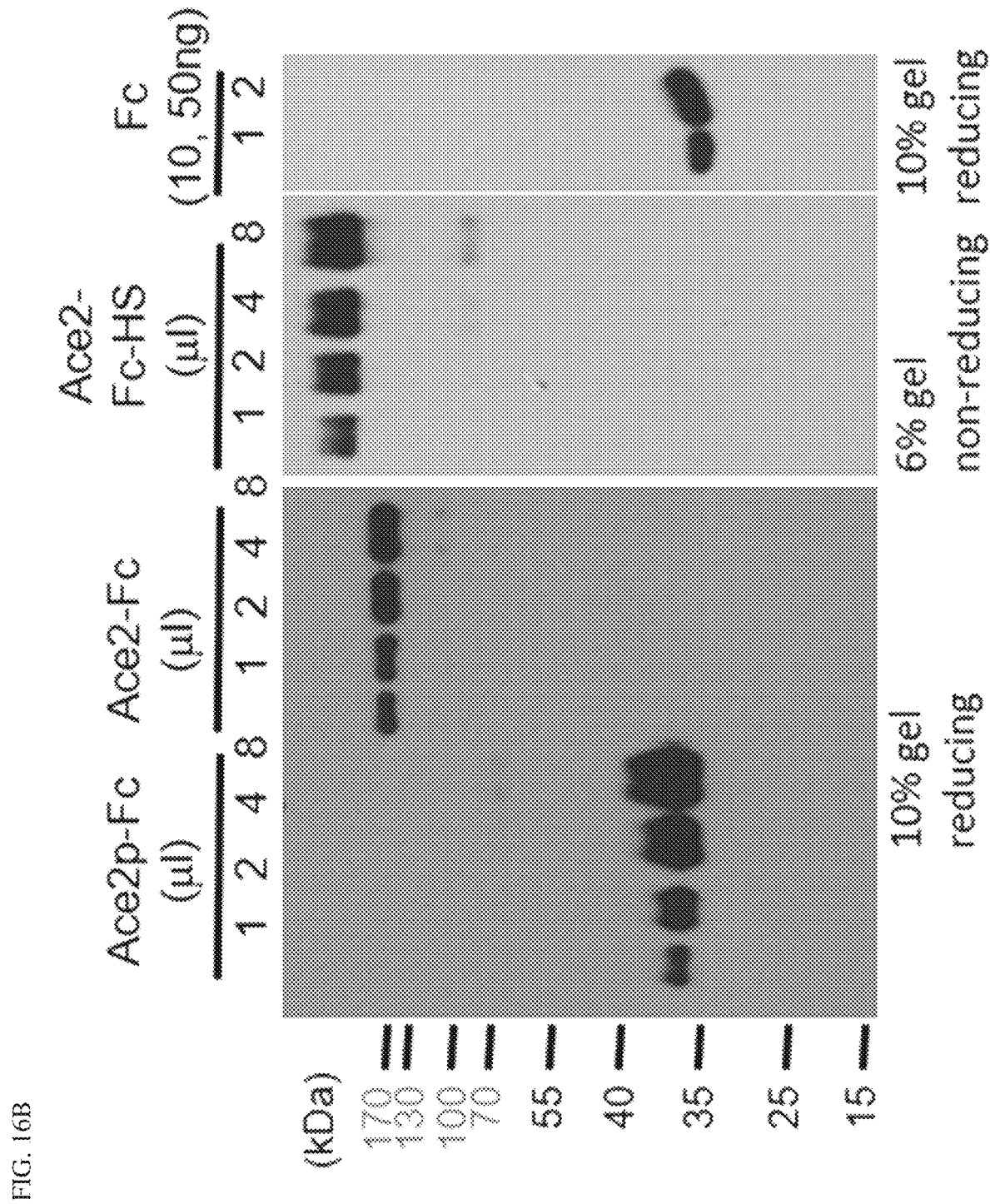

FIG. 16A and FIG. 16B—FIG. 16A shows an SDS-PAGE gel of a western blot demonstrating proteins Ace2-Fc and Ace2-Fc-HS expressed in 293T cells in cell culture medium. Proteins in increasing volume were electrophoresed in denaturing conditions. Western blot was probed with anti-human IgG-Fc. FIG. 16B shows an SDS-PAGE gel of a western blot demonstrating purification and characterization of proteins Ace2p6-Fc, Ace2-Fc, and Ace2-Fc-HS expressed in Huh7 cells. Purified proteins in increasing volume were electrophoresed in denaturing conditions. Western blot was probed with anti-human IgG-Fc.

Figure 17A:
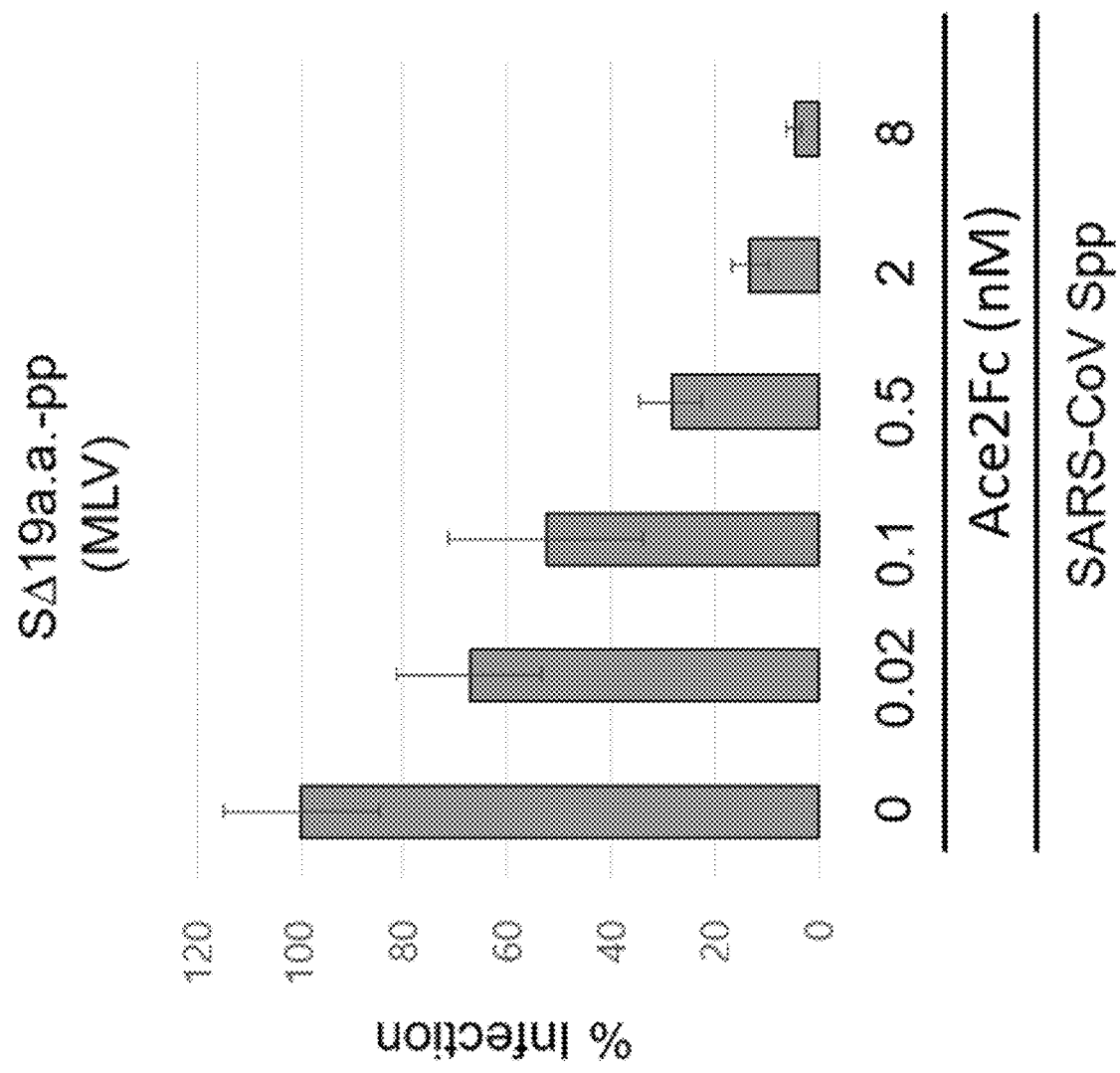
Figure 17B:
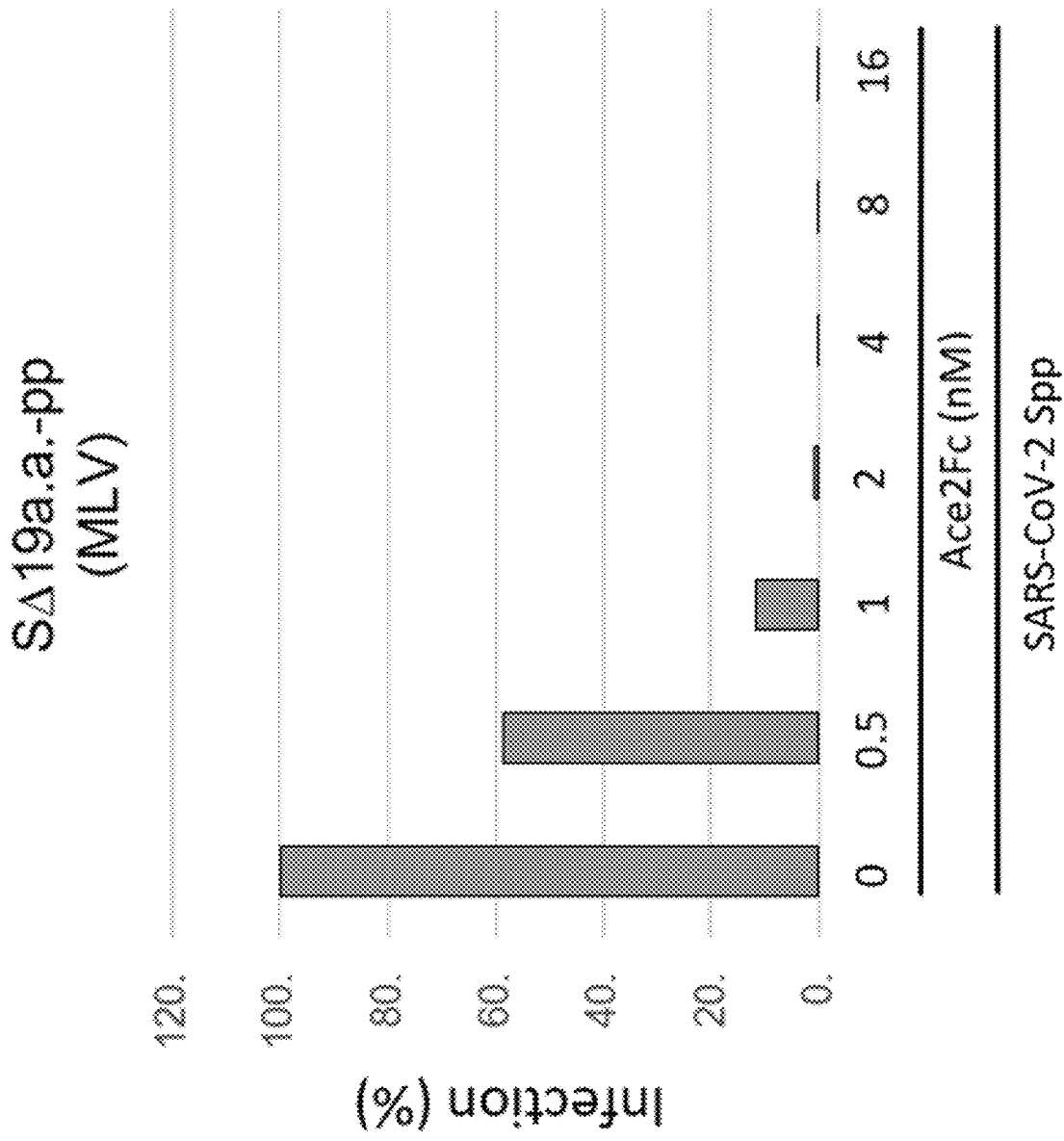

FIG. 17A and FIG. 17B—FIG. 17A shows inhibition of SARS-CoV pseudovirus entry by ACE2-Fc on VeroE6/TMPRSS2 cells measured by Luc activity. FIG. 17B shows SARS-CoV-2 pseudovirus (Spp) entry by ACE2-Fc on VeroE6/TMPRSS2 cells measured by Luc activity.

Figure 18A:
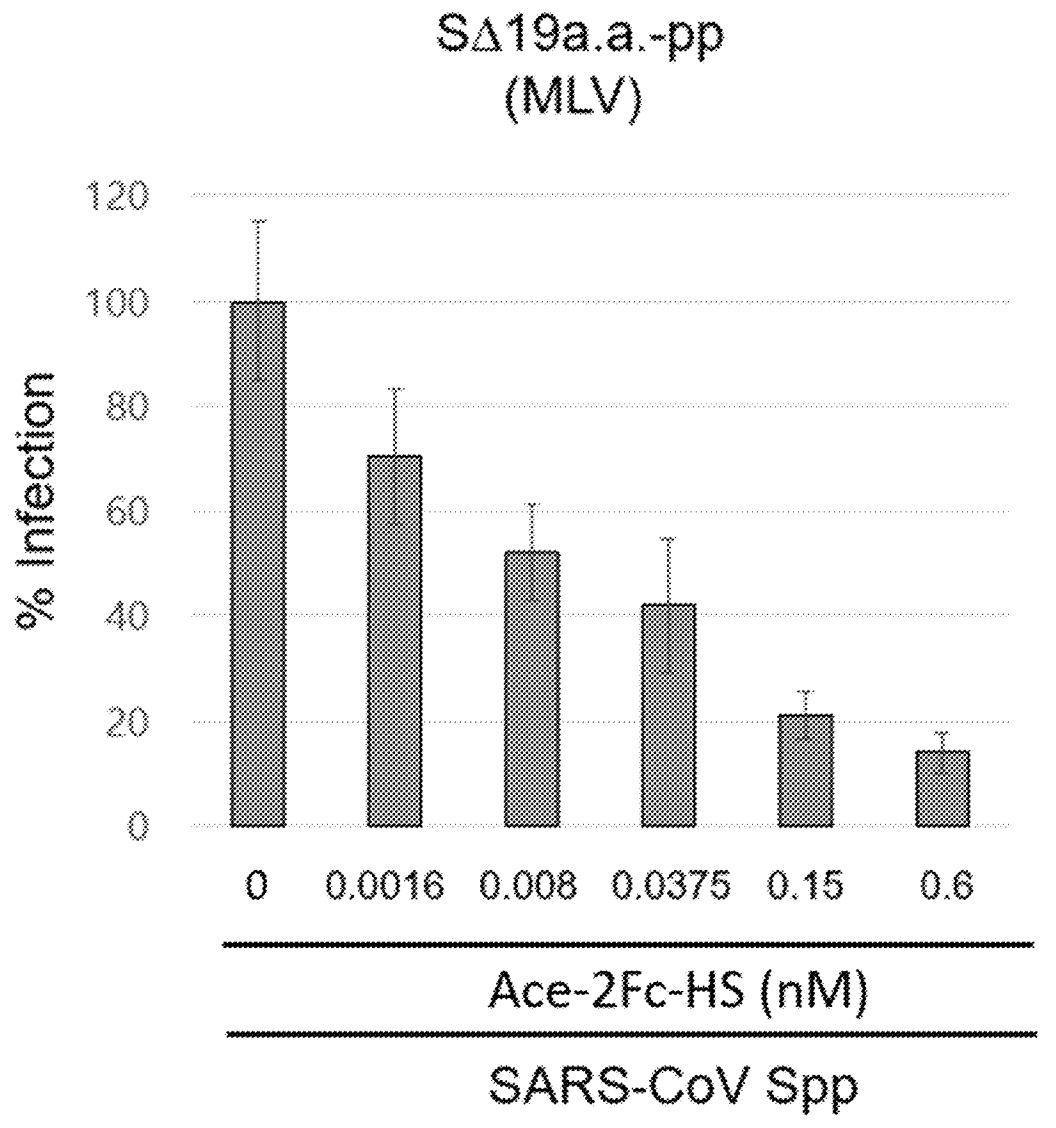
Figure 18B:
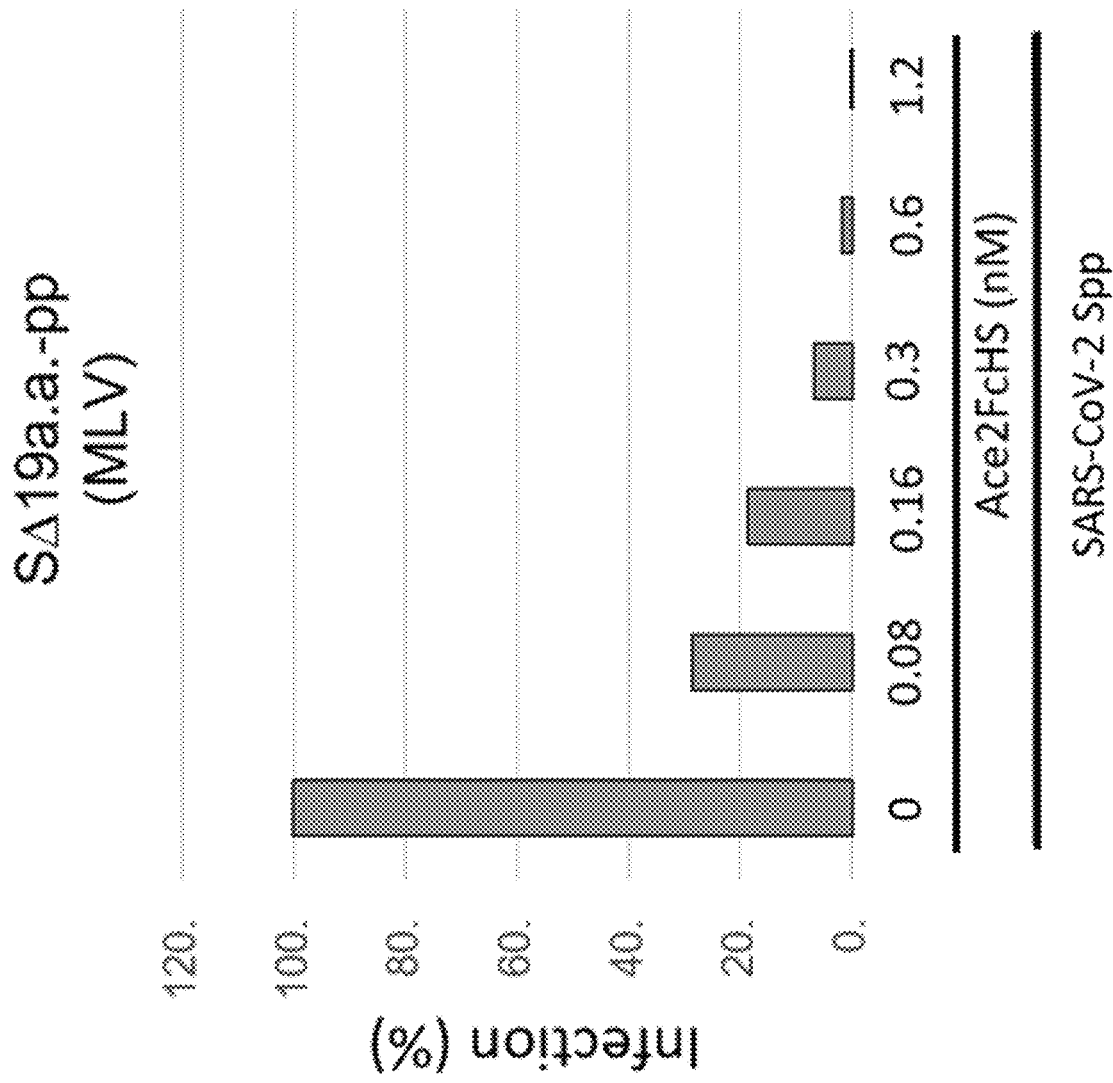

FIG. 18A and FIG. 18B—FIG. 18A shows inhibition of SARS-CoV pseudovirus entry by ACE2-Fc-HS on VeroE6/TMPRSS2 cells measured by Luc activity. FIG. 18B shows inhibition of SARS-CoV-2 pseudovirus entry by ACE2-Fc-HS on VeroE6/TMPRSS2 cells measured by Luc activity.

Figure 19A:
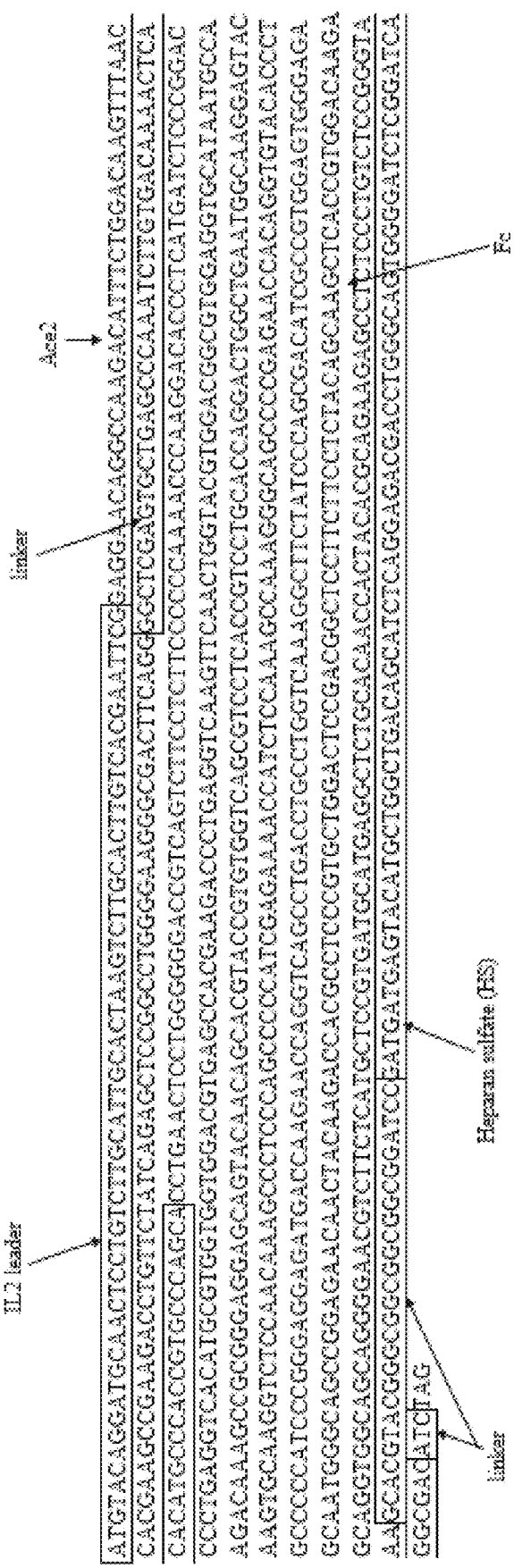
Figure 19B:
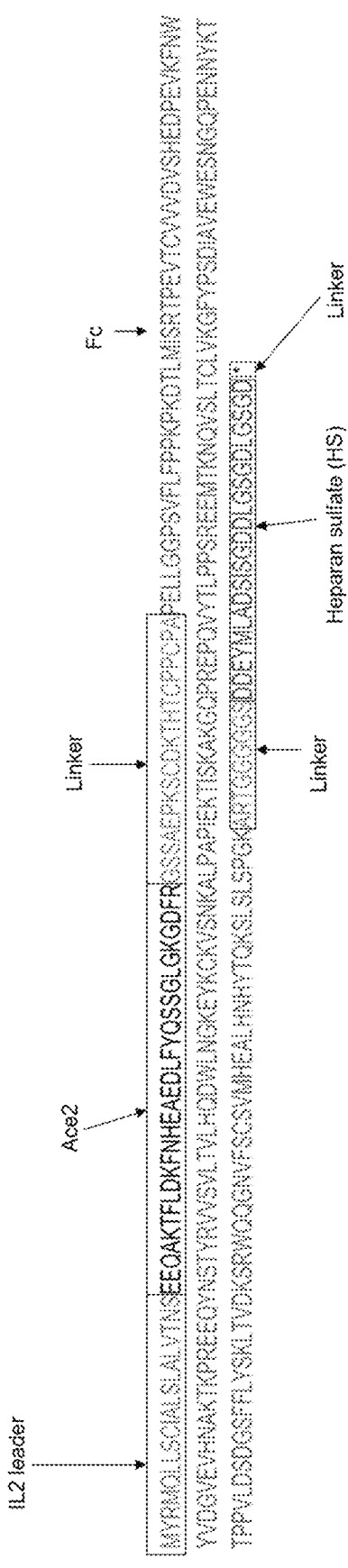

FIG. 19A and FIG. 19B—FIG. 19A shows the sequence of P6Fc-HS (complete sequence, corresponding to SEQ ID NO:24, 966 bp, and containing (in order) IL-2 leader (SEQ ID NO:25), ACE2 (SEQ ID NO:26), linker 1 (SEQ ID NO:27), Fc portion (SEQ ID NO:28), linker 2 (SEQ ID NO:29), and heparan sulfate proteoglycan core protein (SEQ ID NO:30). FIG. 19B shows the amino acid sequence of P6Fc-HS, corresponding to SEQ ID NO:31.

Figure 20A:
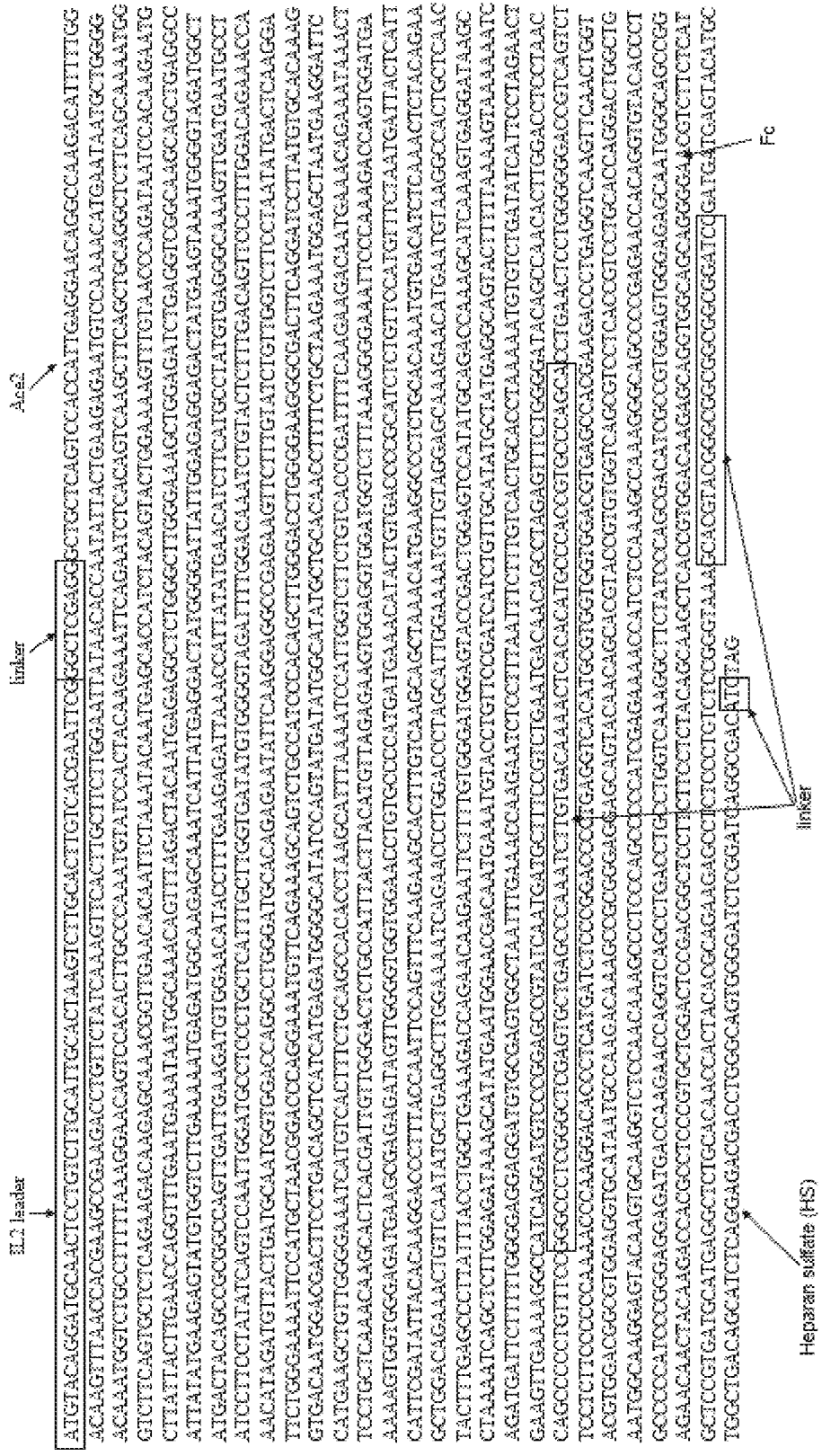
Figure 20B:
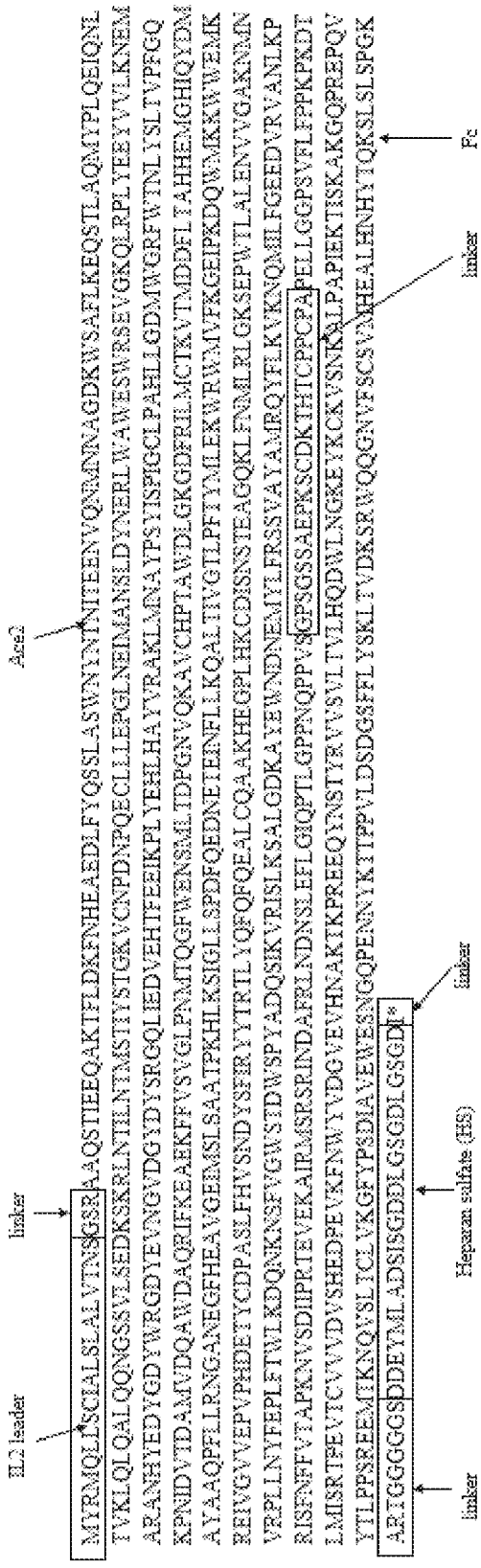

FIG. 20A and FIG. 20B—FIG. 20A shows the sequence of Ace2Fc-HS (complete sequence, corresponding to SEQ ID NO:32, 3066 bp, and containing (in order) IL-2 leader (SEQ ID NO:25), linker 1 (SEQ ID NO:34), ACE2 (SEQ ID NO:35), linker 2 (SEQ ID NO:36), Fc (SEQ ID NO:28), linker 3 (SEQ ID NO:38), and heparan sulfate proteoglycan core protein (SEQ ID NO:30). FIG. 20B shows the amino acid sequence of Ace2Fc-HS, corresponding to SEQ ID NO:37.

Figure 21A:
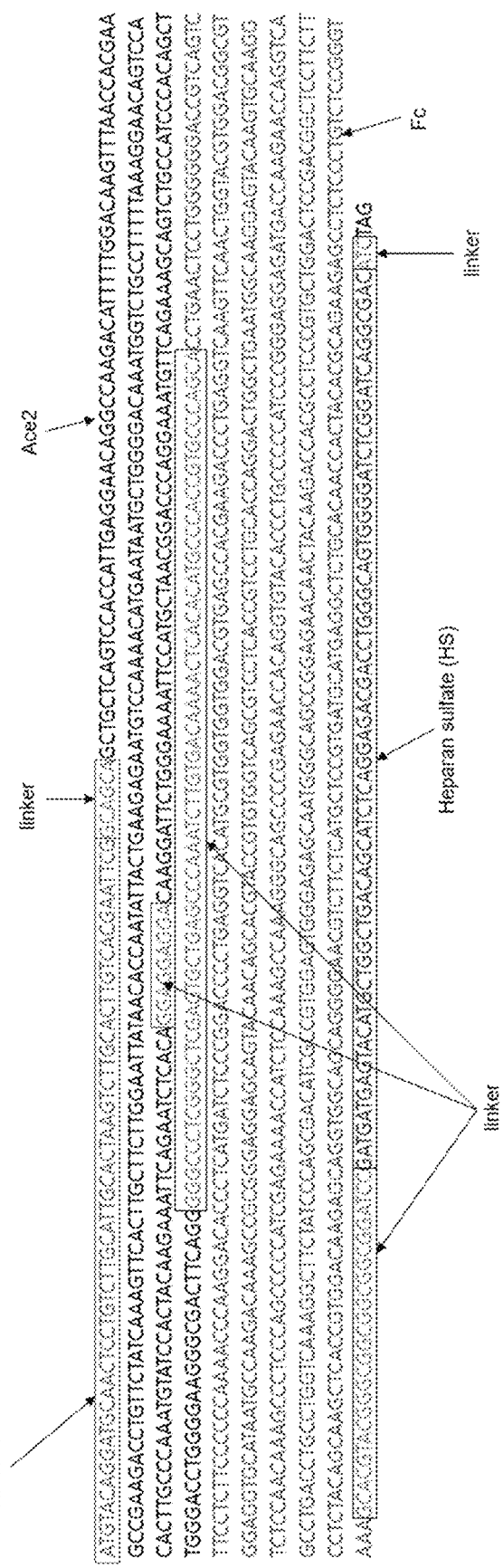
Figure 21B:
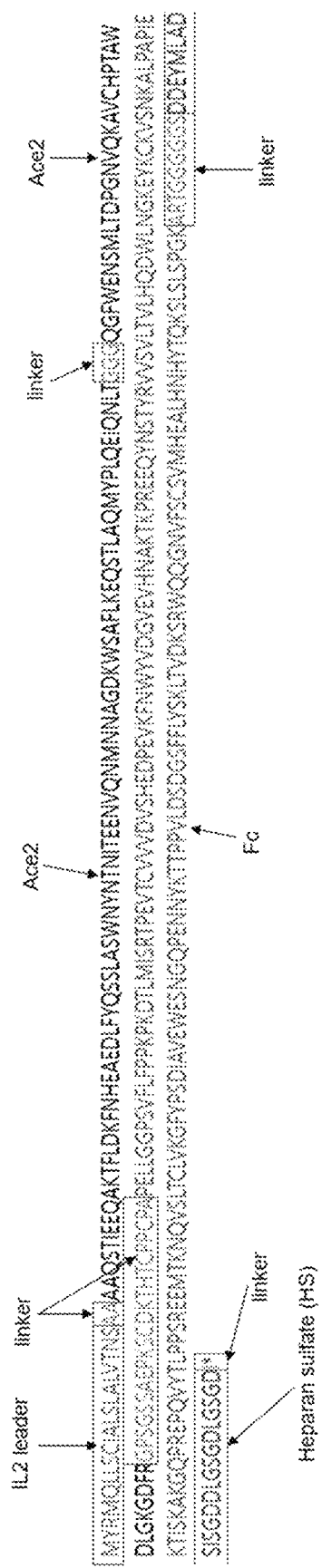

FIG. 21A and FIG. 21B—FIG. 21A shows the sequence of P61Fc-HS (complete sequence, corresponding to SEQ ID NO:38, 1128 bp, and containing (in order) IL-2 leader (SEQ ID NO:25), linker 1 (SEQ ID NO:39), ACE2-1 portion (SEQ ID NO:40), linker 2 (SEQ ID NO:41), ACE2-2 portion (SEQ ID NO:42), linker 3 (SEQ ID NO:43), Fc (SEQ ID NO:28), linker 4 (SEQ ID NO:44), and heparan sulfate proteoglycan core protein (SEQ ID NO:30). FIG. 21B shows the amino acid sequence of P61Fc-HS, corresponding to SEQ ID NO:45.

Figure 22:
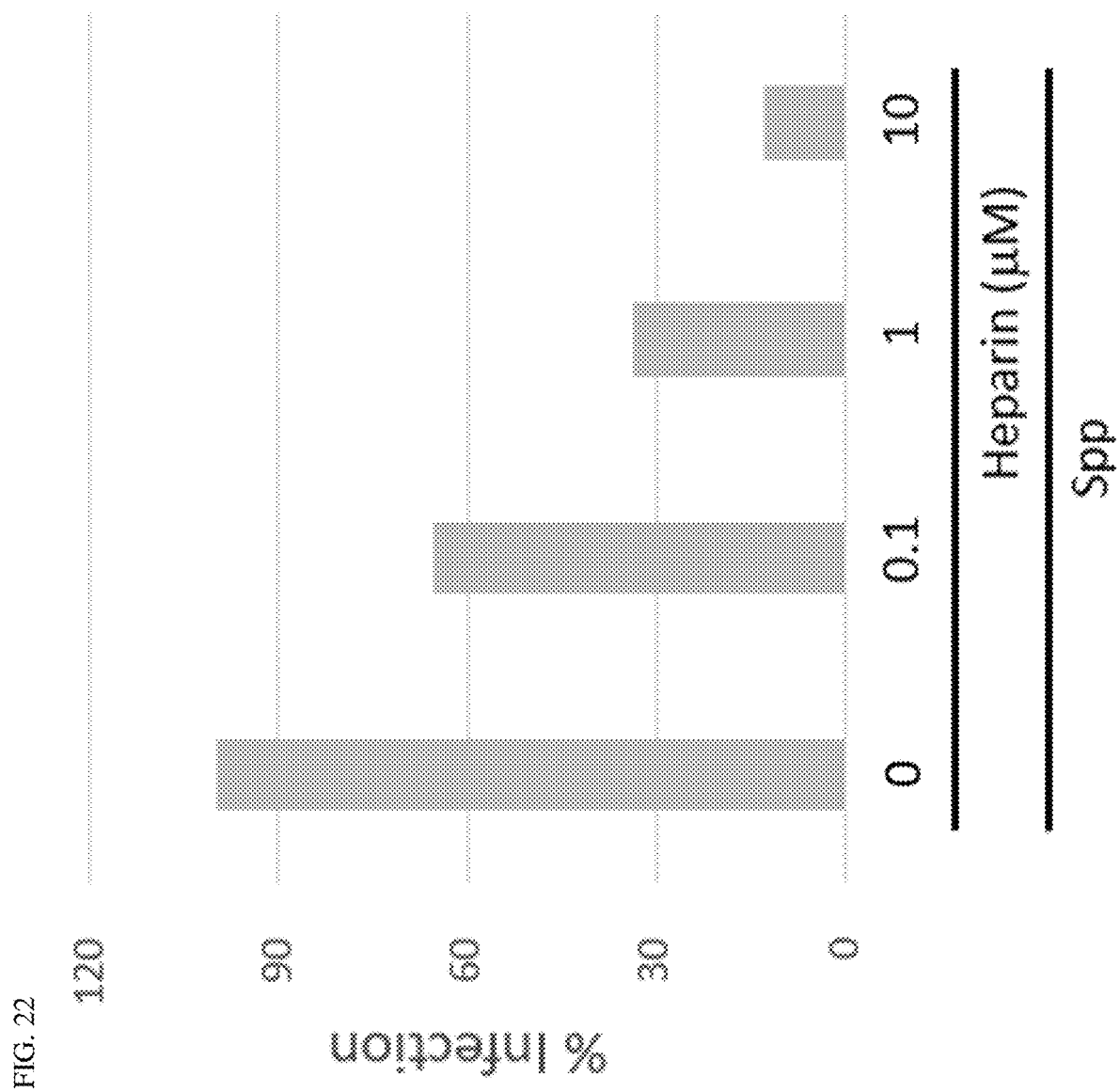

FIG. 22—Shows inhibition of SARS-CoV-2 pseudovirus entry to VeroE6/TMmPRSSprss2 cells when combined with increasing concentrations of heparin.

Figure 23:
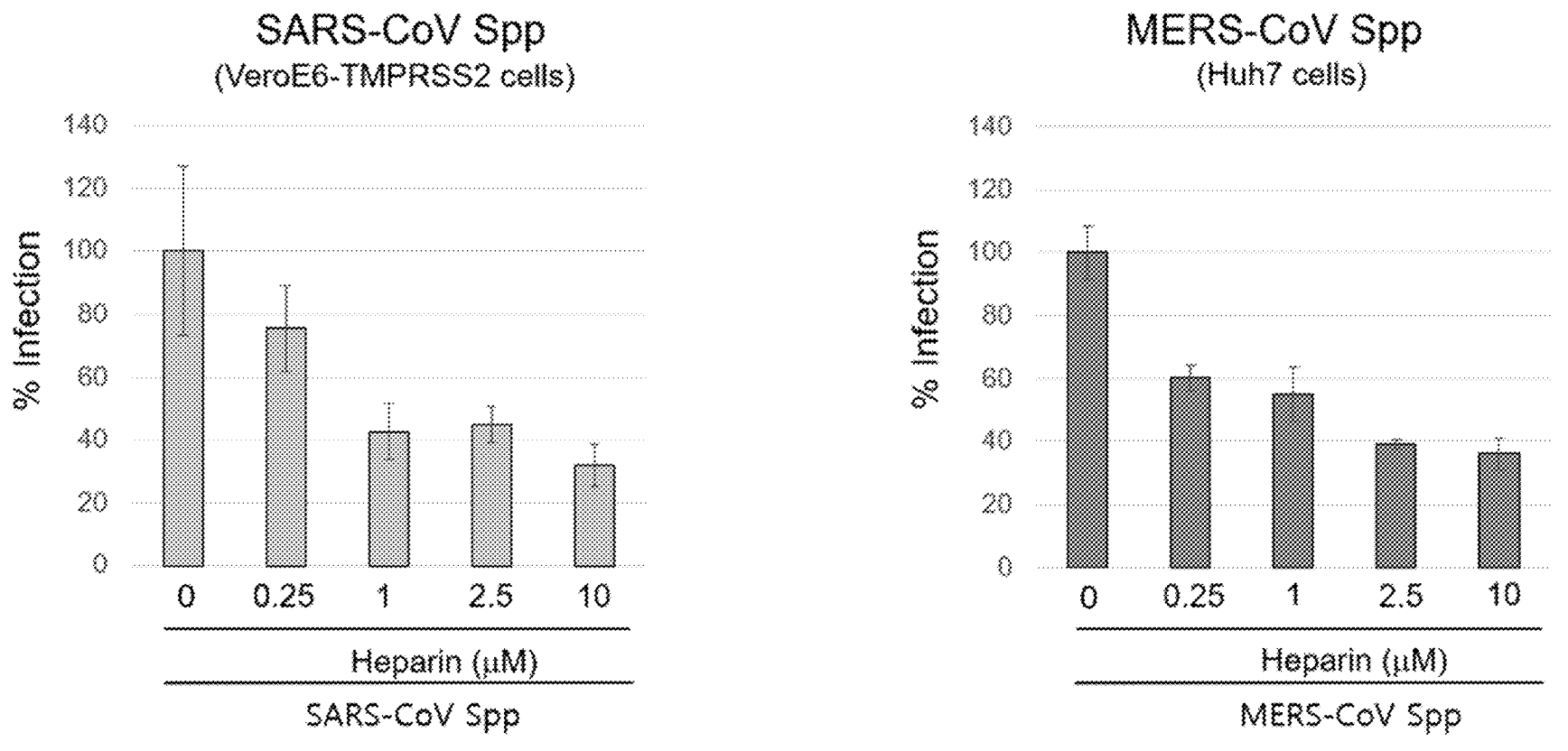

FIG. 23—Shows inhibition of SARS-CoV pseudovirus infection in VeroE6 cells (left) and MERS-CoV pseudovirus infection in Huh7 cells (right) when combined with increasing concentrations of heparin, measured by Luc activity.

Figure 24:
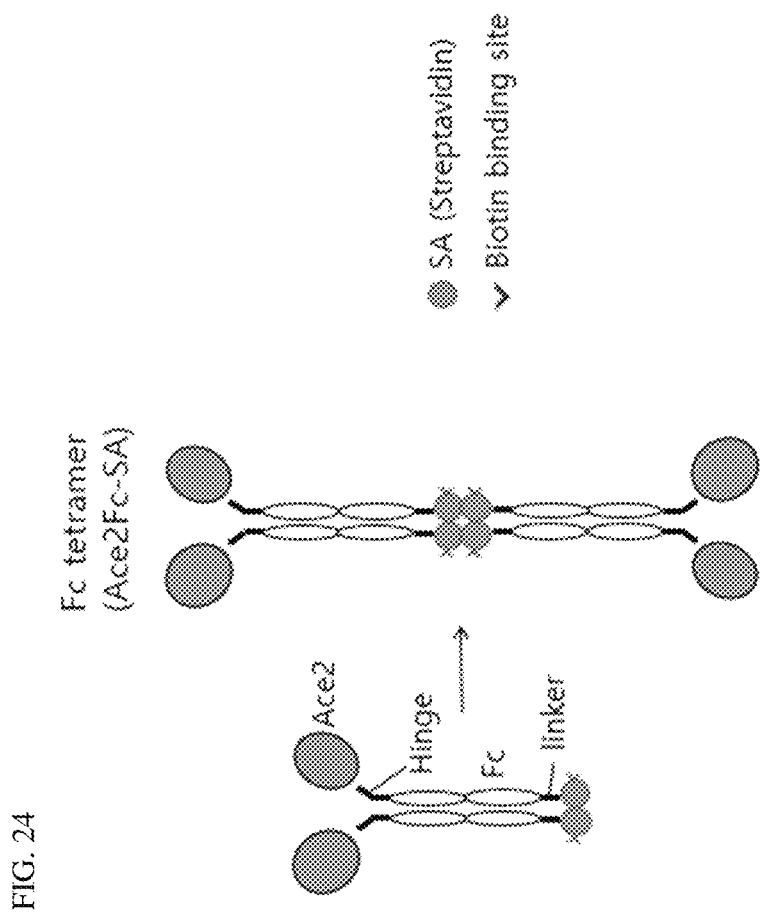

FIG. 24—Shows a schematic depicting tetramerization of ACE2 in ACE2-Fc using streptavidin (SA) and biotin.

Figure 25:
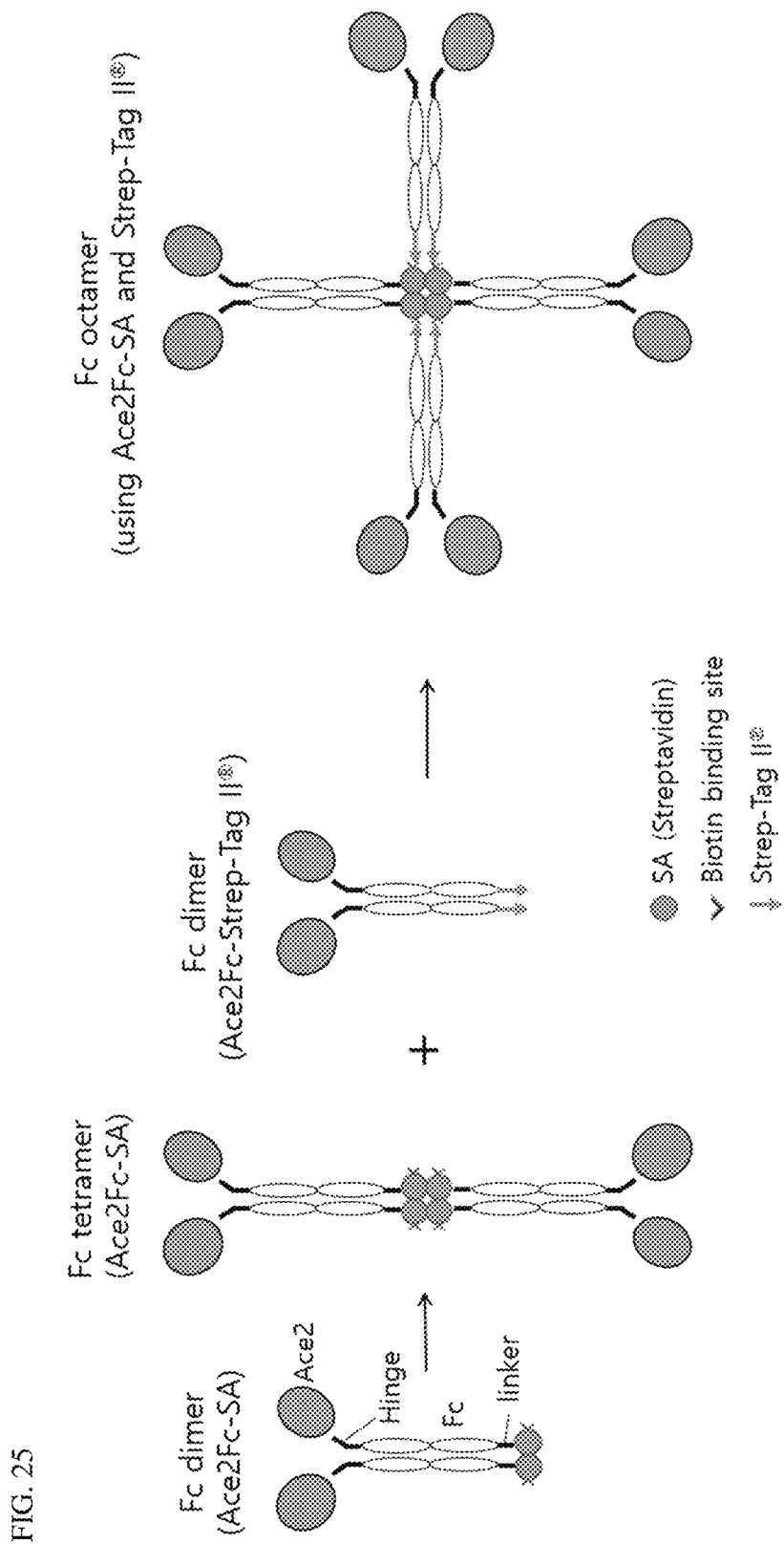

FIG. 25—Shows a schematic depicting octamerization of ACE2 in ACE2-Fc using streptavidin (SA) and biotin.

Figure 26:
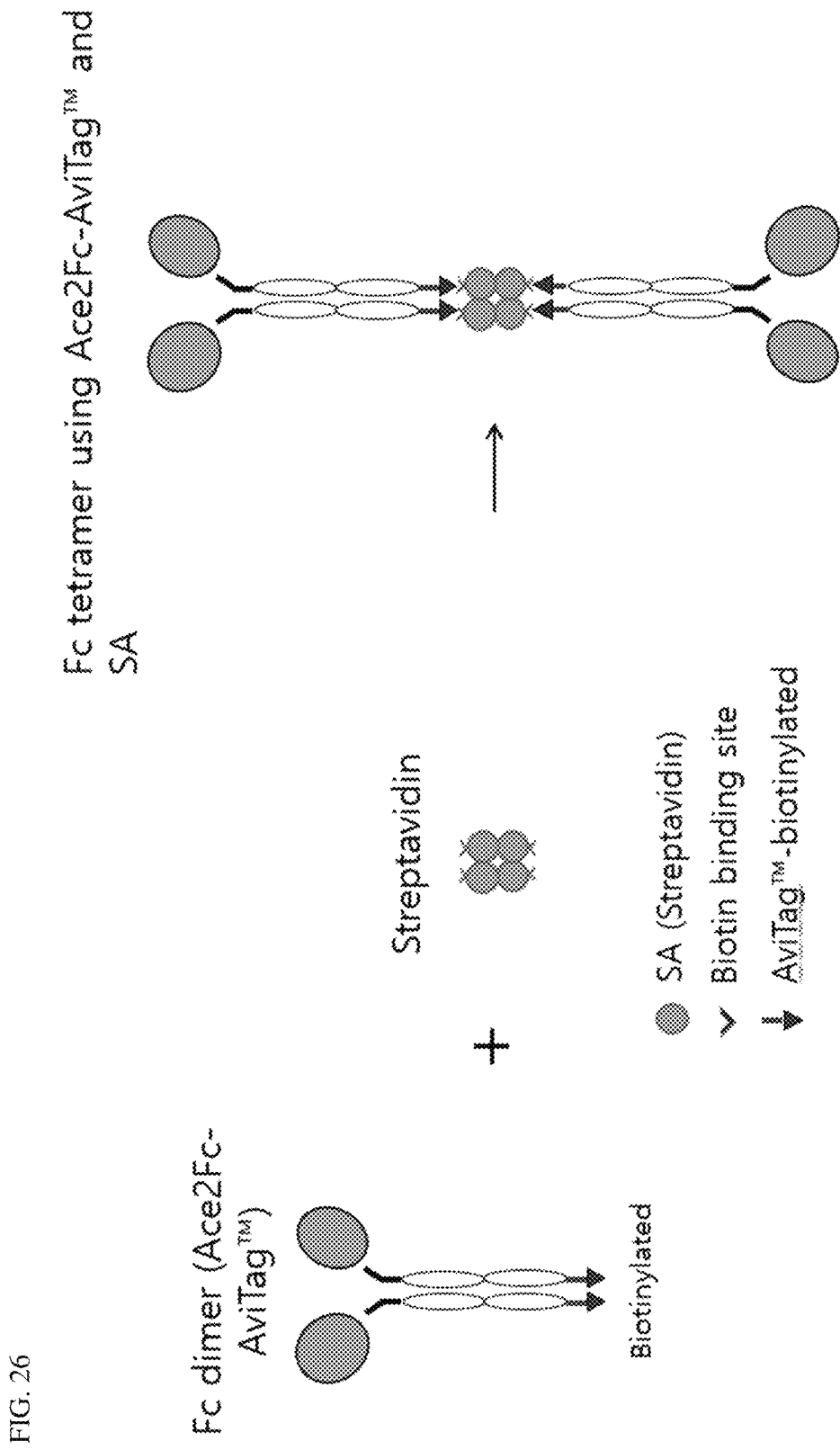

FIG. 26—Shows a schematic depicting tetramerization of ACE2 in ACE2-Fc using streptavidin (SA) and biotinylated AviTag™.

Figure 27:
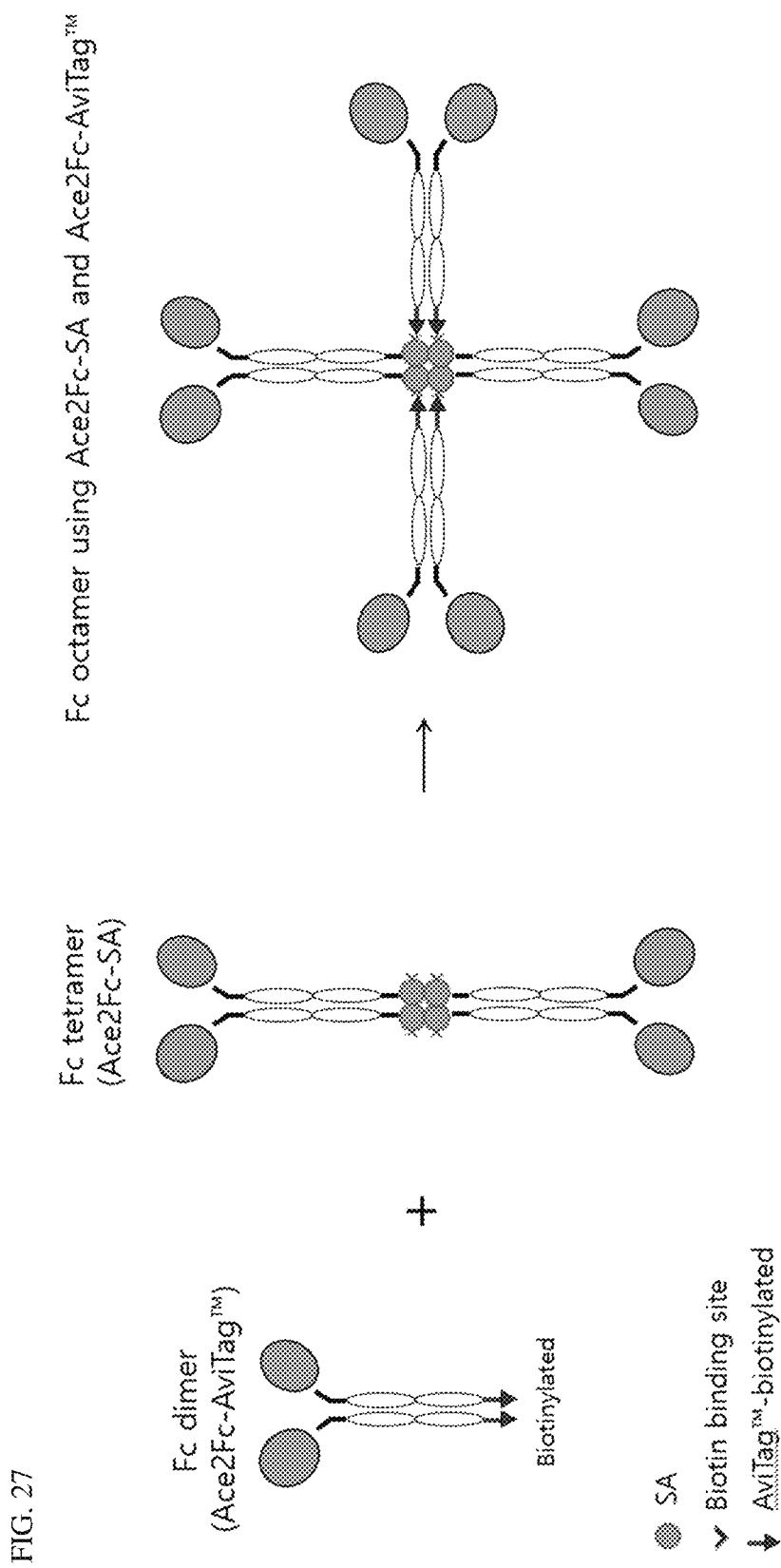

FIG. 27—Shows a schematic depicting octamerization of ACE2 in ACE2-Fc using streptavidin (SA) and biotinylated AviTag™.

Figure 28:
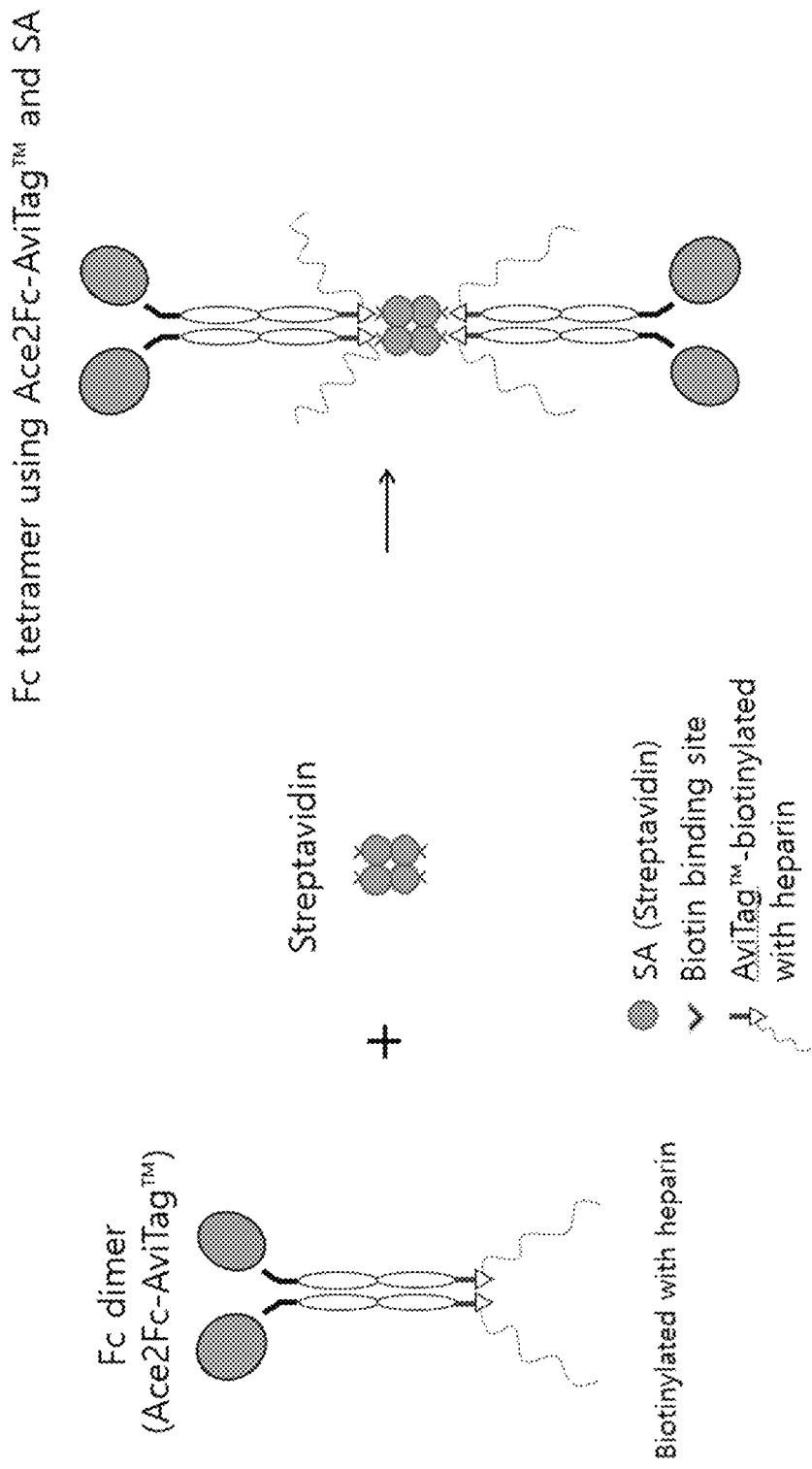

FIG. 28—Shows a schematic depicting tetramerization of ACE2 in ACE2-Fc using streptavidin (SA) and AviTag™ biotinylated with heparin.

Figure 29:
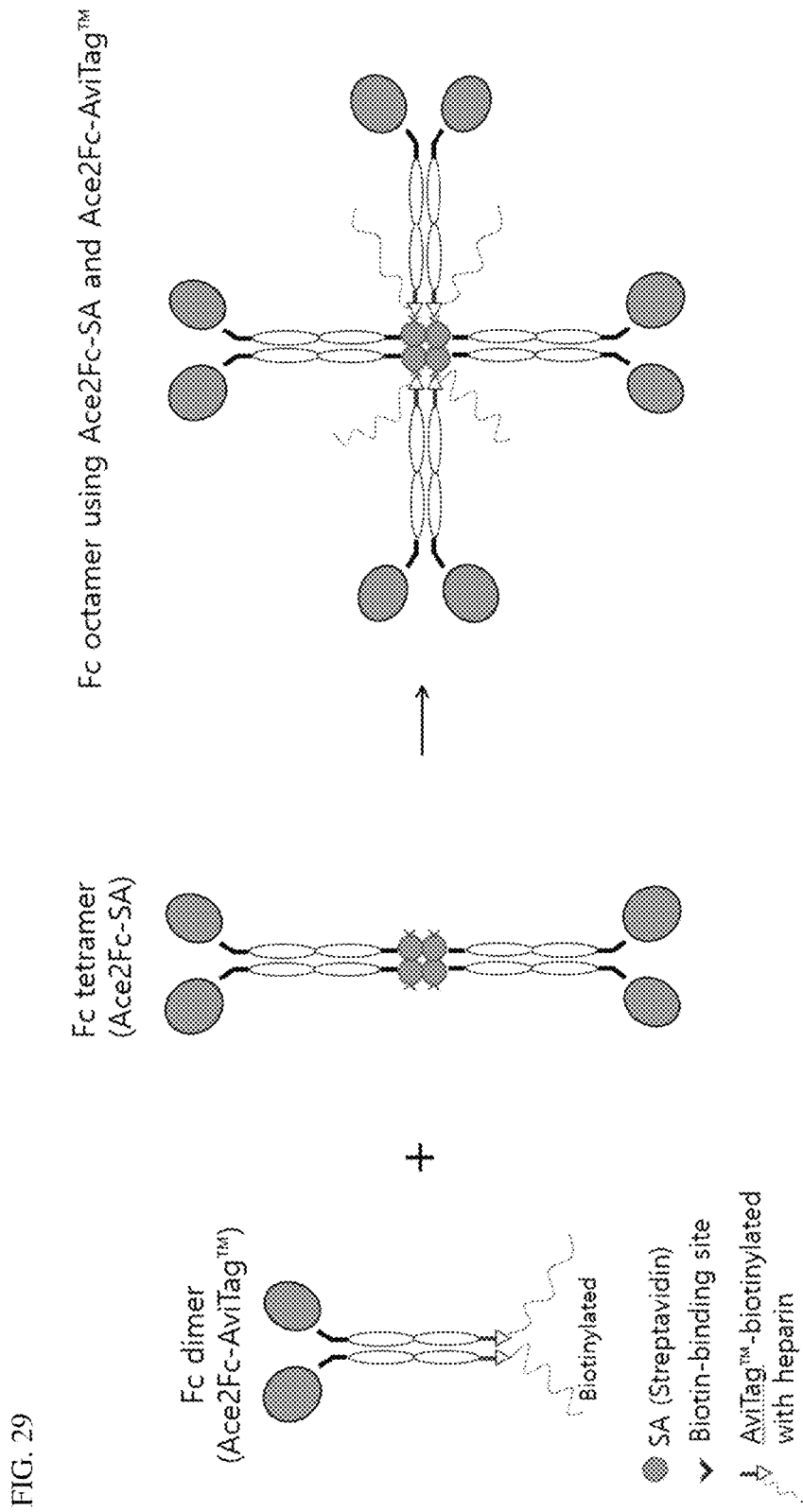

FIG. 29—Shows a schematic depicting octamerization of ACE2 in ACE2-Fc using streptavidin (SA) and AviTag™ biotinylated with heparin.

Figure 30A:
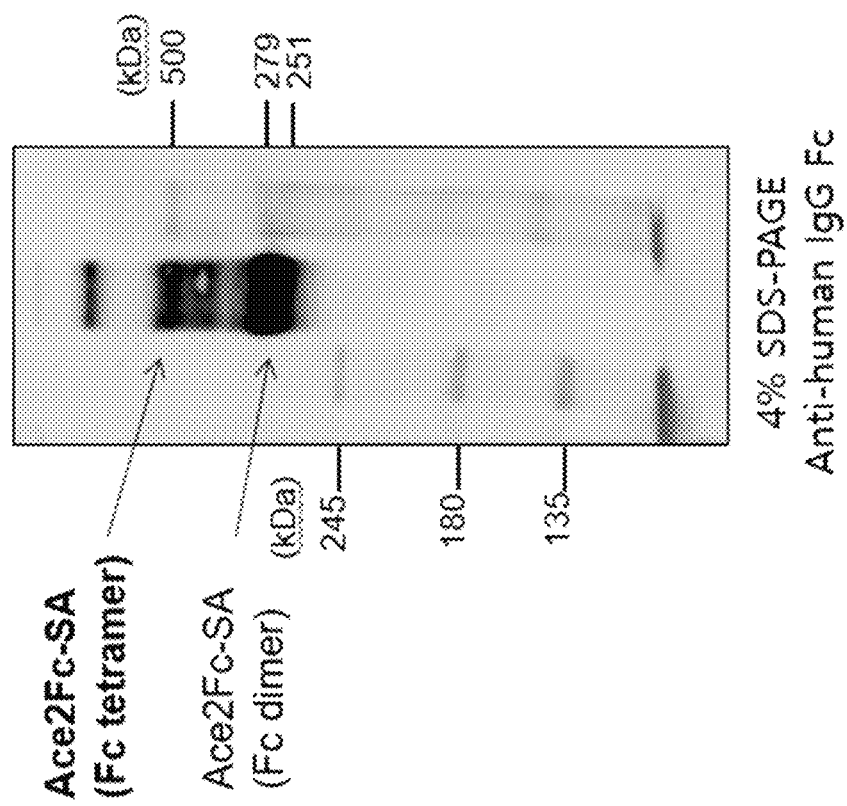
Figure 30B:
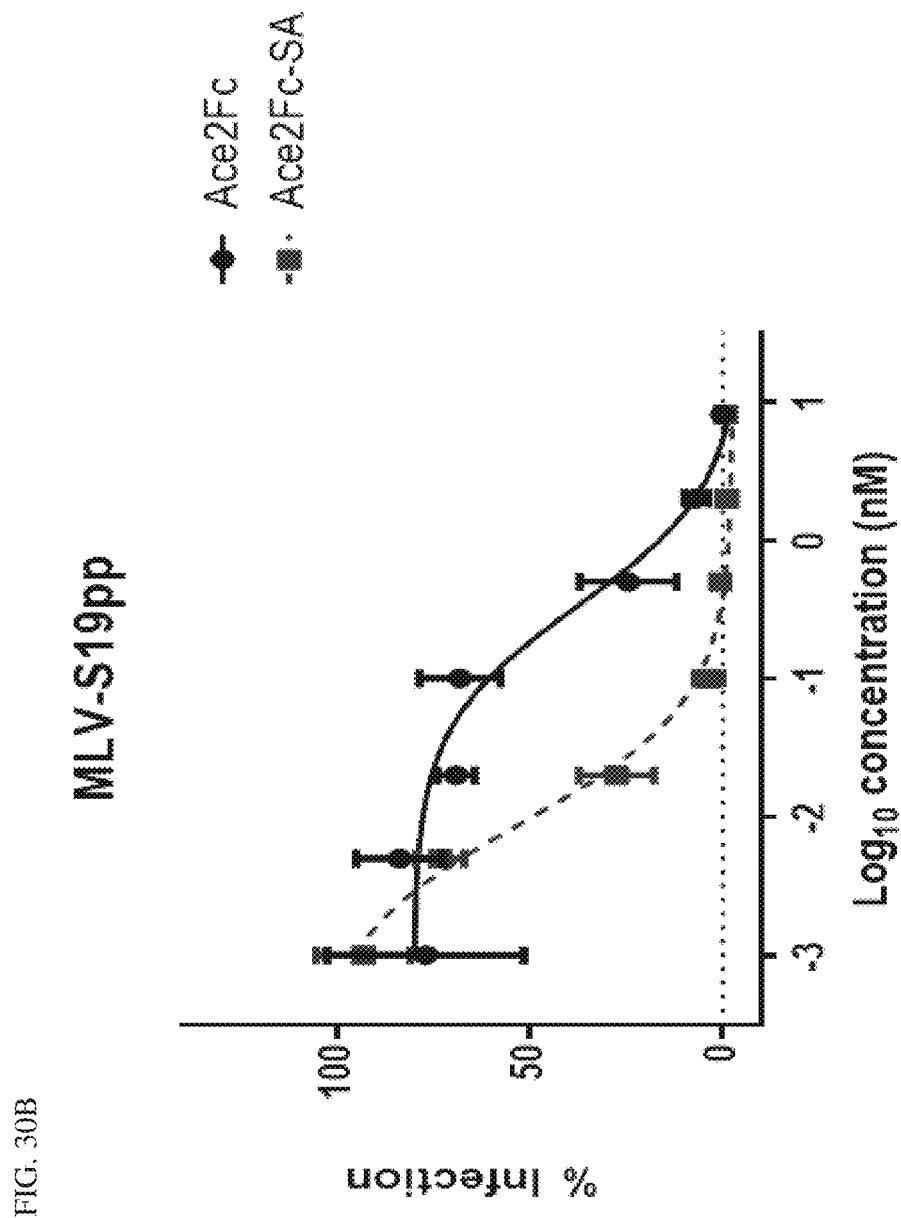

FIG. 30A and FIG. 30B—FIG. 30A shows expression of ACE2-Fc-SA in dimeric and tetrameric ACE2 in cells, partially denatured by SDS. FIG. 30B shows inhibition of SARS-CoV-2 pseudovirus infection in VeroE6/TMPRSS2 cells by ACE2-Fc and ACE2-Fc-SA in ACE2 tetramer measured by Luc activity.

FIG. 31A and FIG. 31B—FIG. 31A shows the DNA sequence (corresponding to SEQ ID NO:46) of the ACE2-Fc-streptavidin recombinant polypeptide (Ace2Fc-SA). FIG. 31B shows the protein sequence (corresponding to SEQ ID NO:47). The IL2 leader is shown in capitalized underlined text; the linker is shown in lowercase, underlined, bold text; human ACE2 is shown in capitalized regular text; the Fc region is shown in capitalized, italicized text; streptavidin (SA) is shown in lowercase, italicized text.

FIG. 32A and FIG. 32B—FIG. 32A shows the DNA sequence (corresponding to SEQ ID NO:48) of the ACE2-Fc-AviTag™ recombinant polypeptide (Ace2Fc-AviTag™). FIG. 32B shows the protein sequence (corresponding to SEQ ID NO:49). The IL2 leader is shown in capitalized underlined text; the linker is shown in lowercase, underlined, bold text; human ACE2 is shown in capitalized regular text; the Fc region is shown in capitalized, italicized text; AviTag™ is shown in lowercase, italicized text.

FIG. 33A and FIG. 33B—FIG. 33A shows the DNA sequence (corresponding to SEQ ID NO:50) of the ACE2-Fc-Strep-Tag II® recombinant polypeptide (Ace2Fc-Strep-Tag®). FIG. 33B shows the protein sequence (corresponding to SEQ ID NO:51). The IL2 leader is shown in capitalized underlined text; the linker is shown in lowercase, underlined, bold text; human ACE2 is shown in capitalized regular text; the Fc region is shown in capitalized, italicized text; Strep-Tag II® is shown in lowercase, italicized text.

Figure 34:
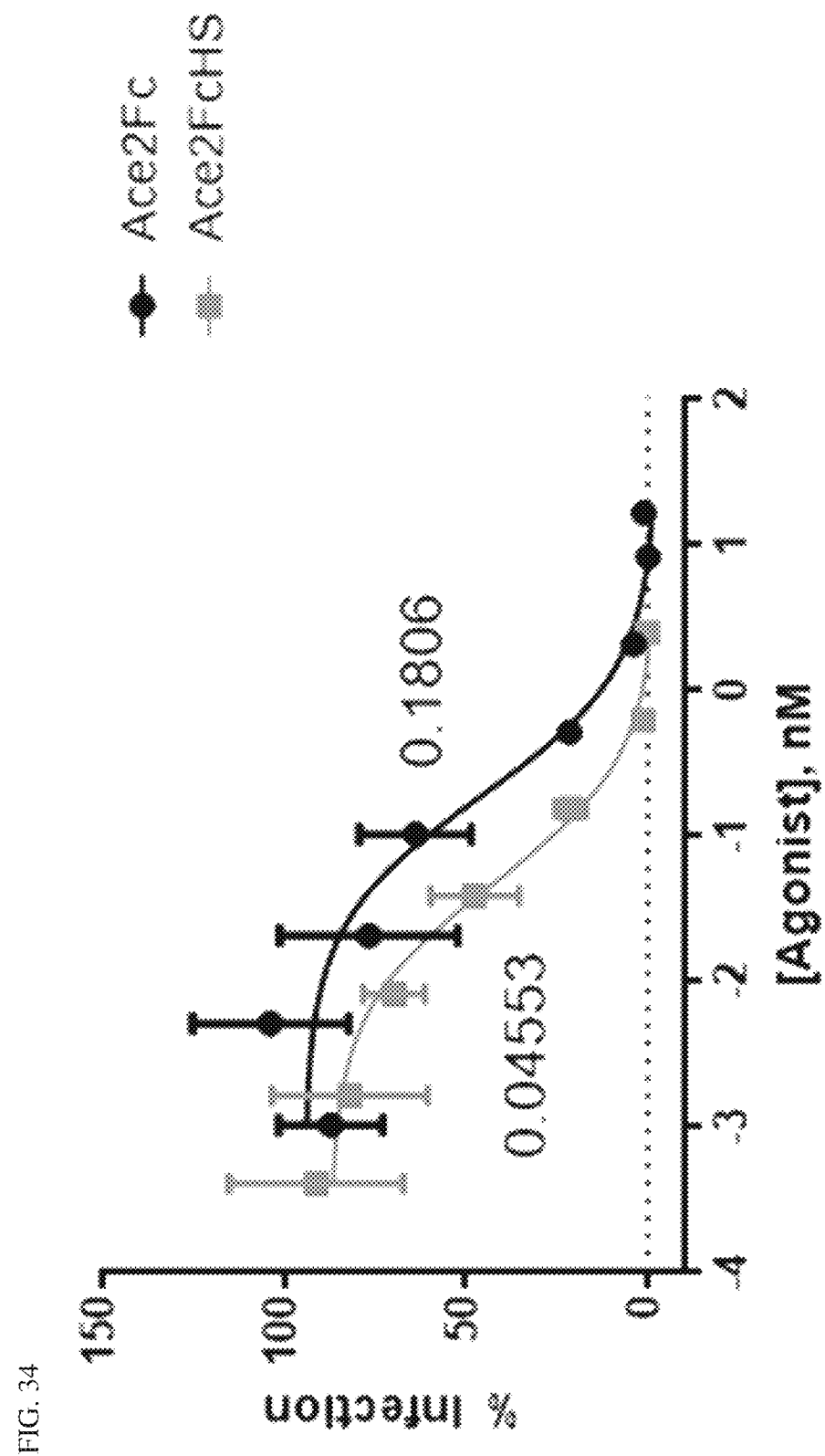

FIG. 34—Shows inhibition of infection of SARS-CoV-2 variant D614G by ACE2-Fc and ACE2-Fc-HS on VeroE6/TMPRSS2 cells.

BRIEF DESCRIPTION OF THE SEQUENCES

SEQ ID NO:1—Sequence of HS24 peptide containing 3 sulfation sites.
SEQ ID NO:2—Sequence of HS21 peptide containing 2 sulfation sites.
SEQ ID NO:3—Sequence of HS16 peptide containing 1 sulfation site.
SEQ ID NO:4—Sequence of human Ig k-chain leader.
SEQ ID NO:5—Sequence of IL-2 leader.
SEQ ID NO:6—Sequence of HUMAN CD5 Leader peptide, used in eCD4-Ig.
SEQ ID NO:7—Sequence of Human Ig k-chain leader.
SEQ ID NO:8—Sequence of IL-2 leader.
SEQ ID NO:9—Sequence of human CD5 Leader peptide, used in eCD4-Ig.
SEQ ID NO:10—Sequence of human SRB1 (CD36) extracellular domain, corresponding to amino acids 33-443 of the full-length sequence (see FIG. 6).
SEQ ID NO:11—Sequence of full-length sequence of human SRB1 (CD36) (see FIG. 6).
SEQ ID NO:12—Sequence of IgG-1 chain C region, *Homo sapiens*.
SEQ ID NO:13—Sequence of human Ig-Fc with hinge Fc(t) with 7 aa upstream.
SEQ ID NO:14—Sequence of CD81 human, full length (see FIG. 7).
SEQ ID NO:15—Sequence of CD81 extracellular domain (aa 113-201) (see FIG. 7).
SEQ ID NO:16—Sequence of full length HPSG2: Accession No. M85289; PUBMED 1569102.
SEQ ID NO:17—Sequence of HCV-AB68, anti HV-1 mAb, Vh fragment.
SEQ ID NO:18—Sequence of human perlecan GAG sites (amino acids 52-79), with LDLR A1 (amino acids 198-235); UniProtKB-P98160 (PGBM_HUMAN).
SEQ ID NO:19—Sequence of a T7 promoter.
SEQ ID NO:20—Amino acid sequence of HS proteoglycan peptide present in Fc-HS, obtained from Perlecan.
SEQ ID NO:21—Amino acid sequence of T3 present in Fc-T3.
SEQ ID NO:22—Amino acid HS proteoglycan peptide from Glypican 5.
SEQ ID NO:23—Amino acid HS proteoglycan peptide from Syndecan 4.
SEQ ID NO:24—Nucleotide sequence of P6Fc-HS (complete sequence, 966 bp, shown in FIG. 19A), containing (in order) IL-2 leader (SEQ ID NO:25), ACE2 (SEQ ID NO:26), linker 1 (SEQ ID NO:27), Fc (SEQ ID NO:28), linker 2 (SEQ ID NO:29), and heparan sulfate proteoglycan core protein (SEQ ID NO:30).
SEQ ID NO:25—Sequence of IL-2 leader.
SEQ ID NO:26—Sequence of ACE2 in P6Fc-HS.
SEQ ID NO:27—Sequence of linker 1 in P6Fc-HS.
SEQ ID NO:28—Sequence of Fc.
SEQ ID NO:29—Sequence of linker 2 in P6Fc-HS.
SEQ ID NO:30—Sequence of heparan sulfate proteoglycan core protein.
SEQ ID NO:31—Amino acid sequence of P6Fc-HS (corresponding to SEQ ID NO:24, shown in FIG. 19B).
SEQ ID NO:32—Nucleotide sequence of Ace2Fc-HS (complete sequence, 3066 bp, shown in FIG. 20A), containing (in order) IL-2 leader (SEQ ID NO:25), linker 1 (SEQ ID NO:33), ACE2 (SEQ ID NO:34), linker 2 (SEQ ID NO:35), Fc (SEQ ID NO:28), linker 3 (SEQ ID NO:36), and heparan sulfate proteoglycan core protein (SEQ ID NO:30).
SEQ ID NO:33—Sequence of linker 1 in Ace2Fc-HS.
SEQ ID NO:34—Sequence of ACE2 in Ace2Fc-HS.
SEQ ID NO:35—Sequence of linker 2 in Ace2Fc-HS.
SEQ ID NO:36—Sequence of linker 3 in Ace2Fc-HS.
SEQ ID NO:37—Amino acid sequence of Ace2Fc-HS (corresponding to SEQ ID NO:32, shown in FIG. 20B).
SEQ ID NO:38—Nucleotide sequence of P61Fc-HS (complete sequence, 1128 bp, shown in FIG. 21A), containing (in order) IL-2 leader (SEQ ID NO:25), linker 1 (SEQ ID NO:39), ACE2-1 portion (SEQ ID NO:40), linker 2 (SEQ ID NO:41), ACE2-2 portion (SEQ ID NO:42), linker 3 (SEQ ID NO:43). Fc (SEQ ID NO:28), linker 4 (SEQ ID NO:44), and heparan sulfate proteoglycan core protein (SEQ ID NO:30).
SEQ ID NO:39—Sequence of linker 1 in P61Fc-HS.
SEQ ID NO:40—Sequence of ACE2-1 portion in P61Fc-HS.
SEQ ID NO:41—Sequence of linker 2 in P61Fc-HS.
SEQ ID NO:42—Sequence of ACE2-2 portion in P61Fc-HS.
SEQ ID NO:43—Sequence of linker 3 in P61Fc-HS.
SEQ ID NO:44—Sequence of linker 4 in P61Fc-HS.
SEQ ID NO:45—Amino acid sequence of P61Fc-HS (corresponding to SEQ ID NO:38, shown in FIG. 21B).

SEQ ID NO:46—Nucleotide sequence of ACE2-Fc-SA, shown in FIG. 31A)

SEQ ID NO:47—Amino acid sequence of ACE2-Fc-SA, shown in FIG. 31B).

SEQ ID NO:48—Nucleotide sequence of ACE2-Fc-AviTag™, shown in FIG. 32A).

SEQ ID NO:49—Amino acid sequence of ACE2-Fc-AviTag™, shown in FIG. 32B).

SEQ ID NO:50—Nucleotide sequence of ACE2-Fc-Strep-Tag II®, shown in FIG. 33A).

SEQ ID NO:51—Amino acid sequence of ACE2-Fc-Strep-Tag II®, shown in FIG. 33B).

SEQ ID NO:52—Sequence of Human Immunodeficiency Virus (HIV) Envelope (Env) glycoprotein tail.

DETAILED DESCRIPTION

Enveloped viruses enter cells by receptor-mediated endocytosis using their surface proteins, such as the spike (S) protein or the envelope (E or Env) proteins, which interact with a receptor on the surface of a host cell. The interaction between the Env protein and the cell surface receptor works in a "lock-and-key" fashion. Env proteins have one or more structural receptor binding domains (RBDs) that are recognized by a binding pocket within the receptor(s). The 3D structure of a binding domain is determined by the amino acid sequence. Certain viruses use only one cellular receptor, while others use more than one. For viruses that utilize more than one receptor, co-operative ligand interaction plays a key role and the binding process is likely sequential, i.e., binding of the first ligand induces binding of the second ligand. Examples of viruses in which this process occurs include HIV, in which binding of CCR5 opens up the binding site for CD4 binding, and HCV, in which binding of HSPG and/or SRB1 allows CD81 binding.

A second mechanism of viral binding to a viral receptor on the host cell is through charge interaction. The viral Env protein is known to have a positively charged domain, which is evolutionarily conserved. The negatively charged domains of cellular receptors are involved in this process. These sites can be a sole receptor for a virus to infect a cell, or can be a second receptor. The charge of the binding pocket can be donated by acidic amino acids or by sulfation of the protein by, for example, housekeeping enzymes of the host. There are 2 known ways of sulfating protein, one of which occurs through tyrosine sulfation (as is the case for HIV), and the other which occurs by sugars such as heparan sulfate (HS), which is the case for HCV. The present disclosure utilizes the case in which a protein is sulfated by a sugar, such as HS. It is not currently known exactly how many enveloped viruses use sugar-based sulfate groups for their receptor-mediated entry process. However, regardless of the mechanism for a particular virus, the HS-sulfation site present in an Ig-Fc molecule as described herein may be a key determinant for promotion of co-operative ligand binding interaction for virus neutralization.

It is known in the art that fusion proteins of eCD4-Ig with a small CCR5-mimetic sulfopeptide binds avidly and cooperatively to the HIV-1 Env protein to prevent infection of a host cell. However, sulfation of the CCR5-mimetic peptide is required for long-term inhibiting activity of the fusion protein in a subject. Co-expression of a tyrosyl protein sulfotransferase (TPST2) and a fusion protein in a subject has been reported to help maintain the level of sulfation of the receptor, although this requires co-expression of multiple exogenous sequences in a subject or patient.

Many viruses result in chronic conditions, including liver disease, cancer, and immunodeficiencies. Hepatitis C virus (HCV) is one of the most diverse human viruses, and no universal vaccine is available to prevent or treat infection. It is estimated that around 170 million people worldwide are persistently infected with HCV, while around 8 million people in the US and Europe are chronically infected. Additionally, only around 30% of individuals infected with HCV recover fully, while the remaining 70% develop either end-stage liver disease or primary hepatocellular carcinoma, resulting in HCV being the leading cause of liver transplantation.

HCV enters the liver by attaching itself to hepatocytes using HSPG and SRB1 and internalize using multiple cell surface receptors, including CD81, claudin and occuludin. SARS-CoV-2 utilizes the ACE2 receptor, combined with heparan sulfate proteoglycans (HSPG) for entry into cells. The glycosaminoglycan component of HSPG is heparan sulfate (HS), one notable example of which is heparin. Upon heparin binding, the SARS-CoV-2 spike protein receptor-binding domain undergoes a structural change. SARS-CoV-2 infection down-regulates the ACE2 receptor in the endothelium lining in multiple organs, including lung, heart, blood vessels, liver, and kidney, causing endothelial inflammation and thrombosis, which is responsible for multiple organ failure in COVID-19 patients. Based on the above, the present inventors have identified that construction of a recombinant polypeptide that binds to both a first viral receptor and a second viral receptor that has been modified to contain a sulfated polysaccharide efficiently and effectively maintains the sulfation of the fusion protein and enhances binding between the recombinant polypeptide and the virus particle, preventing entry of the virus into the host cell. This indicates that the recombinant polypeptides of the present disclosure could provide effective, long-term, and near universal protection against viral infection. In other embodiments, a recombinant polypeptide as described herein may also be useful for treating Middle East Respiratory Syndrome (MERS), as described herein.

SARS-CoV-2 is the cause of the current COVID-19 global pandemic that has resulted in worldwide illness and death. SARS-CoV-2 is a positive-sense single-stranded RNA virus that a member of the Coronaviridae family of viruses. It infects human cells by interactions between spike (S) receptor binding domain (RBD) and specific amino acid residues in the angiotensin converting enzyme 2 (ACE2) receptor. S proteins of coronaviruses, including SARS-CoV-2, are cleaved into, and function as, two separate subunits, S1 (binds the receptor) and S2 (induces fusion between viral and cellular membranes). This cleavage occurs at the S1/S2 furin cleavage site during virion assembly and secretion. In contrast to this, the S protein of SARS-CoV is not cleaved, but rather functions as a single protein, even though the two proteins share approximately 70% homology between the two. In addition, the S protein of SARS-CoV-2 has a PRRAR pentapeptide insertion at the S1/S2 cleavage site, which is absent in the SARS-CoV S protein. The high arginine (R) content of the SARS-CoV-2 S protein leads to an expected higher charge interaction of the virus with HSPGR.

The present disclosure provides recombinant polypeptides, pharmaceutical compositions, RNA molecules, and related methods for preventing and treating viral infections. Immunoglobulins (Ig) or fragments thereof, soluble or membrane-bound receptors or fragments thereof, spacer regions, regions of antibodies specific to a particular virus, and/or sulfated polysaccharides or other compounds that can be sulfated may be combined advantageously into a recombinant polypeptide to prevent entry of a virus into a cell. Such recombinant polypeptides as described herein, as well as vectors, compositions, and methods for treating a subject or patient, may enable treatment or prevention of infection of any virus, as the present disclosure bypasses viral sequence heterogeneity. It is therefore possible to capture all viral genotypes, indicating the universality of the present disclosure to infective viruses.

In some embodiments, the present disclosure describes protein products, RNA products, and recombinant adenoviral vector products that are broadly useful for treating early to late-stage viral infection. For example, as described herein, a recombinant polypeptide of the present disclosure may be an Ace2-Fc recombinant polypeptide, or may be an Ace2-Fc-HS recombinant polypeptide. Such protein products may be expressed and purified from mammalian cell culture as described herein, and are useful for treatment by intravenous (IV) infusion of any viruses described herein, such as including, but not limited to, SARS-CoV, SARS-CoV-2, and human coronavirus NL63 (HCoV-NL63), which causes the common cold. In other embodiments, an RNA product as described herein may be an RNA molecule or composition thereof, which is useful for use in an in vitro T7 transcription system formulated with cationic liposomes for treatment of any viruses described herein by intramuscular (IM) or subcutaneous (SC) administration. In other embodiments, a recombinant adenoviral vector product as described herein may be an adenovirus, adeno-associated virus (AAV), Ad5, or Ad26 virus particle or compositions thereof, which may be expressed and purified from cell culture for treatment of any viruses described herein by nasal or IM administration. These and other embodiments are described in detail herein.

In some embodiments, protein products, RNA products, or recombinant adenoviral vector products described herein are effective for use in treatment of a virus involved in an epidemic or pandemic, such as the COVID-19 global pandemic, or for any future viruses that utilize the same cellular receptors. In other embodiments, protein products, RNA products, or recombinant adenoviral vector products described herein are effective for viruses that escape or evade vaccines and/or monoclonal antibodies (Mabs). These viruses are captured by receptor, as their escape mutation is suicidal. The protein products, RNA products, or recombinant adenoviral vector products described herein provide ACE2, a critical enzyme to maintain endothelial integrity for many organs. SARS-CoV-2 infection decreases ACE2, which is the main cause of endothelial thrombosis in patients infected with SARS-CoV-2. The protein products, RNA products, or recombinant adenoviral vector products described herein also provide an effector function, e.g., complementation fixing or T-cell response (antibody-dependent cell cytotoxicity (ADCC)).

For many viruses, no surface antigen tests are available, due to the variability in the viral envelope. Thus, in some embodiments, the present disclosure provides a rapid point-of-care test for viral infection to measure current infection. The present disclosure thus intends to encompass diagnosis of, treatment for, and prophylaxis against any virus capable of infecting a cell using cell surface receptors. Included among such viruses are both enveloped and non-enveloped viruses. Enveloped viruses may include any viruses with a viral envelope surrounding the capsid, such as including, but not limited to, HCV, MERS, and the like. In other embodiments, viruses may lack a viral envelope around the viral capsid and be capable of infecting a cell using cell surface receptors. One non-limiting example of non-enveloped viruses is Picornavirus, which encompasses a large family of small, cytoplasmic viruses, including, but not limited to, Rhinovirus, Enterovirus, Hepadnavirus and the like.

Unless otherwise specified herein, the recombinant polypeptides, pharmaceutical compositions, RNA molecules or compositions, and related methods, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., (3rd ed., 2000); Brent et al., Current Protocols in Molecular Biology, John Wiley & Sons, Inc. (2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present disclosure.

Embodiments of the present disclosure provide a recombinant polypeptide comprising: a) an Ig Fc fragment and a sulfated polysaccharide; and b) at least one viral receptor fragment. In another embodiment, the disclosure provides a pharmaceutical composition comprising a recombinant polypeptide comprising: a) an Ig Fc fragment and a sulfated polysaccharide; and b) at least one viral receptor fragment. Other embodiments provide a method of preventing or treating a viral infection in a subject in need thereof, comprising administering to the subject a therapeutically or prophylactically effective amount of a pharmaceutical composition comprising a recombinant polypeptide comprising: a) an Ig Fc fragment and a sulfated polysaccharide; and b) at least one viral receptor fragment. Other embodiments provide a RNA molecule comprising: a) a first ribonucleotide sequence having a 5'-Cap or expressing an Internal Ribosome Entry Site (IRES); and b) a second ribonucleotide sequence expressing a recombinant polypeptide comprising: a) an Ig Fc fragment and a sulfated polysaccharide; and b) at least one viral receptor fragment. Other embodiments provide a therapeutic composition comprising: a) a live viral expression vector; and b) a polynucleotide sequence expressing a recombinant polypeptide comprising: a) an Ig Fc fragment and a sulfated polysaccharide; and b) at least one viral receptor fragment. Other embodiments provide an expression system comprising a polynucleotide sequence encoding a recombinant polypeptide comprising: a) an Ig Fc fragment and a sulfated polysaccharide; and b) at least one viral receptor fragment.

Recombinant Polypeptides for Prevention of Viral Infection

In some embodiments, the present disclosure provides a recombinant polypeptide comprising: a) an Ig Fc fragment and a sulfated polysaccharide; and b) at least one viral receptor fragment. Such a recombinant polypeptide binds to proteins present on virus particles via the viral receptor fragment(s), mimicking binding of a virus to a cell surface receptor on a host cell. In some embodiments, a recombinant polypeptide may have more than one viral receptor fragment, allowing the recombinant protein to co-operatively bind to more than one viral protein. The virus particles captured by this recombinant polypeptide are cleared from circulation by the effector function of the Ig Fc fragment, provided these mechanisms of action occupy the viral proteins and prevent or block binding of the virus to the cell surface receptors on a host cell, effectively preventing entry of a virus into a cell and reducing the infectivity of the virus.

In some embodiments, an antibody fusion molecule as described herein may comprise one or more of an Fc region, one or more $C_H$ regions, one or more $C_H$ regions, a Fab, Fab', F(ab')2, a single chain Fv (ScFv) and/or Fv fragments, hinge regions, as well as fragments or portions thereof, and any portion of an antibody having specificity toward a desired target epitope or epitopes. As described herein, an Ig Fc or fragments thereof may be an antibody or antibody fragment, or may be a single chain, two-chain, and/or multi-chain protein, and/or a glycoprotein belonging to the classes of polyclonal, monoclonal, chimeric, bispecific, and/or hetero immunoglobulins. In some embodiments, an Ig Fc fragment as described herein may refer to a monoclonal antibody. In some embodiments, synthetic and/or genetically engineered variants of these immunoglobulins are encompassed within the scope of the present disclosure.

To increase the activity or half-life of any recombinant polypeptide or compositions comprising these, a viral receptor fragment(s) as described herein may be fused or bound to a larger molecule or carrier. For example, a viral receptor as described herein may be fused to all or part of an immunoglobulin (Ig) Fc-domain. Such a fusion confers on the viral receptor fragment(s) fusion antibody effector functions, including the ability to mediate antibody-dependent cell-mediated cytotoxicity, to access mucosal compartments, and to transport across the placenta.

Thus, in some embodiments, a recombinant polypeptide as described herein may contain an Fc binding region of an immunoglobulin, in addition to the viral receptor fragment(s). In some embodiments, a recombinant polypeptide of the present disclosure may also contain portions of immunoglobulin molecules or antibodies, such as including, but not limited to, all or portions of a constant heavy chain, a variable heavy chain, a constant light chain, a variable light chain, a hinge region, and/or an Fc domain of a Ig, as well as variants thereof. For example, a recombinant polypeptide as described herein may be combined with portions of a human IgG. Any type of immunoglobulin may be used as appropriate, such as including IgG, IgA, IgM, IgD, IgE, and variants thereof.

For example, a recombinant polypeptide as described herein may be constructed by joining a viral receptor fragment at either or both the N-terminus or the C-terminus of an Ig-Fc fragment. The one or more viral receptor fragment(s) may be joined directly together in any configuration, or they may be separated by a spacer region. Such a spacer region may be beneficial in some embodiments for proper placement of the viral receptor fragments such that they are able to bind sequentially or co-operatively to the viral envelope proteins, and/or to ensure proper function of each of the components. Elements of a recombinant polypeptide as described herein may be joined in any order. In some embodiments, an SRB1 receptor fragment may be joined to a CD81 receptor fragment and separated by a spacer as shown in FIGS. 1-3 for treatment of HCV. In other embodiments, a CD26 or its fragment CD26-B4C may be combined into a recombinant polypeptide as shown in FIG. 4 for treatment of Middle East Respiratory Syndrome (MERS). These constructs, or others encompassed within the scope of the disclosure, may then be conjugated to an Ig-Fc region. In some embodiments, a sulfated polysaccharide, such as low molecular weight heparan sulfate, may be conjugated to an Fc to provide a negative charge to the recombinant polypeptide as described herein. As would be understood by one of skill in the art, components herein that have been identified as useful in accordance with the disclosure for inclusion in a recombinant polypeptide or fusion protein may be altered in a number of ways to include variants having any cell surface receptor(s) for any virus as disclosed herein, and any useful regions of an immunoglobulin (Ig) or Fc region. Such recombinant polypeptides and variants thereof are also encompassed within the scope of the disclosure.

In some embodiments, a recombinant polypeptide as described herein may be in a monomeric form, or may be in a multimeric form, for example a dimer, a trimer, a tetramer, a hexamer, an octamer, a decamer, or the like. FIGS. 24-29 demonstrate possible arrangements for such multimeric forms of a recombinant polypeptide of the present disclosure. In some embodiments, described in detail below, a monomer may be joined to another monomer to form a dimer, which is then further multimerized into a tetramer or octamer as described herein. A monomer of the present disclosure dimerizes co-translationally by virtue of Fc-Fc integration, and then further into a tetramer by streptavidin (SA), and then into an octamer by biotin-SA interaction. These and other embodiments are described in detail herein.

In some embodiments, a recombinant polypeptide disclosed herein may have a) an Ig Fc fragment and a sulfated polysaccharide; and b) at least one viral receptor fragment, and may further include hinge domains, linkers, or spacers as disclosed herein. The at least one viral receptor fragment may be any viral receptor or fragment thereof disclosed herein, or combinations of viral receptors or fragments thereof, for example including, but not limited to, viral receptors listed in Table 1 below, such as CD81, SRB1, HSPG, CD26, CD26-Blade4, CD26-B4C, ACE2, CD147, sialic acid, DC-SIGN (CD209), AXL, Tyro3, TIM-1, PtdSer R (CD300a), NPC1, NTCP, among others. One of skill in the art would recognize that other viral receptors may be used for treatment of viruses, and these are intended to be encompassed within the scope of the present disclosure. In some embodiments, more than one viral receptor may be included in a recombinant polypeptide described herein. In some embodiments, the viral receptor is an ACE2 receptor for treatment or prevention of SARS-CoV-2 infection. In some embodiments, a recombinant polypeptide described herein is a dimer having two identical polypeptide chains. In some embodiments, each viral receptor on the polypeptide dimer is identical. In some embodiments, the viral receptor is ACE2 receptor.

In some embodiments, tetramerization of an ACE2-Fc recombinant polypeptide may be accomplished in cell culture using streptavidin (SA) with biotin binding sites, depicted in FIG. 24. The addition of SA to a recombinant polypeptide will result in the spontaneous formation of a tetramer (referred to herein as ACE2-Fc-SA) as a result of the binding of the SA groups of two individual ACE2-Fc recombinant proteins, each in dimeric form, to form an ACE2-Fc tetramer-SA (FIG. 24). The resulting tetrameric recombinant protein is expressed and secreted in cell culture.

In some embodiments, octamerization of an ACE2-Fc recombinant polypeptide may be accomplished in vitro using SA and Strep-tag II®. As described above for the ACE2-Fc-SA tetramer, the binding of the SA groups of two individual ACE2-Fc recombinant proteins, each in a dimeric form, results in the spontaneous formation of an ACE2-Fc-SA tetramer, which is then further multimerized using, for example, a Strep-tag II peptide, which will bind to the biotin binding sites on the SA to form an Fc octamer as shown in FIG. 25.

In other embodiments, tetramerization of an ACE2-Fc recombinant polypeptide may be accomplished in vitro using a biotinylated AviTag™ and SA with biotin binding sites. SA is added to an ACE2-Fc dimer with terminal AviTag™ groups (i.e., ACE2-Fc-AviTag™) resulting in the spontaneous formation of a tetramer as a result of the binding of the biotinylated AviTag™ of each ACE2-Fc-AviTag™ dimer to the biotin binding sites. (FIG. 26).

In some embodiments, octamerization of an ACE2-Fc recombinant polypeptide may be accomplished in vitro using an ACE2-Fc-AviTag™ dimer as described in the previous paragraph. The ACE2-Fc-AviTag™ dimer is combined with tetrameric ACE2-Fc-SA to form an octameric recombinant polypeptide as shown in FIG. 27 as a result of the terminal biotinylated AviTag™ of the ACE2-Fc-AviTag™ binding to the ACE2-Fc-SA tetramer at the biotin binding sites.

In other embodiments, tetramerization of an ACE2-Fc recombinant polypeptide may be accomplished in vitro using dimeric ACE2-Fc-AviTag™ biotinylated with heparin and combining it with SA with biotin binding sites. The AviTag™ groups biotinylated with heparin bind to the biotin binding sites on the SA to form a tetrameric recombinant polypeptide as shown in FIG. 28.

In some embodiments, octamerization of an ACE2-Fc recombinant polypeptide may be accomplished in vitro using an ACE2-Fc-AviTag™ dimer biotinylated with heparin as described in the previous paragraph. The ACE2-Fc-AviTag™ dimer biotinylated with heparin is combined with tetrameric ACE2-Fc-SA to form an octameric recombinant polypeptide as shown in FIG. 29 as a result of the terminal biotinylated AviTag™ of the ACE2-Fc-AviTag™ binding to the ACE2-Fc-SA tetramer at the biotin binding sites.

Thus, in some embodiments, a recombinant polypeptide described herein may comprise one or more dimers, each of which may comprise at least two viral receptors or fragments thereof. As described herein and presented at least in FIGS. 24-30, a recombinant polypeptide useful according to the present disclosure may comprise one or more identical dimers to make up a tetramer or an octamer. The dimers can be identical as described herein, or they may be different from each other. In some embodiments, both viral receptors or fragments thereof on a dimer described herein are ACE2. In some embodiments, a recombinant polypeptide described herein is a tetramer or an octamer. Such a tetramer or octamer may be produced as described herein using, for example, to comprise one or more streptavidin, one or more AviTag™, and/or one or more Strep-Tag II®. As described herein, a streptavidin may comprise one or more biotin binding site, which is used for production of a multimer as described herein. An AviTag™ as described herein may be biotinylated, such as with heparin. The structure of such a multimeric recombinant polypeptide is described herein, at least in FIGS. 24-29 and set forth as SEQ ID NOs: 46-51. For such a multimeric recombinant polypeptide, each polypeptide of the multimer, e.g., a dimer, a tetramer, or an octamer, comprises a sequence set forth as SEQ ID NOs:47, 49, or 51.

The above tetramerization and octamerization methods may be useful with any viral receptor—and thus any virus—disclosed herein or known in the art. Useful embodiments may include any viruses that use ACE2 receptor as a cellular receptor for infection, such as SARS-CoV, SARS-CoV-2, and/or CoV-NL63. The present disclosure thus encompasses methods of making multimers of a recombinant polypeptide as described herein, comprising the use of an ACE2-Fc recombinant polypeptide and combinations of streptavidin (SA), AviTag™, and/or Strep-tag II® as described herein and in the Examples.

Viral Receptors

As described herein, viruses enter a host cell by binding to cell surface receptors with proteins present on the virus. Some viruses may bind to a single host cell surface receptor, and some viruses may bind to more than one host cell surface receptor. In such cases, binding of a virus to its receptors may be sequential or may be co-operative. In some embodiments, binding of a virus to a cell surface receptor may cause, enable, or initiate binding of a second viral protein to a second host cell surface receptor. A viral receptor fragment as described herein is intended to be inclusive of any molecules or peptide sequences that are able to compete with the natural receptor for binding to the viral protein. Examples of such peptides or mimetics are well known in the art.

Viral entry into a host cell is known in some cases to depend on the proximity or spatial arrangement of host cell surface receptors. Viral host cell receptors are known in the art and may vary with each viral family, or with individual virus strains. Table 1 provides receptors for a number of viruses.

TABLE 1

| Viral Receptors | |
|---|---|
| Virus | Receptor |
| HCV | HSPG, CD81, SRB1 |
| MERS CoV | HSPG, CD26, |
| SARS CoV & CoV-NL63 | HSPG, ACE2 |
| SARS CoV-2 | HSPG, ACE2, CD147, Sialic Acid, SRB1 |
| Zika | DC-SIGN (CD209), AXL, Tyro3, TIM-1, PtdSer R (CD300a) |
| Ebola | TIM-1, NPC1 |
| HBV | HSPG, NTCP |

SRB1, Scavenger Receptor B-1;
HSPG, heparan sulfate proteoglycan

In some embodiments, a viral receptor or fragment thereof may be any fragment of a host cell surface receptor that is recognized by a virus and to which a virus would bind. For example, as shown in the table and described herein, a viral receptor fragment in accordance with the disclosure may include, but is not limited to, CD81, SRB1, HSPG, CD26, CD26-Blade4, CD26-B4C, ACE2, DC-SIGN (CD209), AXL, Tyro3, TIM-1, PtdSer R (CD300a), NPC1, NTCP, or the like. In some embodiments, a viral receptor or fragment thereof that is recognized by HCV includes, but is not limited to, CD81 and/or SRB1. In some embodiments, a viral receptor or fragment thereof that is recognized by West Nile or Dengue virus includes, but is not limited to, AXL and/or TIM-1, and/or TIM-4. In some embodiments, a viral receptor or fragment thereof that is recognized by Zika virus includes, but is not limited to, AXL and/or Tyro3.

In some embodiments, a viral receptor or fragment thereof that is recognized by MERS includes, but is not limited to, CD26 and/or CD26-Blade4 and/or CD26-B4C. In some embodiments, a viral receptor or fragment thereof that is recognized by SARS includes, but is not limited to, ACE2 and/or HSPG.

In some embodiments, a viral receptor or fragment thereof that is recognized by Ebola includes, but is not limited to, NPC1 and/or TIM-1.

In some embodiments, a viral receptor or fragment thereof that is recognized by HBV includes, but is not limited to, NTCP. A fragment useful for the present disclosure would be a fragment of a receptor found on a host cell that would bind to a virus and prevent its entry into the host cell. As would be understood by one of skill in the art, a recombinant polypeptide as described herein may be modified as deemed appropriate with any viral receptor or fragment thereof that would bind to and maintain binding to a virus.

Many viruses and/or viral families use different combinations of host cell receptors as a first or a second viral receptor. For example, as shown in the table above, a number of viruses, including, but not limited to, HCV, Mers-CoV, Sars-CoV, and HBV, all use HSPG as a second viral receptor.

In some embodiments, HSPG-dependent viruses may be grouped into a number of categories, described by Cagno et al. (*Viruses* 11(7):596, 2019), incorporated herein by reference. For example, dependence on HSPG has been proven on natural isolates of viruses including, but not limited to, Herpes simplex virus, Dengue virus, Echovirus 5, Echovirus 6, and North American eastern equine encephalitis virus. Dependence on HSPG has been proven on laboratory strains of viruses including, but not limited to, Cytomegalovirus, Pseudorabies virus, Merkel cell polyomavirus, Hepatitis B virus/Hepatitis Delta virus, Vaccinia virus, Adenovirus 2 (including type D), Norovirus genogroup II, Schmallenburg virus, Rabies virus, Swine vesicular disease virus, Theiler murine, encephalomyelitis virus, Human parechovirus 1, Porcine reproductive and respiratory syndrome virus, Porcine circovirus 2, Human herpes virus-8 (Kaposi sarcoma herpes virus), Human papillomavirus, Hepatitis C virus, Adeno-associated virus 2, Human immunodeficiency virus, Filoviruses, Akabane virus, Rift valley fever virus, Rhinovirus 54, Enterovirus 71, Coxsackie virus A9, Hendra and Nipah viruses, Human T cell leukemia virus type 1, and Hepatitis E virus. Dependence on HSPG has been proven from cell culture adaptation of viruses including, but not limited to, Foot and mouth disease virus, Venezuelan equine encephalitis virus, Sindbis virus, Semliki forest virus, Rhinovirus C15, Rhinovirus 8, Rhinovirus 89, Coxsackie virus B3, Coxsackie virus A24, Yellow fever virus, Japanese encephalitis virus, West Nile virus, Tick-borne encephalitis virus, Coronavirus group 1, Coronavirus OC43, Chikungunya virus, and Murray Valley encephalitis virus. Dependence on HSPG has been proven from human intra-host adaptation of viruses including, but not limited to, John Cunningham polyomavirus, Enterovirus 70, Enterovirus 71, and Reovirus. In addition, viruses including, but not limited to, Respiratory syncytial virus, Parainfluenza virus 3, Parainfluenza virus A11, Human metapneumovirus, Zika virus, Adenovirus 5 (including type D), and Coronavirus NL63 may also depend upon HSPG as a receptor.

In some embodiments, other viruses, such as Zika and Ebola, while not using exactly the same HSPG, still use a charged receptor pocket. In some embodiments, HSPG may merely provide a charge to the receptor pocket, without itself acting as a receptor. In some embodiments, the present disclosure provides recombinant polypeptides that recognize and bind to viruses that use HSPG as a receptor. In other embodiments, a recombinant polypeptide as described herein recognizes and binds to viruses that use HSPG as a charge provider and a separate, distinct receptor. In some embodiments, HBV uses HSPG as the low-affinity HBV receptor and NTCP as a receptor (Hu J. and Liu K., *Viruses* 2017, 9.56: doi:10.3390/v90300056).

In some embodiments, binding of a viral receptor or fragment thereof of a recombinant polypeptide of the present disclosure to a specific virus may depend not only the specific proteins present in or on the viral envelope, but may also depend on the charge of the binding pocket formed by the specific amino acid sequence of the viral receptor or fragment thereof. In some embodiments, the net charge of a viral protein or cell surface receptor to which it binds may promote or inhibit binding between a virus and a host cell surface receptor. It is known in the art that certain viruses bind to negatively charged binding pockets formed by a particular domain of a host cell surface protein. In this regard, as described herein, a negative charge may be provided to a recombinant polypeptide of the disclosure by the addition of a sulfated sugar or polysaccharide. Such modification may be provided to enhance binding of a virus to its host cell receptor(s). Thus, in some embodiments, a recombinant polypeptide as described herein may be modified to contain a sulfated sugar on one or more viral receptors or fragments thereof as described herein.

In some embodiments, a sulfated polysaccharide of the disclosure may be any sulfated sugar or polysaccharide. Sulfated polysaccharides may include glycosaminoglycans, glyconectins, proteoglycans, fucoidan, such as including, but not limited to, heparan sulfate (HS) and chondroitin sulfate (CS). A polysaccharide useful in accordance with the disclosure may be linear or branched, and may be naturally occurring or artificially synthesized or modified. In some specific embodiments, a sulfated sugar as described herein may be present on or part of a proteoglycan. A proteoglycan may be glycosylated with any number of polysaccharide molecules, such as including 1, 2, 3, 4, 5, 6, 7, 8, 9, 10, or more polysaccharide molecules. For example, in some embodiments, a proteoglycan useful for the present disclosure may be heparan sulfate proteoglycan (HSPG).

There are three major classes of HSPG (i.e., syndecan, glypican, and perlecan). Most HSPG, such as including, but not limited to syndecans and glypicans, are anchored in the plasma membrane of eukaryotic cells, while others, including, but not limited to, perlecan, agrin, and collagen XVII, are found in the extracellular matrix (ECM). In accordance with the present disclosure, any HSPG may be used in a recombinant polypeptide as described herein, such as including, but not limited to, syndecan, glypican, and perlecan.

As used herein, "sulfation" refers to the addition of a sulfo group to a sugar or polysaccharide. Sulfation is involved in a variety of biological processes, including viral entry into cells, detoxification, hormone regulation, molecular regulation, molecular recognition, and cell signaling, among others, in which it plays a role in strengthening protein-protein interactions. Some viral strains require sulfation for binding of the viral receptor to its host cell surface receptor. In some embodiments, cellular receptors may use a variety of mechanisms for sulfation of a polysaccharide, in order to create a negatively charged binding pocket. For example, as described herein, heparan sulfate proteoglycan receptor (HSPGR) employs a terminal hexose sugar chain as a site of sulfation. In this way, many viruses use this charged domain as a receptor for entry into a cell.

In addition to a cell surface receptor, some viruses additionally use a second viral receptor for recognition and/or entry into a cell. For example, as described herein, HSPG is used by some viruses as a co-factor for binding to and infecting a host cell. In some embodiments, HS or HSPG is ubiquitous in a cell and may be used as a co-factor by many viruses. These compounds may in some embodiments facilitate binding to a receptor. Many different viruses are known to use such receptors, including, but not limited to flaviviruses, coronaviruses, and/or filoviruses. Thus, in some embodiments, the present disclosure provides a recombinant polypeptide that provides methods and compositions for preventing infection of these viruses.

A polysaccharide or proteoglycan as described herein may contain one or more sulfation sites, such as 1, 2, 3, 4, 5, 6, 7, 8, 9, or 10 sulfation sites, or the like. Likewise, any particular proteoglycan, such as HSPG, may contain one or more sulfation sites as described herein. In accordance with the present disclosure, sulfation of a sugar or polysaccharide may occur at any location within the sugar or polysaccharide. For example, as described herein, a recombinant polypeptide of the present disclosure may have a specific amino acid motif that serves as a site of sulfation, or as a means for directing sulfation to a specific location in the polysaccharide. One such exemplary motif that serves as a sulfation site for a recombinant polypeptide as described herein is a serine-glycine-aspartic acid (SGD) motif. However, other amino acid motifs or sequences may alternatively serve as a site for sulfation and virus recognition are encompassed within the present disclosure. In accordance with the disclosure, any amino acid sequence of a protein or polypeptide, or any domain present in a protein or polypeptide that is formed by virtue of an appropriate secondary, tertiary, or quaternary protein structure may serve as a site of sulfation and virus binding is encompassed within the present disclosure.

In some embodiments, an amino acid motif serving as a site of sulfation and virus binding in accordance with the disclosure may be present at any location on a protein or polypeptide. For example, as described herein, an SGD motif may be located within a certain distance of a particular amino acid residue in a protein or polypeptide. Certain amino acids, such as aspartic acid and glutamic acid are acidic amino acids and exhibit a negative charge, while other amino acids, such as arginine, histidine, and lysine are basic amino acids and exhibit a positive charge. In accordance with the disclosure, an SGD motif may be located within a certain number of amino acid residues of at least one acidic amino acid. For example, an SGD motif may be located within 1, 2, 3, 4, 5, 6, 7, 8, 9, 10, 11, 12, 13, 14, 15, 16, 17, 18, 19, 20, or more amino acids of at least one acidic amino acid residue. In specific embodiments, an SGD motif as described herein may be located within 7, 8, 9, and/or 10 amino acid residues of at least one acidic amino acid residue. In some embodiments, an SGD motif as described herein may serve as the recognition site for sulfation, and also may serve as the location for sulfation and virus binding. In some specific embodiments, an SGD motif may be recognized by a cellular housekeeping enzyme, which may add a sulfo group to the serine residue of the SGD motif.

In some embodiments, a recombinant polypeptide as described herein has at least one viral receptor or fragment thereof. As described herein, such a viral receptor or fragment(s) thereof enables binding of the recombinant polypeptide to the virus, thereby mimicking a cell surface receptor on a host cell. In some embodiments, a recombinant polypeptide of the disclosure may have more than one viral receptor or fragment thereof, allowing the recombinant protein to co-operatively bind to more than one viral protein. This mechanism of action occupies the viral proteins and prevents or blocks binding of the virus to the cell surface receptors on a host cell, effectively preventing entry of a virus into a cell and reducing the infectivity of the virus.

In some embodiments, a recombinant polypeptide as described herein may prevent infection of any viral family or strain that utilizes one or more specific cell surface receptors for entry into a cell. In other embodiments, a recombinant polypeptide as described herein may prevent infection of any viral family or strain that utilizes HSPG as a receptor for entry into a cell. For example, a recombinant polypeptide of the disclosure may contain viral receptors that will bind to a virus from the Flaviviridae, Coronaviridae, Hepadnaviridae and/or Filoviridae families. One of skill in the art will recognize that a recombinant polypeptide of the present disclosure may bind to any specific viral family, strain, or isolate that binds to a specific cell surface receptor. Recombinant polypeptides of the present disclosure may be customized to inhibit infection of a specific virus as described herein.

In some embodiments, viruses that may be especially suited for a recombinant polypeptide of the present disclosure include, but are not limited to, Flaviviridae viruses, including Yellow Fever virus, West Nile virus, Dengue virus, Japanese encephalitis virus, Zika virus, Hepatitis C virus (HCV), Pegiviruses, and the like. In some embodiments, viruses that may be especially suited for a recombinant polypeptide of the present disclosure include, but are not limited to, Coronaviridae viruses, including coronavirus, severe acute respiratory syndrome-related coronavirus (SARS CoV), Middle East respiratory syndrome-related coronavirus (MERS), and the like. In some embodiments, viruses that may be especially suited for a recombinant polypeptide of the present disclosure include, but are not limited to, Filoviridae viruses, including Ebolavirus, and the like.

In some embodiments, a recombinant polypeptide as described herein may be administered to a subject or patient as a fusion protein having a structure as shown in FIGS. 1-3. In other embodiments, a recombinant polypeptide as described herein may be administered to a subject or patient as a fusion protein having a structure as shown in FIG. 4. Alternatively, in some embodiments a recombinant polypeptide as described herein may comprise two or more polypeptides, peptides, components, or subunits that separately bind to the viral proteins to prevent entry into a cell. In some embodiments, the different components, e.g., peptides or polynucleotide chains, may be conjugated covalently or noncovalently prior to administration to a subject or patient. For embodiments of the disclosure wherein a live viral vector is provided, such a vector may encode a recombinant fusion protein as a single entity, or may encode separate, distinct components or subunits that are able to assemble in vivo into a recombinant fusion protein as described herein.

Heparin is a 17-19 kDa polysaccharide that is isolated from pig intestine, enzyme digested, and size fractionated by HPLC. As described herein and in the Examples, heparin was found to inhibit entry of SARS-CoV-2 into target cells as an attachment inhibitor. Heparin is a member of a group of polysaccharides called heparan sulfates, which contributes to a negative charge in the viral binding pocket. As described herein, the positively charged viral envelope protein binds to a negatively charged binding pocket on a target host cell. Attachment of the virus to the host cell through heparan sulfate proteoglycans (HSPG) is necessary for the entry of the virus through the ACE2 receptor.

As described herein, the Inventors synthesized retrovirus (murine leukemia virus, MLV)-based SARS-CoV, SARS-CoV-2, and MERS-CoV pseudovirus particles (pp), referred to herein as MLV-Spp. From these experiments, it was determined that heparin is an efficient inhibitor for SARS-CoV-2 infection in target cells (VeroE6 or VeroE6/Tmprss2), and inhibition is stronger for SARS-CoV-2 than for SARS-CoV or MERS-CoV.

Expression Systems and Vectors Encoding a Recombinant Polypeptide

As detailed herein, the disclosure provides pharmaceutical and therapeutic compositions that can be administered to a mammalian subject in need of long-term in vivo protection against or treatment for viral infection. Such compositions typically contain expression systems, e.g., polynucleotide sequences, expression vectors, or viral vectors that encode or express a recombinant polynucleotide as described herein. Compositions of the present disclosure allow optimal in vivo activity or co-expression in a subject or patient (e.g., human or non-human primate) of a recombinant polypeptide as described herein, which provides potent and long-term protection against infection of a virus as described herein.

Optimal expression of a recombinant polypeptide as described herein can be accomplished via various mechanisms. Such optimal expression may be accomplished using a desired structural design of an expression vector encoding a recombinant polypeptide, or by the use of appropriate regulatory elements in an expression vector. In addition, optimal expression of a recombinant polypeptide of the disclosure in vivo may further be optimized by measurement of cellular levels of the recombinant polypeptide as described herein. Any assays for determination of appropriate levels of the polypeptide may be used as appropriate. Such tests can all be readily carried out via standard assays or protocols well known in the art.

In some embodiments, sulfation of a recombinant polypeptide as described herein may be evaluated by routinely practiced methods, e.g., $^{35}SO_4$-incorporation, and gel assay combined with GAG-specific alcian blue/silver staining. In other embodiments, viral neutralizing activities may be assessed using any assays known in the art, such as a neutralization assay.

In some preferred embodiments, polynucleotide sequences encoding a recombinant polypeptide as described herein are operably-linked to expression control sequences (e.g., promoter sequences) in a virus-based expression vector or expression system described herein. Some examples of viral vectors suitable for the disclosure include retrovirus-based vectors, e.g. lentiviruses, adenoviruses, adeno-associated viruses (AAV), and vaccinia vectors. In some embodiments, an adenoviral vector that may be useful for the present disclosure may be Ad5, Ad26. In some embodiments, a composition of the disclosure can contain a recombinant AAV vector (rAAV) or viral particle harboring a vector expressing a recombinant polypeptide as described herein. In some embodiments, a vaccinia vector useful for the present disclosure may be a Canary Pox vector. In some embodiments, the structure of the vector may be modified as necessary for optimization of expression or to achieve a desired cellular level, of the recombinant polypeptide, such as including expression controlling elements (e.g., promoter or enhancer sequences).

Various promoter sequences well known in the art may be used in accordance with the disclosure. These include, but are not limited to, e.g., CMV promoter, elongation factor-I short (EFS) promoter, chicken-actin (CBA) promoter, EF-1a promoter, human desmin (DES) promoter, Mini TK promoter, and human thyroxine binding globulin (TBG) promoter. Additionally, an expression vector of the disclosure may include a number of regulatory elements to achieve optimal expression of the recombinant polypeptide. For example, a 5'-enhancer element and/or a 5'-WPRE element may be included to elevate expression of the recombinant polypeptide. WPRE is a post-transcriptional response element that has 100% homology with base pairs 1093 to 1684 of the Woodchuck hepatitis B virus (WHYS) genome. When used in the 3' UTR of a mammalian expression cassette, it can significantly increase mRNA stability and protein yield. As used herein, an "expression cassette" refers to a polynucleotide sequence comprising at least a first polynucleotide sequence capable of initiating transcription of an operably linked second polynucleotide sequence and optionally a transcription termination sequence operably linked to the second polynucleotide sequence. As used herein, an expression cassette may comprise an exogenous nucleic acid encoding a recombinant polypeptide as described herein operably linked to a promoter as described herein.

By expressing a recombinant polypeptide as described herein in a subject or patient, effective and long-term in vivo protection against and/or treatment of viral infection in subjects such as humans. For such a method, a subject may be administered a pharmaceutical composition that contains a therapeutically or pharmaceutically effective amount of a recombinant polypeptide or therapeutic composition or expression system of the disclosure. In some related embodiments, the disclosure provides therapeutic compositions that contain expression systems for optimally expressing a recombinant polypeptide as described herein in the subject. The expression systems may be polynucleotide sequences or expression vectors, as well as liposomes or other lipid-containing complexes, and other macromolecular complexes capable of mediating delivery of a polynucleotide sequence to a host cell or subject. Various expression vectors or systems can be employed for expressing a recombinant polypeptide of the disclosure upon administration to a subject. In some embodiments, the expression vectors or expression systems may be based on viral vectors. In some other embodiments, the expression systems are comprised of polynucleotide sequences harboring coding sequences for a recombinant polypeptide as described herein, including deoxyribonucleic acid and ribonucleic acid sequences. In some embodiments, the expression vectors or systems are administered to subjects in the form of a recombinant virus. For example, the recombinant virus can be a recombinant adeno-associated virus (AAV), e.g., a self-complementary adeno-associated virus (scAAV) vector. Such viral delivery methods allow safe, unobtrusive, and sustained expression of high levels of protein therapeutics.

As described above, when using the therapeutic compositions of the disclosure for preventing or treating viral infections in a subject, expression levels of the recombinant polypeptide may be examined during the treatment process. In some embodiments, the administered recombinant polypeptides or compositions result in expression of the recombinant polypeptide in the subject in an amount that is sufficient to reduce the number of copies of viral RNA detectable in the plasma of the subject by at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, 100-, 150-, 200-, 250-, 300-, 350-, 400-, 450-, 500-fold, 750-fold, 1000-fold, or more. In some preferred embodiments, treatment of a subject or patient with a recombinant polypeptide or a therapeutic or pharmaceutical composition of the disclosure results in a reduction of viral RNA to undetectable levels in the blood or plasma of the treated subject. Such undetectable levels may be defined as fewer than 50 copies of viral RNA per mL of plasma in a real-time reverse transcriptase polymerase chain reaction (real-time RT PCR) assay.

An expression vector as described herein may contain the coding sequences and other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors may be modified to provide such functionalities. Selectable markers can be positive, negative, or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Expression vectors or systems suitable for the disclosure include, but are not limited to, isolated polynucleotide sequences, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors and RNA, which are present in liposomes, e.g., neutral or cationic liposomes, such as DOSPA/DOPE, DOGS/DOPE or DMRIE/DOPE liposomes, and/or associated with other molecules such as cationic lipid (DOTMA/DOPE) complexes. Exemplary gene viral vectors are known in the art and described below. Vectors may be administered via any route including, but not limited to, intramuscular, buccal, rectal, intravenous or intracoronary administration, and transfer to cells may be enhanced using electroporation and/or iontophoresis.

Some embodiments can employ adeno-associated virus vectors or adenoviral vectors for optimally expressing a recombinant polypeptide as described herein in a subject or patient. Adenoviral vectors may be made replication-incompetent by deleting the early (El A and El B) genes responsible for viral gene expression from the genome. They may be stably maintained into the host cells in an extrachromosomal form. These vectors have the ability to transfect both replicating and nonreplicating cells. Adeno-associated virus vectors refer to recombinant adeno-associated viruses (rAAV) that are derived from nonpathogenic parvoviruses. They evoke essentially no cellular immune response and produce transgene expression lasting months in most systems. Like adenovirus, adeno-associated virus vectors also have the capability to infect replicating and nonreplicating cells and are believed to be nonpathogenic to humans.

Pharmaceutical or Therapeutic Compositions for Preventing Viral Infection

In some embodiments, the disclosure provides a therapeutic or pharmaceutical composition comprising a live viral expression vector and a polynucleotide sequence (DNA, RNA) expressing a recombinant polypeptide as described herein. Viral vectors are described in detail above and would be known to one of skill in the art. In some embodiments, an expression vector as described herein may be an adenoviral vector or a vaccinia vector.

In some embodiments, a recombinant polypeptide as described herein may be provided as a pharmaceutical or therapeutic composition to be administered to a subject or patient. A composition of the present disclosure may comprise a recombinant polypeptide as described herein in a single unit, or alternatively, in some embodiments a recombinant polypeptide as described herein may comprise two or more components or subunits that separately bind to the viral proteins to prevent entry into a cell. In some embodiments, the different components, e.g., peptides or polynucleotide chains, may be conjugated covalently or noncovalently prior to administration to a subject or patient.

A recombinant polypeptide as described herein may contain multiple distinct polypeptide chains (e.g., immunoglobulin heavy chains and a light chains), of which one chain contains one or more sulfation sites but requires one or more of the other polypeptide chains in order to bind to a host cell surface receptor.

In some embodiments, a recombinant polypeptide as described herein may be provided or administered to a subject or patient as a fully assembled fusion protein. Alternatively, in some embodiments a recombinant polypeptide as described herein may comprise two or more components or subunits that separately bind to the viral proteins to prevent entry into a cell. In some embodiments, the different components, e.g., peptides or polynucleotide chains, may be conjugated covalently or noncovalently prior to administration to a subject or patient. For embodiments of the disclosure wherein a live viral vector is provided, such a vector may encode a recombinant fusion protein as a single entity, or may encode separate, distinct components or subunits that are able to assemble in vivo into a recombinant polypeptide as described herein.

The disclosure provides pharmaceutical compositions and related methods of using the therapeutic compositions or expression systems for inhibiting, preventing, or treating viral infections. Also provided is a use of the polynucleotides (DNA, RNA), polypeptides, and expression vectors or systems described herein for the manufacture of a medicament to prevent or treat viral infections. The pharmaceutical composition can be either a therapeutic formulation or a prophylactic formulation. Typically, a pharmaceutical composition may contain one or more active ingredients and, optionally, some inactive ingredients. In some embodiments, the active ingredient may be a recombinant polypeptide, an expression vector, or an expression system as described herein. In some other embodiments, the active ingredient may include other antiviral agents in addition to the expression system of the disclosure. The composition may additionally include one or more pharmaceutically acceptable vehicles and, optionally, other therapeutic ingredients (for example, antibiotics or antiviral drugs). Various pharmaceutically acceptable additives may also be used in such compositions.

In some embodiments, an expression system in a pharmaceutical composition as described herein may contain an expression vector or a type of viral particle that may optimally express a recombinant polypeptide as described herein. In general, the amount of vector(s) or viral particles administered to achieve a particular outcome will vary depending on various factors including, but not limited to, the gene and promoter chosen, the condition, patient-specific parameters, e.g., height, weight, and age, and whether prevention or treatment is to be achieved. A vectors or viral particle of the disclosure may conveniently be provided in the form of formulations suitable for administration, e.g., into the blood stream (e.g., in an intracoronary artery). A suitable administration format may best be determined by a medical practitioner or clinician for each patient individually, according to standard procedures.

A pharmaceutical composition of the disclosure may be prepared in accordance with standard procedures well known in the art. See, e.g., Remingtons Pharmaceutical Sciences, 19th Ed., Mack Publishing Company, Easton, Pa., 1995; Sustained and Controlled Release Drug Delivery Systems, J. R. Robinson, ed., Marcel Dekker, Inc., New York, 1978; U.S. Pat. Nos. 4,652,441; 4,917,893; 4,677,191; 4,728,721; and 4,675,189. Pharmaceutical compositions of the disclosure may be readily employed in a variety of therapeutic or prophylactic applications for preventing or treating viral infections. For subjects at risk of developing a viral infection, a recombinant polypeptide or composition of the disclosure may be administered to provide prophylactic protection against viral infection. Depending on the specific subject and conditions, a protein product (e.g., recombinant polypeptide), RNA product (e.g., RNA molecule or composition thereof), or recombinant adeno vector product (e.g., viral, adenoviral, or adeno-associated viral-based product), compositions thereof, or drug products described in the present disclosure may be administered to a subject or patient by a variety of administration modes known to the person of ordinary skill in the art, for example, intramuscular, subcutaneous, intravenous, intra-arterial, intra-articular, intraperitoneal, intranasal, or parenteral routes. In some embodiments, a composition as described herein for treatment of SARS-CoV or SARS-CoV-2 may be administered via the nasal or respiratory pathway, for example with the use of an inhaler, nebulizer, infuser, or respirator. In some embodiments, a composition as described herein may be administered to a subject in need of such treatment for a time and under conditions sufficient to prevent, inhibit, and/or ameliorate a selected disease or condition or one or more symptom(s) thereof. For therapeutic applications, a composition may contain a therapeutically effective amount of the expression system described herein. For prophylactic applications, a composition as described herein may contain a prophylactically effective amount of an expression system as described herein. The appropriate amount of the expression system (expression vectors or viral particles) may be determined based on the specific disease or condition to be treated or prevented, severity, age of the subject, and other personal attributes of the specific subject (e.g., the general state of the subject's health and the robustness of the subject's immune system). Determination of effective dosages may additionally be guided with animal model studies (i.e., primate, canine, or the like), followed by human clinical trials, and by administration protocols that significantly reduce the occurrence or severity of targeted disease symptoms or conditions in the subject. In some embodiments, a dosage of a recombinant polypeptide, composition, or drug as described herein may be any dosage deemed appropriate by a clinician or physician. In some embodiments, a dosage of heparin may be any clinical dose suitable for use in a patient, such as including, but not limited to, a concentration of about 0.1 $\mu M$, about 1 $\mu M$, or about 10 $\mu M$. In some embodiments, a dosage of 10-100 $\mu M$, or 20-50 $\mu M$, or 20-100 $\mu M$, or 10-50 $\mu M$, or the like may be used. In some embodiments, heparin may be administered at a dosage of, for example, 5,000-10,000 units, or 10,000 to 20,000 units, or 20,000 to 30,000 units, or 30,000 to 40,000 units, or 40,000 to 50,000 units, or the like. In some embodiments, a dosage of heparin may be 0-15 units, or 10-20 units, or 18-25 units, or 20-30 units, or 25-40 units, or 30-50 units, or 40-70 units, or 75-100 units, or 90-150 units, or 125-550 units, or 500-750 units, or 700-1,000 units, or 1,000-3,000 units, or 2,500-5,000 units, or 5,000-7,500 units, or 7,500-1,000 units.

For prophylactic applications, a composition as described herein may be provided in advance of any symptom, for example in advance of infection. A prophylactic administration of the immunogenic compositions may serve to prevent or ameliorate any subsequent infection. Thus, in some embodiments, a subject to be treated is one who has, or is at risk for developing, a viral infection, for example because of exposure or the possibility of exposure to the virus. Following administration of a therapeutically effective amount of the disclosed therapeutic compositions, a subject or patient may be monitored for viral infection, symptoms associated with viral infection, or both.

For therapeutic applications, a composition as described herein may be provided at or after the onset of a symptom of disease or infection, for example after development of a symptom of viral infection, or after diagnosis of infection. A composition as described herein may thus be provided prior to the anticipated exposure to virus so as to attenuate the anticipated severity, duration or extent of an infection and/or associated disease symptoms, after exposure or suspected exposure to the virus, or after the actual initiation of an infection.

In some embodiments, a vector or viral particle of the disclosure may be provided in a dosage form containing an amount of a vector effective in one or multiple doses. For viral vectors, an effective dose may be any range deemed appropriate by a clinician or practitioner. Administration of a recombinant polypeptide, vector, viral particle, expression system, or composition may be in a buffer, such as phosphate buffered saline, or other appropriate buffer or diluent. The amount of buffer or diluent may vary and would be determined by a clinician or practitioner. For delivery of RNA, plasmid DNA alone, or plasmid DNA in a complex with other macromolecules, the amount of DNA to be administered would be an amount that results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered. For delivery of a recombinant polypeptide of the disclosure, an amount administered would be an amount that results in a beneficial effect to the recipient. For example, from 0.0001 to 100 g or more, e.g., up to 1 g, in individual or divided doses, e.g., from 0.001 to 0.5 g, or 0.01 to 0.1 g, of recombinant polypeptide can be administered.

In some embodiments, a composition of the disclosure may be combined with other agents known in the art for treating or preventing viral infections. These may include any drug known or available in the art for treating a viral infection, e.g., antibodies or other antiviral agents such as replicase inhibitors, protease inhibitors, and fusion protein inhibitors. Administration of a composition and one or more known anti-viral agent may be either concurrently or sequentially.

As used herein, the terms "sequence identity," "sequence similarity," or "homology" are used to describe sequence relationships between two or more nucleotide sequences. The percentage of "sequence identity" between two sequences is determined by comparing two optimally aligned sequences over a specific number of nucleotides, wherein the portion of the sequence in the comparison window may comprise additions or deletions (i.e., gaps) as compared to a reference sequence. Two sequences are said to be identical if nucleotides at every position are the same. A nucleotide sequence when observed in the 5' to 3' direction is said to be a "complement" of, or complementary to, a second nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

Polynucleotides and polypeptides contemplated within the scope of the subject disclosure can also be defined in terms of more particular identity and/or similarity ranges with those sequences of the disclosure specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

RNA Molecules/Compositions for Preventing Viral Infection

In some embodiments, the disclosure provides a RNA molecule for treatment or prevention of a viral infection. Such a RNA molecule may comprise a first ribonucleotide sequence having a 5'-Cap or expressing an Internal Ribosome Entry Site (IRES); and second ribonucleotide sequence expressing a recombinant polypeptide as described herein.

As used herein, a "5'-Cap" or "5' Cap" refers to the incorporation of a GTP "cap" structure in place of the free triphosphate group that is present on the first incorporated nucleotide at the 5' end of a newly transcribed mRNA following transcription. The 5'-Cap is part of the post-transcriptional processing of a RNA transcript and involves the reaction between the 5' end of the RNA transcript and a GTP molecule, catalyzed by guanyl transferase. The 5'-Cap plays a role in ribosomal recognition of mRNA during translation of the mRNA into protein.

As used herein, an "IRES" refers to a RNA element or a region of an RNA molecule that is able to recruit the eukaryotic ribosome to the mRNA. An IRES allows for initiation of protein translation without requiring a 5'-cap for assembly of the initiation complex. Thus, in some embodiments, introduction of an IRES to a RNA molecule as described herein enables production of a recombinant polypeptide of the disclosure in a cap-independent manner, as part of the greater process of protein synthesis. In eukaryotic translation, initiation of protein translation typically occurs at the 5' end of an mRNA molecule. In some embodiments, an IRES included in a RNA molecule as described herein enables the recombinant polypeptide to be translated by the cells of the subject or patient to whom such a molecule is administered. A T7 promoter (such as provided in SEQ ID NO:19) may be added upstream of an IRES. Large-scale RNA production can be accomplished in vitro using, for example, a T7 polymerase. RNA may be injected subcutaneously in saline with or without liposome. The injected RNA will be translated within the cells of the patient and the resulting translated recombinant polypeptide is secreted.

A recombinant polypeptide as described herein may contain multiple distinct polypeptide chains (e.g., immunoglobulin heavy chains and a light chains) of which one chain contains sulfation sites as described herein but requires one or more of the other polypeptide chains in order to bind to a host cell-surface receptor protein or fragment thereof.

Methods for Preventing or Treating Viral Infection

In some embodiments, the disclosure provides a method of preventing or treating a viral infection in a subject in need thereof, comprising administering to the subject a therapeutically or prophylactically effective amount of a pharmaceutical composition as described herein. Such a method may comprise administration of a recombinant polypeptide as described herein to a subject or patient, or may comprise administration of a vector or expression system encoding such a recombinant polypeptide. In other embodiments, a method of the disclosure may comprise administration of a composition as described herein, such as a composition comprising a recombinant polypeptide of the present disclosure.

A method of the present disclosure may treat or prevent infection of a subject or patient with a virus from the flaviviridae or coronaviridae viral families, as described herein. Any virus from these families may be treated with a method of the disclosure, as described herein. In some embodiments, particular viruses that may be advantageously treated or prevented with a method of the disclosure may include, but is not limited to, HCV and MERS. Administration of a composition or recombinant polypeptide as described herein may be in a clinical setting as described herein, or may be in an alternate setting as deemed appropriate by a clinician or practitioner. Further embodiments for administration of such compounds or polypeptides are described herein elsewhere.

Expression of Nucleic Acids

Polynucleotides useful in the present disclosure can be provided in an expression construct. Expression constructs of the disclosure generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements used for expression of nuclear genes include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the disclosure can comprise a promoter sequence operably linked to a polynucleotide sequence encoding a polypeptide of the disclosure. Promoters can be incorporated into a polynucleotide using standard techniques known in the art. Multiple copies of promoters or multiple promoters can be used in an expression construct of the disclosure. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

Nuclear Expression constructs of the disclosure may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the disclosure. Classical enhancers are cis-acting elements that increase gene transcription and can also be included in the expression construct. Classical enhancer elements are known in the art, and include, but are not limited to, the cytomegalovirus (CMV) early promoter enhancer element, and the SV40 enhancer element. Intron-mediated enhancer elements that enhance gene expression are also known in the art. These elements must be present within the transcribed region and are orientation dependent.

DNA sequences that direct polyadenylation of mRNA transcribed from the expression construct can also be included in the expression construct, such as an SV40 poly A signal, and include, but are not limited to, an octopine synthase or nopaline synthase signal.

Polynucleotides of the present disclosure can be composed of either RNA or DNA, or hybrids thereof. The present disclosure also encompasses those polynucleotides that are complementary in sequence to the polynucleotides disclosed herein. Polynucleotides and polypeptides of the disclosure can be provided in purified or isolated form.

Nucleic Acids

Any number of methods well known to those skilled in the art can be used to isolate and manipulate a DNA molecule. For example, as previously described, PCR technology may be used to amplify a particular starting DNA molecule and/or to produce variants of the starting DNA molecule. DNA molecules, or fragments thereof, can also be obtained by any techniques known in the art, including directly synthesizing a fragment by chemical means. Thus, all or a portion of a nucleic acid as described herein may be synthesized.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. The polynucleotide sequence includes both the sense and antisense strands either as individual strands or in the duplex.

Kits

The disclosure further provides a kit comprising one or more single-use containers comprising a recombinant polypeptide as described herein. In some embodiments, a kit of the disclosure may provide a viral vector for administration to a subject or patient. In some embodiments, a kit may provide a pharmaceutical composition comprising a recombinant polypeptide as described herein, for administration to a subject or patient. In other embodiments, sterile reagents and/or supplies for administration of a recombinant polypeptide, RNA, viral vector, and/or pharmaceutical composition as described herein, may be provided as appropriate. A kit may further comprise reagents for cell transformation and/or transfection, viral and/or cell culture, or both. In some embodiments, a kit described herein may comprise reagents and materials for performing in vitro transcription to synthesize mRNA, e.g., components known and available in the art in, for example, an in vitro transcription kit.

Components provided in a kit of the disclosure may include, for example, any starting materials useful for performing a method as described herein. Such a kit may comprise one or more such reagents or components for use in a variety of assays, including for example, nucleic acid assays, e.g., PCR or RT-PCR assays, luciferase (Luc) assays, cell transformation/transfection, viral/cell culture, blood assays, i.e., complete blood count (CBC), viral titer/viral load assays, antibody assays, viral antigen detection assays, viral DNA or RNA detection assays, virus neutralization assays, genetic complementation assays, or any assay useful in accordance with the disclosure. For viral strains that result in genetic or genomic alterations or mutations in the hose, such as retroviruses, certain genotyping assays for identification of viral sequences within a host genome may be useful and are encompassed within the disclosure. Components may be provided in lyophilized, desiccated, or dried form as appropriate, or may be provided in an aqueous solution or other liquid media appropriate for use in accordance with the disclosure.

Kits useful for the present disclosure may also include additional reagents, e.g., buffers, substrates, antibodies, ligands, detection reagents, media components, such as salts including $MgCl_2$, a polymerase enzyme, deoxyribonucleotides, ribonucleotides, expression vectors, and the like, reagents for DNA isolation, DNA/RNA transfection, or the like, as described herein. Such reagents or components are well known in the art. Where appropriate, reagents included with such a kit may be provided either in the same container or media as a primer pair or multiple primer pairs. In some embodiments, such reagents may be placed in a second or additional distinct container into which an additional composition or reagents may be placed and suitably aliquoted. Alternatively, reagents may be provided in a single container means. A kit of the disclosure may also include packaging components, instructions for use, including storage requirements for individual components as appropriate. Such a kit as described herein may be formulated for use in a clinical setting, such as a hospital, treatment center, or clinical setting, or may be formulated for personal use as appropriate.

Definitions

The definitions and methods provided define the present disclosure and guide those of ordinary skill in the art in the practice of the present disclosure. Unless otherwise noted, terms are to be understood according to conventional usage by those of ordinary skill in the relevant art. Definitions of common terms in molecular biology may also be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 CFR § 1.822 is used.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

Conservative amino acid substitutions providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); Arginine (R), Lysine (K); 5) Isoleucine (I), Leucine (L), Methionine (M), Valine (V); and 6) Phenylalanine (F), Tyrosine (Y), Tryptophan (W). Not all residue positions within a protein will tolerate an otherwise "conservative" substitution. For instance, if an amino acid residue is essential for a function of the protein, even an otherwise conservative substitution may disrupt that activity, for example the specific binding of an antibody to a target epitope may be disrupted by a conservative mutation in the target epitope.

In some embodiments, conservative amino acid substitutions, e.g., substituting one acidic or basic amino acid for another, can often be made without affecting the biological activity of a recombinant polypeptide as described herein. Minor variations in sequence of this nature may be made in any of the peptides disclosed herein, provided that these changes do not substantially reduce (e.g., by 15% or more) the ability of the peptide or fusion polypeptide to neutralize the entry of a lentivirus into its host cells.

As used herein, "ACE2" or "ACE2R" refers to the angiotensin converting enzyme 2 (ACE2) receptor, which is often used as a viral receptor.

As used herein, "epitope" refers to an antigenic determinant or receptor binding domain. Epitopes are particular chemical groups or peptide sequences on a molecule that are antigenic, such that they elicit a specific immune response, for example, an epitope is the region of a viral Env protein or antigen to which B and/or T cells respond. Epitopes may be formed both from contiguous amino acids or noncontiguous amino acids juxtaposed by tertiary folding of a protein.

As used herein, an "effective amount" of a recombinant protein, composition, compound, drug, nucleic acid molecule, or other agent refers to an amount that is sufficient to generate a desired response, such as reduce or eliminate a sign or symptom of a condition or disease. For instance, as described herein, an effective amount may be an amount necessary to inhibit viral entry into a host cell, or to inhibit viral replication or to measurably alter outward symptoms of a viral infection. In general, this amount will be sufficient to measurably inhibit virus replication or infectivity. When administered to a subject, a dosage will generally be used that will achieve target tissue concentrations (for example, in lymphocytes) that has been shown to achieve in vitro inhibition of viral entry or replication. In some examples, an "effective amount" is one that treats (including prophylaxis) one or more symptoms and/or underlying causes of any of a disorder or disease. In one example, an effective amount is a therapeutically effective amount. In one example, an effective amount is an amount that prevents one or more signs or symptoms of a particular disease or condition from developing.

As used herein, a "fusion protein" refers to a recombinant polypeptide or protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, as described herein, the amino acid sequences of one or more host cell surface receptors, such as CD81, ACE2, HSPG, and/or SRB1, are not normally found joined together via a peptide bond.

As used herein, "gene delivery" refers to the introduction of an exogenous polynucleotide into a cell for gene transfer, and may encompass targeting, binding, uptake, transport, localization, replicon integration and expression.

As used herein, "gene transfer" refers to the introduction of an exogenous polynucleotide into a cell which may encompass targeting, binding, uptake, transport, localization and replicon integration, but is distinct from and does not imply subsequent expression of the gene.

As used herein, "gene expression" or "expression" refers to the process of gene transcription, translation, and post-translational modification.

As used herein, "subject" or "patient" refers to any animal classified as a mammal, e.g., human and non-human mammals. Examples of non-human animals include dogs, cats, cattle, horses, sheep, pigs, goats, rabbits, etc. Unless otherwise noted, the terms "patient" or "subject" are used herein interchangeably. In some embodiments, a subject amenable for therapeutic applications of the disclosure may be a primate, e.g., human and non-human primates.

As used herein, administration of a polynucleotide or vector into a host cell or a subject refers to introduction into the cell or the subject via any routinely practiced methods. This includes "transduction," "transfection," "transformation," or "transducing," as well known in the art. These terms all refer to standard processes for the introduction of an exogenous polynucleotide, e.g., a transgene in rAAV vector, into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and western blot, measurement of DNA and RNA by assays, e.g., northern blots, Southern blots, reporter function (Luc) assays, and/or gel shift mobility assays. Methods used for the introduction of the exogenous polynucleotide include well-known techniques such as viral infection or transfection, lipofection, transformation, and electroporation, as well as other non-viral gene delivery techniques. The introduced polynucleotide may be stably or transiently maintained in the host cell.

Transcriptional regulatory sequences of use in the present disclosure generally include at least one transcriptional promoter and may also include one or more enhancers and/or terminators of transcription. Operably 8inked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

The term "treating" or "alleviating" includes the administration of compounds or agents to a subject to prevent or delay the onset of the symptoms, complications, or biochemical indicia of a disease (e.g., a viral infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

A "vector" is a nucleic acid with or without a carrier that can be introduced into a cell. Vectors capable of directing the expression of genes encoding for one or more polypeptides are referred to as "expression vectors." Examples of vectors suitable for the present disclosure include, e.g., viral vectors, plasmid vectors, liposomes, and other gene delivery vehicles.

As used herein, "AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV that is identified by and distinguished from other AAVs based on capsid protein reactivity with defined antisera, e.g., serotypes including AAV-1 to AAV-8. For example, serotype AAV-2 is used to refer to an AAV that contains capsid proteins encoded from the cap gene of AAV-2 and a genome containing 5' and 3' UTR sequences from the same AAV-2 serotype. Pseudotyped AAV refers to an AAV that contains capsid proteins from one serotype and a viral genome including 5'-3' UTRs of a second serotype. Pseudotyped rAAV would be expected to have cell surface binding properties of the capsid serotype and genetic properties consistent with the TPS serotype. The abbreviation "rAAV" refers to recombinant adeno-associated viral particle or a recombinant AAV vector (or "rAAV vector"). An "AAV virus" or "AAV viral particle" refers to a viral particle composed of at least one AAV capsid protein (preferably by all of the capsid proteins of a wild-type AAV) and an encapsidated polynucleotide. If the particle comprises a heterologous polynucleotide (i.e., a polynucleotide other than a wild-type AAV genome such as a transgene to be delivered to a mammalian cell), it is typically referred to as "rAAV."

As used herein, "domain" refers to a polypeptide that includes an amino acid sequence of an entire polypeptide or a functional portion of a polypeptide. Certain functional subsequences are known, and if they are not known, can be determined by truncating a known sequence and determining whether the truncated sequence yields a functional polypeptide.

As used herein, "expression construct" refers to a nucleic acid construct that includes an encoded exogenous nucleic acid protein that can be transcribed and translated for functioning in the recipient to which it was administered. In some embodiments, such an expression construct may comprise DNA sequences, RNA sequences, or combinations thereof. In some embodiments, such a construct may be genetically engineered into a vector appropriate for administration in a subject or patient, such as a human patient. For example, as described herein, a construct of the present disclosure may comprise a nucleic acid sequence encoding a recombinant polypeptide comprising: a) an Ig Fc fragment and a sulfated polysaccharide; and b) at least one viral receptor or fragment thereof.

In some embodiments, an expression construct may be provided to a subject or patient as a viral vector. Viral vectors are well known in the art and may be any viral vector appropriate for the present disclosure. For example, in some embodiments, a construct as described herein may be an adenoviral vector. One of skill in the art would be able to identify an appropriate viral vector for administration to a subject or patient, such as a human subject.

As used herein, "exogenous sequence" refers to a nucleic acid sequence that originates outside the host cell. An exogenous sequence may be a DNA sequence, an RNA sequence, or a combination thereof. Any type of nucleic acid available in the art may be used in accordance with the disclosure, as would be understood by one of skill in the art. Such a nucleic acid sequence can be obtained from a different species, or the same species, as that of the cell into which it is being delivered. In some embodiments, an exogenous nucleic acid sequence in accordance with the disclosure may encode a recombinant polypeptide as described herein, suitable for administration to a subject or patient. Such a recombinant polypeptide may be administered to a subject or patient in order to treat or prevent viral infection.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a," and "an," and "the," and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and can also cover other unlisted steps. Similarly, any composition or device that "comprises," "has," or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

Examples of embodiments of the present disclosure are provided in the following examples. The following examples are presented only by way of illustration and to assist one of ordinary skill in using the disclosure. The examples are not intended in any way to otherwise limit the scope of the disclosure.

Example 1. Minimal Domain for Sulfation of HSPGR

HSPG with a sulfated site naturally acts as a receptor for certain viruses at the sulfated site. Fragments of heparan sulfate proteoglycan core protein were created with 1, 2, or 3 SGD sulfation sites. HSmin refers to a small peptide of 16, 21, or 24 amino acids that contains recognition signals with 1, 2, or 3 sulfation sites, as follows:

HS24:
(SEQ ID NO: 1)
DDEYMLADSISGDDLGSGDLGSGD

HS21:
(SEQ ID NO: 2)
DDEYMLADSISGDDLGSGDLG

Hs16:
(SEQ ID NO: 3)
DDEYMLADSISGDDLG

An endogenous cellular enzyme adds a sulfo group to each serine residue of each SGD motif. All of the above sequences are sulfated at each serine residue of each SGD motif to produce mono-, di-, or tri-sulfated peptides. These peptides were used to construct a sulfated fusion protein having a sulfated Fc region, called Fc-$SO_4$.

The cDNA sequence was cloned into the 3' end of an Fc coding sequence and expressed in cells.

The sequence of the human HSPG2 gene corresponds to UniProtKB—P98160 (PGBM_HUMAN).

Expression of various R-Ig proteins was evaluated in 293T cells, using rabbit anti-human IgG Ab-HRP, 1:2000 for 1 hour (see FIG. 8). Lane 3 shows expression of a CD26 receptor fragment conjugated to an Ig-Fc and heparan sulfate. Lane 4 shows the same construct, but with 2 alanine residues included at the N-terminus of the signal peptide to increase secretion of the recombinant polypeptide. Lane 5 shows an SRB1 receptor fragment conjugated to a CD81 receptor fragment, an Ig-Fc, and heparan sulfate. Lane 6 shows the same as Lane 5, but with the same 2 alanine residues described above to increase secretion. Lane 7 shows a CD81 receptor fragment conjugated to an Ig-Fc and heparan sulfate. For this example, CD26 refers to the blade-4 portion of the protein.

Example 2. Coding Sequences

Human DNA sequences containing receptor coding regions (e.g., CD81, SRB1, HSPG, CD26) were obtained from GenBank. Extracellular domains of these proteins, from which the transmembrane domains were deleted, were used to synthesize coding sequences. HS24 is a small peptide sequence taken from the 5'-proximal end of HSPG. This synthetic DNA was amplified by PCR to be cloned into plasmid DNA. Coding sequences for human IgG1-Fc, the hinge region, and various signal peptide sequences were similarly obtained and amplified by PCR.

Example 3. Coding Sequences

An in-frame DNA cassette coding for the following construct was generated by overlapping PCR: 5'-signal peptide-MCS (multiple cloning sites)-hinge-human IgFc-MCS-HS24 peptide-3'. This cassette was inserted into an expression vector with human elongation factor promoter, pFUSEN-hG1Fc by InvivoGen, which utilizes the hEF1/HTLV R-U5 sequence as a hybrid promoter (Kim et al., *Gene* 91:217-23, 1990; Takebe, *Mol Cell Biol* 9:4248-58, 1988), and the SV40 poly A site; or an expression vector with CMV promoter, pCl by Promega, which uses the CMV I.E. enhancer/promoter with the SV40 poly A site. The sequence of this new expression vector was confirmed and named pFc-HS. The extracellular domain of the CD81 sequence was synthesized and added in-frame to the 5' MCS to create pCD81-Fc-HS. The extracellular domain of SRB1 was added upstream of CD81 by overlapping PCR to create pSRB1-CD81-Fc-HS. The extracellular domain of CD26 was inserted to the 5' MCS of pFc-HS to create pCD26-Fc-HS.

Example 4. Cells

Human embryonic kidney cell line HEK293T, human hepatoma cell line Huh7 cells, and African green monkey kidney cell line COS cells were maintained in Dulbecco's modified Eagle medium (DMEM) containing 10% FCS at 37° C. in 5% $CO_2$.

Example 5. Transfection and Expression In Vitro

Sub-confluent cells grown overnight in complete medium on Petri dishes were washed with Options-MEM (Invitrogen). Prior to transfection, DNA was mixed with Lipofectamine 2000 (Invitrogen) in Opti-MEM and incubated for 30 min at room temperature, and then added to the washed cells. Cells were incubated for 6 hours and grown further for up to 48 hours in complete medium.

Example 6. Purification

Recombinant receptor-Fc-HS protein was purified from conditioned medium or from cell lysates by Protein-A or Protein-G agarose column chromatography.

Example 7. Western Blot Analysis

Recombinant proteins were subject to SDS-Page under reducing conditions and transferred to cellulose nitrate filters. Proteins were visualized using rabbit anti-human IgG1 conjugated with horseradish peroxidase (HRP).

Example 8. ELISA Assay

The wells of 96-well plates are coated with MERS spike protein or HCV E1E2 protein. The coated plates are blocked (BioLegend, San Diego, Ca), incubated with serially diluted Receptor-Fc-HS proteins for 2 hr at RT, incubated with 1/1000 dilution of horseradish peroxidase-conjugated goat-anti human Fc (LSBio, Inc) for 1 hr at RT, washed, and then tetramethylbenzidine (TMB) substrate (BD Bioscience) was added. The reaction was stopped with 2N $H_2SO_4$, and the absorbency read at 450 nM.

Example 9. Determination of Virus Neutralization Titer

The ability of CD81-Fc-HS protein to neutralize HCV infection will be measured by using live HCV virus (JFH1) as described in U.S. Pat. Publ. No. 2010/0227311 A1. The ability of CD26-Fc-HS will be measured by using live MERS-CoV virus as described (Jung et al., *Vaccine* 36:3468-76, 2018).

Example 10. Construction of Fusion Protein for Preventing Viral Infection

A recombinant polypeptide (i.e., fusion protein) is constructed using, for example, an immunoglobulin (Ig) Fc fragment, a fragment of a host cell surface receptor, such as CD81, and a fragment or a second receptor, such as SRB1, and a peptide with a sulfated polysaccharide such as HS24 (SEQ ID NO:1). The receptor fragment of the fusion protein binds the viral envelope protein and results in or enables binding of the second receptor. The binding is co-operative and more stable than either molecule alone. The ability of the recombinant polypeptide to bind cell-surface receptors is analyzed.

Example 11. In Vitro/In Vivo Inhibiting Activities of Recombinant Polypeptides

The activity of the recombinant polypeptide is assessed in various conditions in vitro and in vivo. Affinity of the recombinant polypeptide to the given viral envelope is measured by quantitative ELISA using a purified envelope protein of the virus to determine the binding constant. Virus neutralization potential of the recombinant polypeptide is measured using cell culture in vitro. In this assay, doses of the virus are incubated with cell culture to determine the infectious dose. Then measured doses of the test protein is pre-incubated with test virus before the infection of the cell culture to establish the virus neutralization titer of the recombinant protein. Comparison of this neutralization titer to that of monoclonal antibodies with known values will provide the first indication of potency of the recombinant proteins. The efficacy of the recombinant protein could be tested in small animal models. For example, HCV could be tested in a transgenic mouse model in which mice with severe combined immune deficiency (SCID) are grafted with human liver, or in which the murine CD81 gene is knocked out and human receptors such as CD81 are expressed. These mice can be infected with HCV and assessed. Likewise, MERS could be tested in transgenic mice transfected with human CD26, although these mice retain expression of murine CD26 and express human CD26 only transiently. These animals could be tested for prophylactic applications, in which animals are pre-treated with the test protein before a challenge dose of virus is given intravenously to monitor virus control. In a therapeutic application, animals already infected with test virus are administered the test protein to measure the change in viremia and viral clearance. Chimpanzee is the only animal infected by HCV. Naive chimpanzee can be used to test prophylactic potential of the HCV recombinant polypeptide, whereas the animal thigh already infected with HCV can be used to test therapeutic application of the test protein.

Example 12. RNA Expression Vector

An RNA expression vector may be used to express RNA encoding a recombinant polypeptide as described herein. A construct may be prepared by using the DNA coding sequence for the desired RNA transcript, along with a 5'-CAP or an IRES for translation. A 5'-CAP or IRES included in a RNA molecule as described herein enables the recombinant polypeptide to be translated by the cells of the subject or patient to whom such a vector is administered. In some embodiments, a T7 promoter of approximately 20 nucleotides (SEQ ID NO:19) may also be added upstream of the protein coding sequence. Large-scale RNA production can be accomplished in vitro using, for example, a T7 polymerase and 5'-Cap analogue. The resulting RNA can be injected intramuscularly or subcutaneously in saline with or without liposome. The injected RNA with a 5'-Cap will be translated within the cells of the patient and the resulting translated recombinant polypeptide is secreted.

Example 13. Creation of Fc-HS Protein by Transferring 24-aa HS Peptide from Perlecan to Fc Heparan sulfate (HS) and chondroitin sulfate (CS) are the two major forms of sulfated GAG (glycosaminoglycan). Both HS and CS share tetra-saccharides attached to the amino acid serine (Ser) during the HSPG biosynthesis pathway, which are the following: (Ser)-xylose (Xyl)-galactose (Gal)-galactose (Gal)-glucuronic acid (GlcA). For HS, the fifth sugar is N-acetylglucosamine (GlcNAc), while CH has N-acetylgalatosamine (GalNAc). In addition, the sixth sugar is GlcA. The fifth and sixth sugars are then repeated multiple times in both HS and CH.

For HS, the GlcA residue within the repeating disaccharide unit can either remain, or it can be epimerized into iduronic acid (IdoA). Sulfate ($SO_4$) is then added to GlcNAc (as many as three, at carbons 2, 3, and 6), and to IdoU (one at carbon 2). One notable HS is heparin, which is an anti-coagulant that is purified from pig intestine and size-fractionated into low-molecular weight (MW, 15-kDa) species.

Expression and visualization of purified Fc-HS and Fc-T3 proteins is shown in FIG. 9. The amino acid sequence of HS present in Fc-HS is as follows:

```
                                        (SEQ ID NO: 20)
              DDEDMADSISGDDLGSGDLGSGD.
```

The amino acid sequence of T3 present in Fc-T3 is as follows:

```
                                        (SEQ ID NO: 21)
              DDEDMADSITGDDLGTGDLGTGD.
```

The Fc-HS has a 23-amino acid HS-peptide with 3 Ser residues in bold. They are expected to be GAG-glycosylation site. The Fc-T3 has a 23-amino acids peptide where the 3 Ser residues are replaced with Thr.

Fc-HS and Fc-T3 were expressed in 293T cells, and the secreted proteins were purified from culture medium. Proteins were subjected to 10% SDS-PAGE under reducing conditions and visualized by Coomassie Blue staining.

Example 14. Cleavage of Heparin by Heparinase

Heparin was digested with the indicated enzymes at 30° C. for 24 h, analyzed by 20% SDS-PAGE, and visualized by alcian blue/silver staining (FIG. 10). Heparin is cleaved by Heparinase and stained by GAG-specific dye, alcian blue/silver. Heparinase-I hydrolyses GlcNAc-IdoU and Heparinase III digests GlcNAc-GlcA. Alcian Blue is anionic dye that interacts with sulfate group present in HS. In combination with silver, it selectively detects the GAG chain present in proteoglycan (Min et al., Anal Biochem 209(1):169-75, 1993).

Example 15. Fc-HS Protein is GAG-Glycosylated

An EHS band was detectable when the gel was stained with the HS-specific dye, alcian blue/silver. Alcian blue/silver bands (FIG. 11) are abolished when the 3 Ser in Fc-HS are mutated to 3 Thr in Fc-T3. Each protein was found in the cell lysate and culture medium. Only secreted proteins are GAG-glycosylated, glycosylation is coupled with the secretion pathway.

Example 16. Heparan Sulfate Made in Fc-Proteins Linked with HS Peptides

Proteins were expressed in 293T cells. Secreted proteins in media were bound to Protein A beads and partially digested with Heparinase I or Heparinase III. Digested proteins were analyzed by 10% SDS-PAGE, followed by alcian blue/silver staining to visualize GAG glycoproteins (FIG. 12).

GAG-glycosylation is evident by the presence of slow-migrating smear bands in Fc-HS and CD81-Fc-HS samples. These smear bands were converted into ladders by Heparinase. The smear bands/ladder are missing in CD81-Fc, which does not encode HS peptide. HS is made, mainly in GlcA-form (heparinase-III sensitive), some in IdU-form (Heparinase-I sensitive).

Three different sources of HS GAG-chain are as follows (amino acid residues for the predicted O-linked GAG-glycosylation sites are shown in bold):

A 23-amino acid HS peptide from Perlecan:

```
                                        (SEQ ID NO: 20)
              DDEDMADSISGDDLGSGDLGSGD.
```

A 30-amino acid HS peptide from Glypican 5:

```
                                        (SEQ ID NO: 22)
         GSGGGMVEQVSGDCDDEDGCGGSGSGEVKR.
```

A 26-amino acid HS peptide from Syndecan 4:

```
                                        (SEQ ID NO: 23)
            PGQESDDFELSGSGDLDDLEDSMIGP.
```

Example 17. Generation of Retrovirus-Based SARS-CoV-2 Pseudovirus Particles

SARS-CoV-2 pseudotyped (i.e., pseudovirus) particles (Spp) were generated with a murine leukemia virus (MLV) core and luciferase reporter as described (*J Visualized Expt*, 2019 145, 1-9). To this end, a packaging cell line (Pt-gp), which expresses MLV gag and pol (Cell Biolabs, #RTV 003), and a transfer vector plasmid pBabe (Cell Biolab #RTV-001) that encodes a GFP reporter gene and an MLV Ψ-RNA packaging signal, along with 5'- and 3'-flanking MLV long terminal repeat (LTR) regions were obtained. This vector was modified to include fruit fly luciferase (FLuc) along with GFP to create pGFP-FLuc. A second plasmid was also used that encodes the SARS-CoV-2 spike (S) protein of interest. These two plasmids were co-transfected into the packaging cells using Lipofectamine 3000 (Thermo) following the manufacturer's protocol. Upon co-transfection, viral RNA and proteins get expressed within transfected cells allowing generation of pseudotyped particles (pp). Within these pp, the RNAs containing the luciferase gene reporter and packaging signal get encapsulated into nascent particles that bud out from cells to culture medium with the S protein at their surface. The medium was harvested and cleared by centrifugation (290 g×7 min) for use in infectivity assays. Upon infection in target cells, the viral RNA containing the luciferase reporter and flanking LTRs is then released within the cell and the retroviral polymerase activities enable its reverse transcription into DNA and integration into the host cell genome. Quantification of the infectivity of pp in infected cells is then performed with a simple luciferase activity assay. Because the DNA sequence that gets integrated into the host cell genome only contains the luciferase gene and none of the MLV or coronavirus protein-encoding genes, they are inherently safer. SARS-CoV-2 Spp are the excellent surrogates of native virions for studying viral entry into host cells. See FIG. 13 for luminescence results of individual cell types.

A highly permissive cell line for SARS-CoV-2 Spp infection was obtained. To this end, VeroE6 cells were transfected with a plasmid DNA pCMV-TMPRSS2 described in [0213], and one cell clone (clone 7) was selected as a stable VeroE6/TMPRSS2 cell line by screening multiple clones by Spp infection assays (FIG. 14).

Constructs and Plasmids.

SARS-CoV and MERS-CoV spike glycoprotein sequences were taken from Genbank Accession Nos. AY30120 and AGN70962, respectively, and were used to synthesize each cDNA. SARS-CoV-2 S glycoprotein sequence was taken from GenBank (Accession No. MN908947.3). Codon-optimized S protein cDNA sequence cloned into pCMV plasmid was purchased from Sino Biological (VG40589-UT) and referred to as pS. The S protein cDNA with the C-terminal 19 amino acids deleted (d19) was made by PCR and re-inserted into pCMV14 to create pS-d19. S protein cDNA with the cytoplasmic tail replaced with the HIV Env glycoprotein tail (CCSCGSCC, SEQ ID NO:52) was made and re-inserted into pCMV14 to create pS-HIV. ACE2 is an entry receptor for SARS-CoV and SARS-CoV-2, and its sequence was obtained from GenBank (Accession No. AF241254). A plasmid encoding this sequence was purchased from Sino Biological (HG10108-M) and cloned into pCMV14 to create pCMV-ACE2. Three constructs were produced as described herein. The ectodomain of ACE2 (aa 18-738) was amplified by PCR and inserted into pFc to create pAce-2Fc, or inserted into pFc-HS to create pAce2-Fc-HS (sequence shown in FIG. 20A and FIG. 20B as well as the schematic in FIG. 5). Both constructs have 2 amino acids (Ala-Ala) insertion at the N-terminus of the protein to increase the secretion of protein into cell culture medium. The minimal domain of ACE2 (aa 22-44 and aa 351-357), which was reported to inhibit SARS-CoV entry to cells (*Virology* 2006, 350, 15-25) was inserted into pFc to produce pAce2p6-Fc (sequence shown in FIG. 19A and FIG. 19B). The receptor domains (aa 19-44 and aa 325-355 linked with 3 glycine residues), possibly involved in contact to SARS-CoV-2 Spike (S) protein, was inserted to pFc to produce p61-Fc (sequence shown in FIG. 21A and FIG. 21B). A cDNA expression plasmid encoding serine protease TMPRSS2 was purchased from Sino Biological and referred to pCMV-Tmprss2.

ACE2-Fc and ACE2-Fc-HS expressed in 293T cells are secreted into the culture medium. Proteins in conditioned medium in increasing volumes were electrophoresed in denaturing conditions as shown in FIG. 16A. Western blot was probed with anti-human IgG-Fc, and proteins were determined using known amounts of Fc protein included in the gel. Purification and characterization of the proteins expressed in Huh7 cells is shown in FIG. 16B. As shown, ACE2-Fc and ACE2-Fc-HS inhibited SARS-CoV (FIG. 17A and FIG. 18A, respectively) and SARS-CoV-2 (FIG. 17B and FIG. 18B, respectively) pseudovirus entry into VeroE6/TMPRSS2 cells. Sequences for construct P6Fc-HS are provided as SEQ ID NOs:25-30. Sequences for construct Ace2Fc-HS are provided as SEQ ID NOs:25, 28, 30, 34-36, and 38. Sequences for construct P61Fc-HS are provided as SEQ ID NOs: 25, 28, 30, and 39-44.

Spp Preparation:

(1) Pt-gp cells were seeded at $6 \times 10^6$ cells in DMEM-complete medium in 10-cm dishes and incubated overnight (16-18 h) in a cell culture incubator with 5% $CO_2$ at 37° C.

(2) The cell culture medium was removed and 250 µl of Opti-MEM medium containing 5 µg pGFP-Luc, 2.5 µg pS, 20 µl of Lipofectamine 3000 was added. Cells were incubated for 6 h.

(3) Cells were washed and cultured in 10 ml of complete medium for 48 h.

(4) The medium containing Spp was cleared for cell debris by centrifugation and frozen in aliquots.

Spp Infection:

94-well plates were seeded with $1 \times 10^4$ cells/well in 100 µl DMEM-complete medium containing 10% FCS.

(1) The plate was incubated.

(2) The cell culture supernatants were removed. Meanwhile the pp were pre-incubated with test sample as indicated at 37° C. for 1 hr in 40 µl volume of complete medium.

(3) Cells were inoculated with the 40 µl of pre-incubated pp solution.

(4) Cells were incubated in a 37° C., 5% $CO_2$ cell culture incubator for 2 h.

(5) 60 µl of pre-warmed (37° C.) DMEM-C medium was added to each well to adjust volume of 100 µl.

(6) Cells were incubated in a 37° C., 5% $CO_2$ cell culture incubator for 48 hrs.

Infectivity Quantification:

The Luciferase Assay System (Luciferase Assay system, Promega E4030) was used for infectivity quantification.

(1) Luciferin substrate and 5× luciferase assay lysis buffer were thawed until they reached room temperature.

(2) Luciferase assay lysis buffer was diluted to 1× with sterile water.

(3) Aspirate supernatants of cells were infected with pseudotyped particles.

(4) 20 µl of 1× luciferase assay lysis buffer was added to each well.

(5) Plates were placed on a rocker and incubated for 15 min with rocking at room temperature.

(6) Microcentrifuge tubes were prepared for each well by adding 20 µl of luciferin substrate in each tube.

(7) Luminometer was turned on and a luciferase activity measurement was performed one well at a time by transferring 2 µl of lysate to one tube containing 4 µl of luciferin substrate.

(8) Tubes were gently flicked to mix contents, but to avoid displacing the liquid on walls of tube.

(9) Tubes were placed in the luminometer device and the lid closed.

(10) Luminescence of the tubes was measured and the relative light unit's measurement was recorded.

Data Analysis:

At the time of double transfection into packaging cells to produce pp, a mock transfection was performed, where the second plasmid coding for spike coding sequence was deleted. This transfection will not produce pp, and therefore luciferase activity measurable from these target cells represents a background measurement. This value was referred to as dEnv and was subtracted from Luc value from samples for normalization. The normalized Luc value from transduced cells with pp alone was taken as 100% infection.

Example 18. Heparin is an Efficient Inhibitor of SARS-CoV-2 Infection

Heparin was identified as an efficient inhibitor for SARS-CoV-2 infection in target cells (VeroE6 or VeroE6 cells constitutively expressing TMPRSS2). TMPRSS2 proteolytically activates SARS-CoV-2 in vitro and in vivo, and therefore VeroE6/TMPRSS2 cells are useful for assaying infectivity of the virus. As shown in FIG. 22, heparin blocks SARS-CoV-2 virus infection at a TCID50 of less than 1 μM range. In addition, heparin inhibits SARS-CoV-2 more efficiently than it does for SARS-CoV and MERS CoV.

Example 19. Inhibition of SARS-CoV-2 Pseudovirus Infection by Neutralizing Monoclonal Antibody SARS-CoV-2 spike S1 neutralizing mouse monoclonal antibody (Mab) was purchased from SinoBiological and used to test whether it could be used to prevent SARS-CoV-2 infection of a cell. As shown in FIG. 15, the mouse Mab was capable of neutralizing (inhibiting) virus infection at around 2 nM, which agrees what is reported by the vendor (SinoBiological). Thus, this data demonstrate that the pp assay described herein above provides a reliable way of measuring virus neutralization.

Example 20. Expression of Ace2-Fc and Ace2-Fc-HS in 293T Cells

Purification and characterization of the recombinant polypeptides described herein and expressed in 293T cells was performed as described in Example 17. Results are shown in FIG. 16B. Reduced or non-reduced proteins in increasing volume were electrophoresed in denaturing conditions. Western blot was probed with anti-human IgG-Fc. FIG. 16B shows an SDS-PAGE gel of a western blot demonstrating purification and characterization of proteins Ace2-Fc (left) and Ace2-Fc-HS (right) expressed in 293T cells, compared to control Fc alone.

Example 21. Heparin is an Efficient Inhibitor of SARS-CoV and MERS Infection

Similar to Example 18 above, heparin was also identified as an efficient inhibitor for both SARS-CoV pseudovirus infection in VeroE6 cells and MERS-CoV pseudovirus infection in Huh7 cells. As shown in FIG. 23, heparin blocks SARS-CoV virus infection and MERS-CoV virus infection at a TCID50 of between ~1 and 2.5 μM.

Example 22. Multimerization of ACE2-Fc Recombinant Proteins

Recombinant ACE2-Fc polypeptides can be prepared in multimeric form, for example dimeric, trimeric, tetrameric, hexameric, octameric, decameric, etc. FIGS. 24-29 demonstrate possible arrangements for such multimeric forms of a recombinant polypeptide of the present disclosure.

Tetrameric ACE2-Fc Using Streptavidin (SA) and Biotin:

To make a tetrameric form of an ACE2-Fc recombinant polypeptide in cell culture, streptavidin (SA) having biotin binding sites is added to a dimeric ACE2-Fc molecule at the ends opposite of the ACE2 viral receptor groups to form ACE2-Fc-SA dimers. These dimers when combined together in culture will spontaneously form tetramers when the SA groups associate together, forming ACE2-Fc-SA tetramers. This process is depicted in FIG. 24. The association of the SA groups of each ACE2-Fc-SA dimer will result in a tetramer in which the ACE2-Fc-SA dimers are joined end to end. The resulting tetrameric recombinant protein is expressed and secreted in cell culture.

Octameric ACE2-Fc Using Streptavidin (SA) and Biotin:

To make an octameric ACE2-Fc recombinant polypeptide in vitro, an ACE2-Fc-SA dimer as described above is allowed to form tetramers in vitro. The ACE2-Fc-SA tetramers are then combined with dimeric ACE2-Fc having a Strep-tag II® at the ends opposite of the ACE2 viral receptor groups. The dimeric ACE2-Fc-Strep-tag II® will bind to the biotin binding sites on the SA groups to form an octameric structure as shown in FIG. 25.

Tetrameric ACE2-Fc Using Streptavidin (SA) and Biotinylated AviTag™:

To make a tetrameric form of an ACE2-Fc recombinant polypeptide in cell culture, dimeric ACE2-Fc having a biotinylated AviTag™ at the ends opposite of the ACE2 viral receptor groups is combined with SA with biotin binding sites. The biotinylated AviTag™ groups present on the dimeric ACE2-Fc-AviTag™ will bind to the biotin binding sites on the SA groups to form a tetrameric structure in which the ACE2-Fc-Avitag™ dimers are joined end to end as shown in FIG. 26.

Octameric ACE2-Fc Using Streptavidin (SA) and Biotinylated AviTag™:

To make an octameric ACE2-Fc recombinant polypeptide in vitro, an ACE2-Fc-AviTag™ dimer as described above is combined with tetrameric ACE2-Fc-SA. The biotinylated AviTag™ groups present on the dimeric ACE2-Fc-AviTag™ will bind to the biotin binding sites on the SA groups of the ACE2-Fc-SA tetramers to form an octameric structure as shown in FIG. 27.

Tetrameric ACE2-Fc Using Streptavidin (SA) and AviTag™ Biotinylated with Heparin:

To make a tetrameric form of an ACE2-Fc recombinant polypeptide in cell culture, dimeric ACE2-Fc having an AviTag™ biotinylated with heparin at the ends opposite of the ACE2 viral receptor groups is combined with SA with biotin binding sites. The heparin-biotinylated AviTag™ groups present on the dimeric ACE2-Fc-AviTag™ will bind to the biotin binding sites on the SA groups to form a tetrameric structure in which the ACE2-Fc-AviTag™ dimers are joined end to end as shown in FIG. 28.

Octameric ACE2-Fc Using Streptavidin (SA) and AviTag™ Biotinylated with Heparin:

To make an octameric ACE2-Fc recombinant polypeptide in vitro, an ACE2-Fc-AviTag™ dimer as described above is combined with tetrameric ACE2-Fc-SA. The biotinylated AviTag™ groups present on the dimeric ACE2-Fc-Avitag™ will bind to the biotin binding sites on the SA groups of the ACE2-Fc-SA tetramers to form an octameric structure as shown in FIG. 29.

Example 23. Inhibition of SARS-CoV-2 Pseudovirus Infection in VeroE6/TMPRSS2 Cells by ACE2-Fc and ACE2-Fc-SA Measured by Luc Activity The ACE2-Fc and ACE2-Fc-SA constructs described in the previous Example were used to test infectivity of MLV-S19pp pseudovirus particles to VeroE6/TMPRSS2 cells, and the percent infection was determined by Luciferase (Luc) assay as described herein. Expression of ACE2-Fc-SA tetramer in cells, partially denatured by SDS, is shown in FIG. 31A. FIG. 30B shows that both ACE2-Fc and ACE2-Fc-SA reduced percent infection of SARS-CoV-2 pseudovirus particles. In addition, ACE2-Fc-SA reduced the percent infection much quicker than ACE2-Fc. ACE2-Fc and ACE2-Fc-HS also inhibited infection a specific variant of SARS-CoV-2 (D614G) having a mutation in the Spike protein (FIG. 34).

What is claimed is:

1. A recombinant polypeptide comprising an amino acid sequence set forth as SEQ ID NOs:31, 37, or 45.

2. The recombinant polypeptide of claim 1, further comprising a sulfated polysaccharide.

3. The recombinant polypeptide of claim 1, further comprising streptavidin.

4. The recombinant polypeptide of claim 2, wherein the sulfated polysaccharide is a heparan sulfate (HS).

5. A pharmaceutical composition comprising the recombinant polypeptide of claim 1.

6. A method of treating a SARS-CoV or SARS CoV-2 infection in a subject in need thereof, comprising administering to the subject an effective amount of the pharmaceutical composition of claim 5.

7. The method of claim 6, wherein the pharmaceutical composition is administered by inhaler, by intra-nasal spray, or intravenously.

8. The method of claim 6, further comprising administration of heparin.

\* \* \* \* \*